US012672861B2

(12) United States Patent
Berger et al.

(10) Patent No.: US 12,672,861 B2
(45) Date of Patent: Jul. 7, 2026

(54) LEFT ATRIAL APPENDAGE MANIPULATION

(71) Applicant: Append Medical Ltd., Or Yehuda (IL)

(72) Inventors: Zachi Berger, Nes Ziona (IL); Shay Raviv, Zur Hadassa (IL); Oded Meiri, Moshav Ram-On (IL); Gal Atarot, Kfar Saba (IL)

(73) Assignee: Append Medical Ltd., Or Yehuda (IL)

( * ) Notice: Subject to any disclaimer, the term of this patent is extended or adjusted under 35 U.S.C. 154(b) by 634 days.

(21) Appl. No.: 17/624,386

(22) PCT Filed: Jul. 2, 2020

(86) PCT No.: PCT/IL2020/050737
§ 371 (c)(1),
(2) Date: Jan. 3, 2022

(87) PCT Pub. No.: WO2021/001830
PCT Pub. Date: Jan. 7, 2021

(65) Prior Publication Data
US 2022/0354472 A1     Nov. 10, 2022

Related U.S. Application Data

(60) Provisional application No. 62/869,603, filed on Jul. 2, 2019.

(51) Int. Cl.
A61B 17/00     (2006.01)
*A61B 17/30*     (2006.01)

(52) U.S. Cl.
CPC .............................. A61B 17/0057 (2013.01); *A61B 2017/00243* (2013.01); *A61B 2017/00292* (2013.01);
(Continued)

(58) Field of Classification Search
CPC ........... A61B 2017/00623; A61B 2017/00632; A61B 2017/00663; A61B 2017/306
See application file for complete search history.

(56) References Cited

U.S. PATENT DOCUMENTS 6,231,561 B1 * 5/2001 Frazier ............... A61B 17/0401
604/500
8,114,123 B2 * 2/2012 Brenzel .............. A61B 17/1285
606/151
(Continued)

FOREIGN PATENT DOCUMENTS

CN          1342056       3/2002
CN          103108597      5/2013
(Continued)

OTHER PUBLICATIONS

International Preliminary Report on Patentability Dated Jan. 13, 2022 From the International Bureau of WIPO Re. Application No. PCT/IL2020/050737. (13 Pages).
(Continued)

*Primary Examiner* — Alexander J Orkin

(57)          ABSTRACT

A method for closure of the left atrial appendage (LAA), including: placing an LAA reshaper in contact with an LAA wall or near the LAA wall; invaginating at least a portion of the LAA into the left atrium (LA); reshaping by the LAA reshaper the LAA during the invagination; fastening the invaginated at least a portion of said LAA; and retracting the LAA reshaper from the LAA.

14 Claims, 35 Drawing Sheets

(52) U.S. Cl.
　　CPC ............... *A61B 2017/00623* (2013.01); *A61B 2017/00632* (2013.01); *A61B 2017/00663* (2013.01); *A61B 2017/306* (2013.01)

(56) References Cited

U.S. PATENT DOCUMENTS

| | | | | |
|---|---|---|---|---|
| 10,758,241 | B1 * | 9/2020 | Lashinski | ........ A61B 17/12031 |
| 2002/0111647 | A1 * | 8/2002 | Khairkhahan | ... A61B 17/12172 606/200 |
| 2004/0030335 | A1 * | 2/2004 | Zenati | .............. A61B 17/12013 606/51 |
| 2005/0021016 | A1 * | 1/2005 | Malecki | ............. A61B 18/1492 606/27 |
| 2006/0122680 | A1 * | 6/2006 | Auth | ................... A61B 18/1492 607/122 |
| 2006/0271089 | A1 * | 11/2006 | Alejandro | ......... A61M 25/0069 606/192 |
| 2006/0287674 | A1 * | 12/2006 | Ginn | .................... A61B 17/083 606/221 |
| 2008/0033241 | A1 | 2/2008 | Peh et al. | |
| 2010/0191279 | A1 * | 7/2010 | Kassab | ............ A61B 17/12031 606/213 |
| 2011/0077672 | A1 | 3/2011 | Fleischman | |
| 2011/0276075 | A1 | 11/2011 | Fung et al. | |
| 2013/0006343 | A1 | 1/2013 | Kassab | |
| 2014/0018831 | A1 | 1/2014 | Kassab et al. | |
| 2014/0088636 | A1 | 3/2014 | Feischman et al. | |
| 2014/0171733 | A1 * | 6/2014 | Sternik | ............ A61B 17/00234 600/37 |
| 2015/0142101 | A1 | 5/2015 | Coleman et al. | |
| 2016/0022273 | A1 | 1/2016 | Kassab | |
| 2017/0340329 | A1 | 11/2017 | Groothuis et al. | |
| 2018/0085130 | A1 * | 3/2018 | Fung | .................... A61B 90/361 |
| 2018/0235640 | A1 | 8/2018 | Slaughter et al. | |
| 2019/0262003 | A1 | 8/2019 | Kiser et al. | |
| 2022/0051396 | A1 | 2/2022 | Bur et al. | |

FOREIGN PATENT DOCUMENTS

| | | |
|---|---|---|
| CN | 108926371 | 12/2018 |
| WO | WO 2010/006061 | 1/2010 |
| WO | WO-2017035363 A1 * | 3/2017 .......... A61B 17/064 |
| WO | WO 2018/178979 | 10/2018 |
| WO | WO 2019/112879 | 6/2019 |
| WO | WO 2021/001830 | 1/2021 |

OTHER PUBLICATIONS

International Search Report and the Written Opinion Dated Oct. 28, 2020 From the International Searching Authority Re. Application No. PCT/IL2020/050737. (20 Pages).

Summary Dated Jan. 16, 2024 of Notification of Office Action Dated Jan. 2, 2024 From the National Intellectual Property Administration of the People's Republic of China Re. Application No. 202080059309.1. (4 Pages).

Supplementary European Search Report and the European Search Opinion Dated May 26, 2023 From the European Patent Office Re. Application No. 20834353.3. (9 Pages).

Requisition by the Examiner Dated Jul. 26, 2023 From the Innovation, Science and Economic Development Canada, Canadian Intellectual Property Office Re. Application No. 3,144,325. (5 Pages).

Examination Report Under Sections 12 & 13 of the Patents Act, 1970 and the Patents Rules, 2003 Dated Mar. 19, 2024 From the Government of India, Intellectual Property India, Patents, Designs, Trade Marks, Geographical Indications, The Patent Office Re. Application No. 202227005480. (7 pages).

Notification of Office Action and Search Report Dated Jan. 2, 2024 From the National Intellectual Property Administration of the People's Republic of China Re. Application No. 202080059309.1 and Its Machine Translation Into English. (29 Pages).

Notification of Office Action Dated Jun. 26, 2024 From the State Intellectual Property Office of the People's Republic of China Re. Application No. 202080059309 and Its Machine Translation Into English. (29 Pages).

English Summary of Office Action Dated Jun. 26, 2024 From the State Intellectual Property Office of the People's Republic of China Re. Application No. 202080059309. (4 Pages).

Communication Pursuant to Article 94(3) EPC Dated Nov. 13, 2025 From the European Patent Office Re. Application No. 20834353.3 (8 Pages).

* cited by examiner

Fig. 6I

Fig. 7A
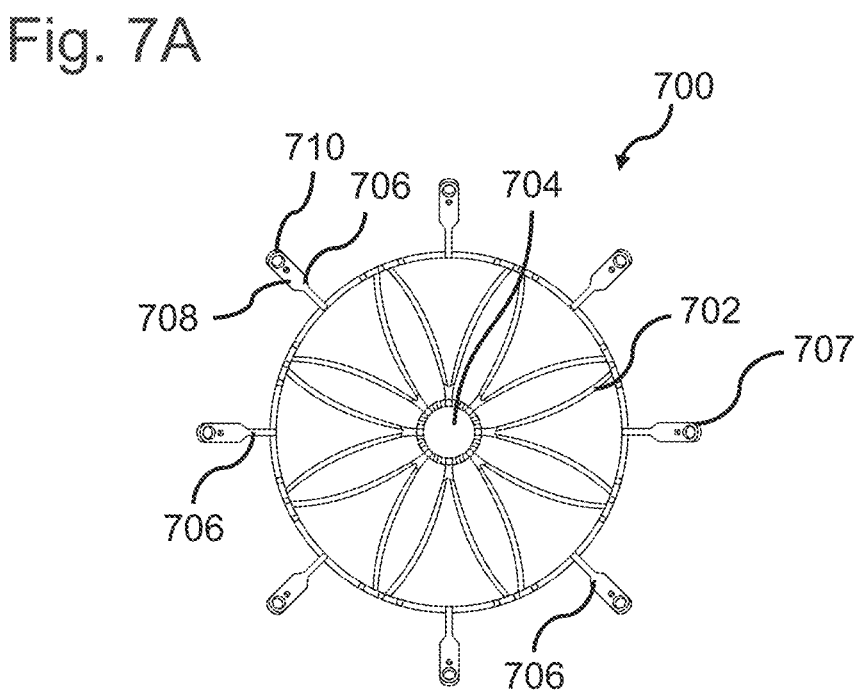
Fig. 7B
Fig. 7C
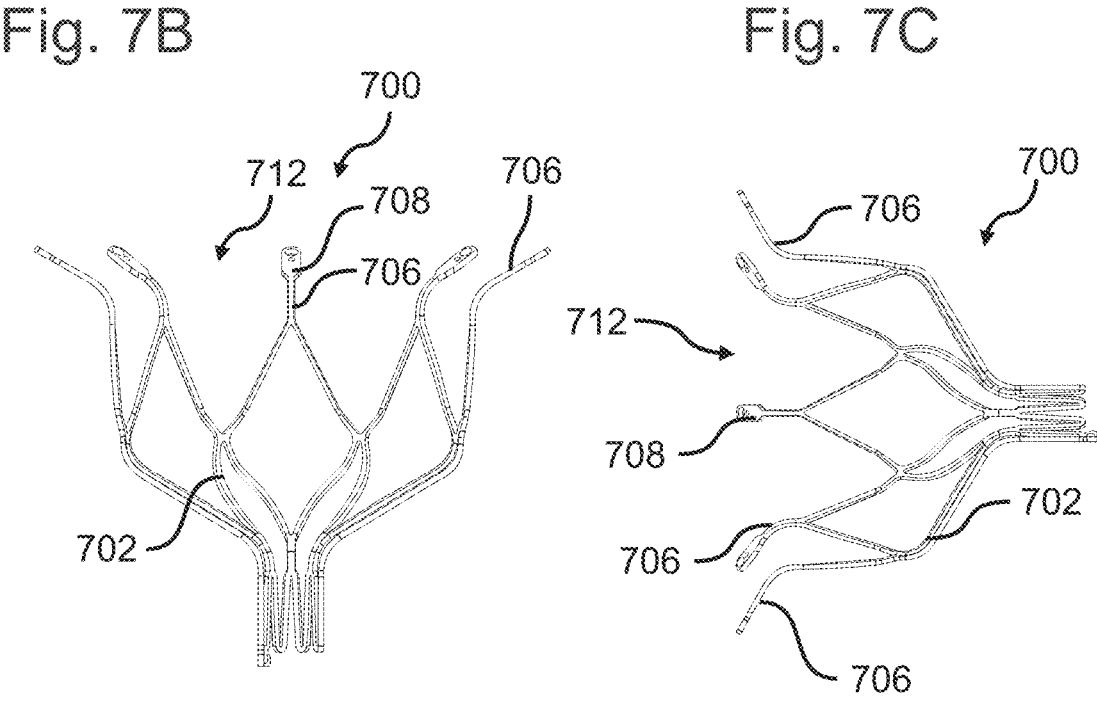

Fig. 9A
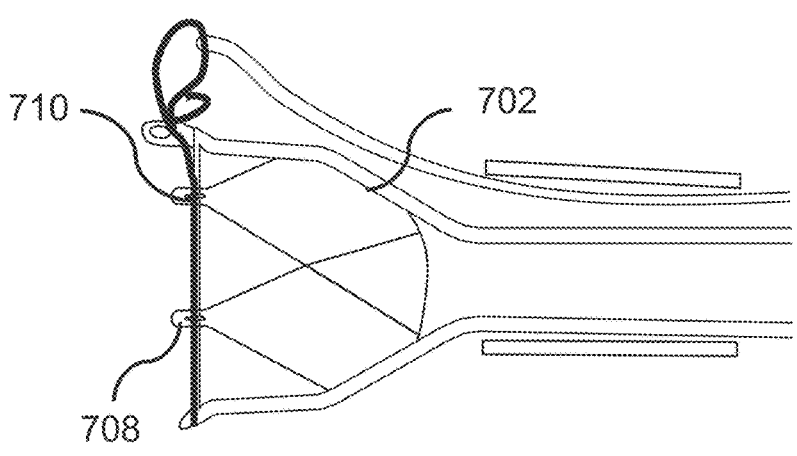
Fig. 9B
Fig. 9C
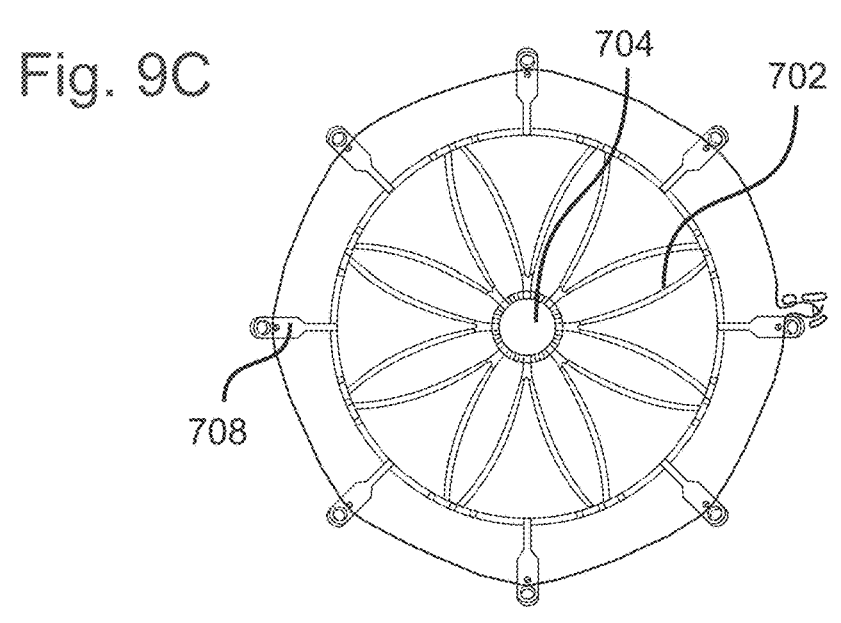

302

| Inserting reshaper into the LAA opening | 1530 |

| Sealing the LAA from the outside (optional) | 1532 |

| Sealing the LAA from the inside (optional) | 1534 |

| Invaginating LAA onto reshaper by vaccum application | 1536 |

| Fastening invaginated LAA by reshaper fastener | 1538 |

| Disconnecting fastener from reshaper (optional) | 1540 |

| Retracting Reshaper | 1542 |

| Retracting external seal (optional) | 1544 |

LEFT ATRIAL APPENDAGE MANIPULATION

RELATED APPLICATIONS

This application is a National Phase of PCT Patent Application No. PCT/IL2020/050737 having International filing date of Jul. 2, 2020, which claims the benefit of priority under 35 USC § 119(e) of U.S. Provisional Patent Application No. 62/869,603 filed on Jul. 2, 2019. The contents of the above applications are all incorporated by reference as if fully set forth herein in their entirety.

FIELD AND BACKGROUND OF THE INVENTION

The present invention, in some embodiments thereof, relates to closure of a body cavity and, more particularly, but not exclusively, to closure of the left atrial appendage (LAA).

SUMMARY OF THE INVENTION

Some examples of some embodiments of the invention are listed below. Features from one example may be combined with features of other examples:

Example 1. A method for closure of the left atrial appendage (LAA), comprising:

placing an LAA reshaper in contact with an LAA wall or near said LAA wall;

invaginating at least a portion of said LAA into the left atrium (LA);

reshaping by said LAA reshaper the LAA during said invagination;

fastening said invaginated at least a portion of said LAA; and retracting said LAA reshaper from the LAA.

Example 2. A method according to example 1, comprising extending a suction channel terminating with a vacuum inlet into said LA, and placing said vacuum inlet in contact with an LA wall surrounding or near an opening of said LAA.

Example 3. A method according to example 2, comprising applying vacuum on said LAA from outside the LAA through said vacuum inlet following said placing and during said invaginating and said reshaping.

Example 4. A method according to example 3, wherein said applying vacuum comprises applying said vacuum on said LAA from the LA.

Example 5. A method according to any one of examples 3 or 4, comprising at least partly inwardly collapsing said LAA by said applied vacuum.

Example 6. A method according to example 5, wherein said at least partly inwardly collapsing comprises at least partly inwardly collapsing said LAA on said LAA reshaper by said applied vacuum.

Example 7. A method according to example 2, wherein said placing comprises expanding said LAA reshaper at least partly within the LAA, and wherein said reshaping comprises applying force by said LAA reshaper on said LAA wall from within said LAA.

Example 8. A method according to example 7, wherein said retracting comprises retracting said LAA reshaper into said LA during said invaginating while applying said force.

Example 9. A method according to example 8, comprising applying vacuum on said LAA during said retracting.

Example 10. A method according to any one of examples 3 or 9, wherein said applied vacuum comprises high pressure vacuum in a range of 400-900 mmHg.

Example 11. A method according to any one of the previous examples, wherein said placing comprises inserting said LAA reshaper up to 30 mm into said LAA.

Example 12. A method according to any one of examples 1 to 10, wherein said placing comprises inserting said LAA reshaper up to 10 mm into said LAA.

Example 13. A method according to any one of the previous examples, wherein said placing comprises placing said LAA reshaper in contact with a proximal portion of the LAA adjacent to the LAA opening.

Example 14. A device for closure of the LAA, comprising:

a catheter introducible into the left atrium (LA) and comprising a working channel having a distal opening configured to face the LA;

an LAA reshaper extendable from said distal opening at least partly into the LAA through an opening of said LAA, a suction channel passing through said working channel and terminating with a vacuum inlet extendable from said working channel, said vacuum inlet configured to contact a wall of said LA around said LAA opening and to apply vacuum on said LAA; and at least one tissue fastener extendable into the LA from within said working channel and configured to fasten at least a portion of said LAA.

Example 15. A device according to example 14, wherein said LAA reshaper is coupled to said vacuum inlet.

Example 16. A device according to any one of examples 14 or 15, wherein said LAA reshaper is configured to forwardly extend from said vacuum inlet up to 10 mm into said LAA.

Example 17. A device according to any one of examples 14 to 16, wherein a maximal width of said LAA reshaper is smaller than a maximal width of said vacuum inlet.

Example 18. A device according to any one of examples 14 to 17, wherein a surface of said LAA reshaper comprises a plurality of openings shaped and sized to apply vacuum from a lumen of said LAA reshaper through said plurality of openings onto said LAA wall.

Example 19. A device according to any one of examples 14 to 18, wherein said LAA reshaper is shaped as a cone, and wherein an apex of said cone is located distally to said suction channel.

Example 20. A device according to example 19, wherein said cone apex extends at least partially through said LAA opening into said LAA.

Example 21. A device according to any one of examples 19 or 20, wherein a distance between said cone apex and a base of said cone is adjustable.

Example 22. A device according to example 14, wherein said LAA reshaper is configured to be reversibly attachable to a wall of said LAA from within the LAA.

Example 23. A device according to example 22, wherein said LAA reshaper comprises an expandable LAA reshaper shaped and sized to acquire a collapsed state within said working channel of said catheter, and to expand within said LAA to contact said LAA wall.

Example 24. A device according to example 23, wherein said expandable LAA reshaper comprises a distal opening facing the LAA shaped and sized to allow application of vacuum through said distal opening on portions of the LAA not contacted by said LAA reshaper.

Example 25. A device according to any one of examples 23 or 24, wherein said expandable LAA reshaper is shaped and sized to acquire said collapsed state within said suction channel and to extend from within said vacuum inlet into said LAA.

Example 26. A device according to any one of examples 22 to 25, wherein a surface of said LAA reshaper comprises a plurality of openings shaped and sized to apply vacuum from a lumen of said LAA reshaper through said plurality of openings onto said LAA wall.

Example 27. A device according to example 26, wherein said LAA reshaper comprises a mesh, and wherein said plurality of openings are pores of said mesh.

Example 28. A device according to any one of examples 22 to 27, wherein said LAA reshaper is retractable into said working channel of said catheter while being attached to said LAA wall to evaginate at least a portion of said LAA into said LA.

Example 29. A device according to any one of examples 22 to 27, wherein said LAA reshaper is retractable into said vacuum inlet while being attached to said LAA wall to evaginate said LAA at least partly into said LA.

Example 30. A device according to any one of examples 14 to 29, wherein said vacuum is applied through said vacuum inlet with pressure sufficient to collapse a portion of said LAA onto said LAA reshaper and to evaginate at least partly said portion into said LA.

Example 31. A device according to any one of examples 28 to 30, wherein said at least one tissue fastener is shaped and sized to fasten said evaginated portion of said LAA positioned in the LA.

Example 32. A device according to example 31, wherein said at least one tissue fastener comprises a closable fastener loop shaped and sized to be positioned around said evaginated LAA portion.

Example 33. A device according to example 32, wherein said at least one tissue fastener comprises a fastener manipulator shaped and sized to pass through said working channel and connectable to said fastener loop, wherein said fastener manipulator is configured to close said fastener loop.

Example 34. A device according to example 33, wherein said fastener manipulator is shaped and sized to pass through said suction channel.

Example 35. A device according to any one of examples 33 or 34 wherein said fastener manipulator is releasable from said fastener loop in response to a signal from outside the body.

Example 36. A device according to any one of Examples 32 to 35, wherein said fastener loop is coupled to an inner surface of said vacuum inlet.

Example 37. A device according to any one of examples 32 to 35, wherein said fastener loop is coupled to an external surface of said vacuum inlet.

Example 38. A device according to any one of examples 32 to 34, wherein said fastener loop is coupled to the vacuum inlet by one or more of hooks, wires, elastic wires, cords, and/or elastic cords.

Example 39. A device according to any one of examples 36 to 38, wherein said fastener loop is configured to be released from said vacuum inlet when closed around said evaginated LAA portion.

Example 40. A device according to any one of examples 32 to 39, wherein said fastener loop comprises a wire.

Example 41. A device according to any one of examples 32 to 39, wherein said fastener loop comprises a band.

Example 42. A device according to any one of examples 32 to 41, wherein said fastener loop is configured to apply force of up to 30 Newtons on said evaginated LAA portion when said fastener loop is closed.

Example 43. A device according to any one of examples 32 to 42, wherein said fastener loop is made from ePTFE, polypropylene, peek, and/or polyurethane.

Example 44. A device according to any one of examples 32 to 43, wherein a surface of said fastener loop configured to contact LAA tissue is covered with one or more of bumps, bulges and protrusions shaped and sized to increase contact surface between said fastener loop and said LAA tissue.

Example 45. A device according to any one of examples 14 to 44, wherein a distal opening of said vacuum inlet facing the LAA has a width larger than a width of said LAA opening.

Example 46. A device according to example 45, wherein a width of said vacuum inlet is in a range of 10-50 mm.

Example 47. A device according to any one of examples 14 to 46, wherein at least a portion of said vacuum inlet configured to be placed in contact with said LAA wall is flexible.

Example 48. A device according to any one of examples 14 to 47, further comprising one or more sensors configured to sense electrical properties of at least one of the LA and the LAA.

Example 49. A device according to example 48, wherein said electrical properties comprise one or more of impedance and conductivity.

Example 50. A device according to any one of examples 14 to 49, further comprising one or more pressure sensors configured to sense pressure applied by said vacuum inlet on said wall of said LA around said LAA opening.

Example 51. A device according to any one of examples 14 to 50, further comprising one or more vacuum sensors configured to sense the level of vacuum applied through at least one of said suction channel and said vacuum inlet on LAA tissue.

Example 52. A method for positioning a left atrial appendage (LAA) remodeling tool near an ostium of the LAA, comprising:

placing, by an LAA reshaper guide, an LAA reshaper in contact with a wall of said LAA;

reshaping by said LAA reshaper the LAA during or after said placing;

advancing along said LAA reshaper guide an LAA remodeling tool configured to evaginate and/or to fasten at least a portion of the LAA evaginated into the LA, towards an ostium of the LAA located at the left atrium (LA);

attaching said LAA remodeling tool to a wall of said LA around said ostium, or to the LAA wall;

removing said LAA reshaper from the LAA after said attaching.

Example 53. A method according to example 52, wherein said reshaping comprises applying a force by an external surface of said LAA reshaper on said LAA wall, sufficient to anchor said LAA reshaper within said LAA during said advancing and said attaching.

Example 54. A method according to example 53, wherein said applying comprises applying a force of up to 30 Newtons by said LAA reshaper on said LAA wall.

Some additional examples of some embodiments of the invention are listed below. Features from one example may be combined with features of other examples:

Example 1. A method for closure of the left atrial appendage (LAA), comprising:

placing an LAA reshaper in contact with an LAA wall or near said LAA wall;

invaginating at least a portion of said LAA into the left atrium (LA);

reshaping by said LAA reshaper the LAA during said invagination;

fastening said invaginated at least a portion of said LAA; and retracting said LAA reshaper from the LAA.

Example 2. A method according to example 1, comprising applying vacuum on said LAA during said invaginating and said reshaping.

Example 3. A method according to example 2, wherein said applying comprises applying vacuum on said LAA through said LAA reshaper during said invaginating and said reshaping.

Example 4. A method according to any one of examples 2 and 3, comprising extending a suction channel terminating with a vacuum inlet into said LA, and placing said vacuum inlet in contact with an LA wall surrounding or near an opening of said LAA.

Example 5. A method according to example 4, wherein said applying comprises applying vacuum on said LAA from outside the LAA through said vacuum inlet following said placing and during said invaginating and said reshaping.

Example 6. A method according to example 5, wherein said applying vacuum comprises applying said vacuum on said LAA from the LA.

Example 7. A method according to any one of examples 2 to 6, comprising at least partly inwardly collapsing said LAA by said applied vacuum.

Example 8. A method according to example 7, wherein said at least partly inwardly collapsing comprises at least partly inwardly collapsing said LAA on said LAA reshaper by said applied vacuum.

Example 9. A method according to any one of examples 2 to 8, wherein said placing comprises expanding said LAA reshaper at least partly within the LAA, and wherein said reshaping comprises applying force by said LAA reshaper on said LAA wall from within said LAA.

Example 10. A method according to example 9, wherein said retracting comprises retracting said LAA reshaper into said LA during said invaginating while applying said force.

Example 11. A method according to example 10, comprising applying vacuum on said LAA during said retracting.

Example 12. A method according to any one of examples 2 to 11, wherein said applied vacuum comprises high pressure vacuum in a range of 400-900 mmHg.

Example 13. A method according to any one of the previous examples, wherein said placing comprises inserting said LAA reshaper up to 30 mm into said LAA.

Example 14. A method according to any one of the previous examples, wherein said placing comprises inserting said LAA reshaper up to 10 mm into said LAA.

Example 15. A method according to any one of the previous examples, wherein said placing comprises placing said LAA reshaper in contact with a proximal portion of the LAA adjacent to the LAA opening.

Example 16. A method according to any one of the previous examples, wherein said invaginating comprises invaginating said at least a portion of said LAA into said LAA reshaper and proximal to a fastener reversibly coupled to the LAA reshaper;

and wherein said fastening comprises fastening said invaginated at least a portion of said LAA by said fastener.

Example 17. A method according to example 16, comprising:

decoupling said fastener from said LAA reshaper by said fastening.

Example 18. A device for closure of the LAA, comprising:

a catheter introducible into the left atrium (LA) and comprising a working channel having a distal opening configured to face the LA;

an LAA reshaper extendable from said distal opening at least partly into the LAA through an opening of said LAA, a suction channel passing through said working channel and terminating with a vacuum inlet extendable from said working channel, said vacuum inlet configured to contact a wall of said LA around said LAA opening and to apply vacuum on said LAA; and at least one tissue fastener extendable into the LA from within said working channel and configured to fasten at least a portion of said LAA.

Example 19. A device according to example 18, wherein said LAA reshaper is coupled to said vacuum inlet.

Example 20. A device according to any one of examples 18 or 19, wherein said LAA reshaper is configured to forwardly extend from said vacuum inlet up to 10 mm into said LAA.

Example 21. A device according to any one of examples 18 to 20, wherein a maximal width of said LAA reshaper is smaller than a maximal width of said vacuum inlet.

Example 22. A device according to any one of examples 18 to 21, wherein a surface of said LAA reshaper comprises a plurality of openings shaped and sized to apply vacuum from a lumen of said LAA reshaper through said plurality of openings onto said LAA wall.

Example 23. A device according to any one of examples 18 to 22, wherein said LAA reshaper is shaped as a cone, and wherein an apex of said cone is located distally to said suction channel.

Example 24. A device according to any one of examples 18 to 23, wherein said LAA reshaper is configured to be reversibly attachable to a wall of said LAA from within the LAA.

Example 25. A device according to example 24, wherein said LAA reshaper comprises an expandable LAA reshaper shaped and sized to acquire a collapsed state within said working channel of said catheter, and to expand within said LAA to contact said LAA wall.

Example 26. A device according to example 25, wherein said expandable LAA reshaper comprises a distal opening facing the LAA shaped and sized to allow application of vacuum through said distal opening on portions of the LAA not contacted by said LAA reshaper.

Example 27. A device according to any one of examples 25 or 26, wherein said expandable LAA reshaper has a cylindrical or a cone shape in an expanded state, having a distal opening facing the LAA.

Example 28. A device according to example 27, wherein a maximal width of said expandable LAA reshaper distal opening in an expanded state is 30 mm.

Example 29. A device according to any one of examples 25 to 28 wherein a surface said expandable LAA reshaper is coated at least partly with a coating configured to form a sealed flow path between said LAA and said catheter.

Example 30. A device according to any one of examples 25 to 29, wherein said expandable LAA reshaper is shaped and sized to acquire said collapsed state within said suction channel and to extend from within said vacuum inlet into said LAA.

Example 31. A device according to any one of examples 24 to 25, wherein a surface of said LAA reshaper comprises a plurality of openings shaped and sized to apply vacuum from a lumen of said LAA reshaper through said plurality of openings onto said LAA wall.

Example 32. A device according to example 31, wherein said LAA reshaper comprises a mesh, and wherein said plurality of openings are pores of said mesh.

Example 33. A device according to any one of examples 24 to 32, wherein said LAA reshaper is retractable into said working channel of said catheter while being attached to said LAA wall to evaginate at least a portion of said LAA into said LA.

Example 34. A device according to any one of examples 24 to 32, wherein said LAA reshaper is retractable into said vacuum inlet while being attached to said LAA wall to evaginate said LAA at least partly into said LA.

Example 35. A device according to any one of examples 18 to 34, wherein said vacuum is applied through said vacuum inlet with pressure sufficient to collapse a portion of said LAA onto said LAA reshaper and to evaginate at least partly said portion into said LA.

Example 36. A device according to any one of examples 33 to 35, wherein said at least one tissue fastener is shaped and sized to fasten said evaginated portion of said LAA positioned in the LA.

Example 37. A device according to example 36, wherein said at least one tissue fastener comprises a closable fastener loop shaped and sized to be positioned around said evaginated LAA portion.

Example 38. A device according to example 37, wherein said at least one tissue fastener comprises a fastener manipulator shaped and sized to pass through said working channel and connectable to said fastener loop, wherein said fastener manipulator is configured to close said fastener loop.

Example 39. A device according to example 38, wherein said fastener manipulator is shaped and sized to pass through said suction channel.

Example 40. A device according to any one of examples 38 or 39 wherein said fastener manipulator is releasable from said fastener loop in response to a signal from outside the body.

Example 41. A device according to any one of examples 37 to 40, wherein said fastener loop is coupled to an inner surface or an external surface of said vacuum inlet.

Example 42. A device according to example 41, wherein said fastener loop is configured to be released from said vacuum inlet when closed around said evaginated LAA portion.

Example 43. A device according to any one of examples 37 to 40, wherein said fastener loop is releasably coupled to an inner surface or an external surface of said LAA reshaper.

Example 44. AA device according to example 43, wherein said fastener loop is configured to be released from said LAA reshaper when closed around said evaginated LAA portion.

Example 45. A device according to any one of examples 37 to 44, wherein said fastener loop comprises a wire or a band.

Example 46. A device according to any one of examples 37 to 45, wherein said fastener loop is configured to apply force of up to 30 Newtons on said evaginated LAA portion when said fastener loop is closed.

Example 47. A device according to any one of examples 18 to 46, wherein a distal opening of said vacuum inlet facing the LAA has a width larger than a width of said LAA opening.

Example 48. A device according to example 47, wherein a width of said vacuum inlet is in a range of 10-50 mm.

Example 49. A device according to any one of examples 18 to 48, wherein at least a portion of said vacuum inlet configured to be placed in contact with said LAA wall is flexible.

Example 50. A device for closure of the LAA, comprising:

a catheter introducible into the left atrium (LA) and comprising a working channel having a distal opening configured to face the LA;

an expandable LAA reshaper extendable from said distal opening at least partly into the LAA through an opening of said LAA, and expandable within said LAA, wherein said LAA reshaper comprises a distal opening facing said LAA;

a suction channel passing through said working channel and terminating with said expandable LAA reshaper, said expandable LAA reshaper is configured to expand and contact walls of said LAA and to apply vacuum on said LAA via said distal opening; and at least one tissue fastener extendable into the LA from within said working channel and configured to fasten at least a portion of said LAA.

Example 51. A device according to example 50, wherein said at least one tissue fastener is reversibly coupled to said expandable LAA reshaper.

Example 52. A device according to any one of examples 50 or 51, wherein said expandable LAA reshaper is coated at least partly with a coating non-permeable to air to form a sealed flow path between said LAA and said working channel.

Example 53. A method for positioning a left atrial appendage (LAA) remodeling tool near an ostium of the LAA, comprising:

placing, by an LAA reshaper guide, an LAA reshaper in contact with a wall of said LAA;

reshaping by said LAA reshaper the LAA during or after said placing;

advancing along said LAA reshaper guide an LAA remodeling tool configured to evaginate and/or to fasten at least a portion of the LAA evaginated into the LA, towards an ostium of the LAA located at the left atrium (LA);

attaching said LAA remodeling tool to a wall of said LA around said ostium, or to the LAA wall;

removing said LAA reshaper from the LAA after said attaching.

Example 54. A method according to example 53, wherein said reshaping comprises applying a force by an external surface of said LAA reshaper on said LAA wall, sufficient to anchor said LAA reshaper within said LAA during said advancing and said attaching.

Example 55. A method according to example 54, wherein said applying comprises applying a force of up to 30 Newtons by said LAA reshaper on said LAA wall.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by with specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIGS. 6A-6I are schematic illustrations of a process for LAA invagination and closure, according to some exemplary embodiments of the invention;

FIGS. 7A-7C are schematic illustrations of a vacuum inlet frame, according to some exemplary embodiments of the invention;

FIGS. 9A-9E are schematic illustrations and images of a vacuum inlet coupled to a fastener, according to some embodiments of the invention;

DESCRIPTION OF SPECIFIC EMBODIMENTS OF THE INVENTION

Figure 1:
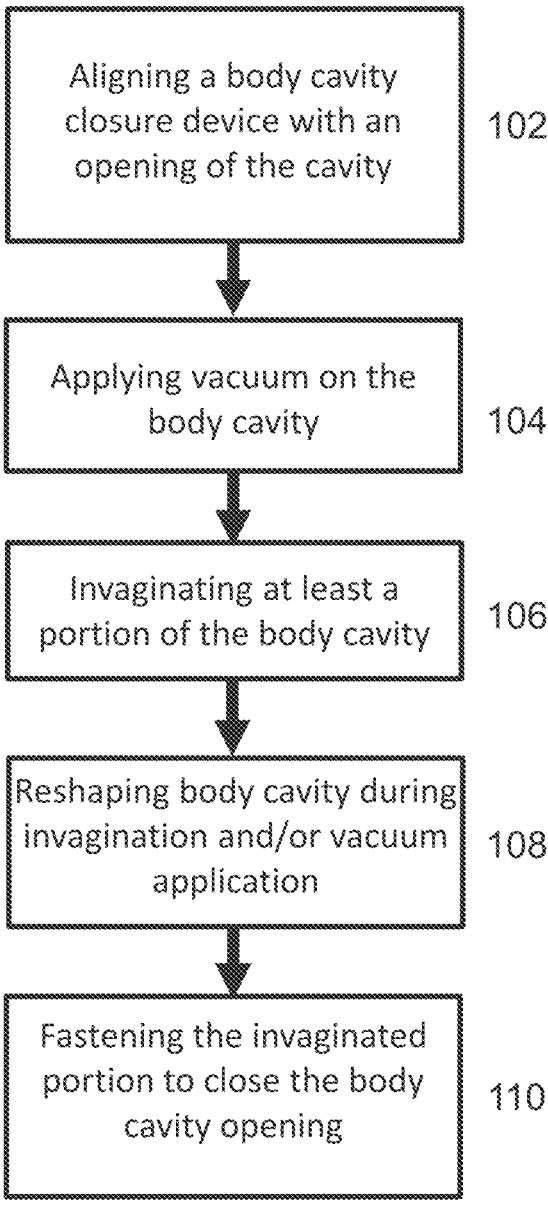
FIG. 1 is a general flow chart of a process for closure of a body cavity, according to some exemplary embodiments of the invention.

The present invention, in some embodiments thereof, relates to closure of a body cavity and, more particularly, but not exclusively, to closure of the left atrial appendage (LAA).

An aspect of some embodiments relates to reshaping LAA tissue. In some embodiments, the LAA tissue is reshaped during the invagination of at least a portion of the LAA into the LA. Alternatively or additionally, the LAA tissue is reshaped during collapse of the LAA, for example an inward collapse of the LAA. As used herein, an inward collapse of the LAA is a collapse of the LAA wall into the LAA cavity. The LAA is located at the LA of the heart, has a maximal length of up to about 40 mm, for example up to about 30 mm, up to about 20 mm or any intermediate, smaller or larger value. The LAA has a maximal wall thickness of up to about 1 mm, for example up to about 0.8 mm, up to about 0.5 mm or any intermediate, smaller or larger value. The LAA opening in the LA has a width in a range of 5-40 mm, for example 5-20 mm, 10-30 mm, 26-40 mm or any intermediate, smaller or larger value.

According to some embodiments, the LAA is reshaped during invagination, for example to control the shape, size and/or volume of an invaginated portion of the LAA. In some embodiments, the LAA is reshaped during invagination, for example by controlling forces applied on the LAA, for example suction forces and/or mechanical forces applied on the LAA. In some embodiments, the forces are applied on the LAA from the LA or from within the LAA cavity. In some embodiments, the strength of the forces is controlled, for example to LAA reshaping without damage to the LAA wall. In some embodiments, a direction of the forces is controlled, for example to allow invagination of a portion of the LAA with a desired shape, size and/or volume into the LA.

According to some embodiments, the LAA is reshaped during an inward collapse of the LAA, for example to control the size of the collapsed area. Alternatively or additionally, the LAA is reshaped in order to control the collapse extent, for example the collapse depth and/or whether the collapse is a complete collapse or a partial collapse of the LAA.

According to some embodiments, the LAA is reshaped by positioning an LAA reshaper at least partially inside the LAA cavity. In some embodiments, the LAA reshaper is introduced into the LAA cavity up to a maximal distance of 70 mm from the LAA opening inside the LA, for example up to 70 mm, up to 50 mm, up to 40 mm, up to 20 mm, up to 10 mm or any intermediate, smaller or larger distance from the LAA opening inside the LA. In some embodiments, the LAA reshaper is introduced at least 1 mm into the LAA cavity, for example at least 1 mm, at least 5 mm, at least 10 mm, at least 20 mm, or any intermediate, smaller or larger distance into the LAA cavity.

According to some embodiments, the LAA reshaper is placed in contact with a surface of the LAA wall located at the LAA cavity. In some embodiments, the LAA reshaper comprises an expandable LAA reshaper configured to expand and to make contact with the LAA wall from within the LAA cavity. In some embodiments, the LAA reshaper is pushed against the surface of the LAA wall located at the LAA cavity. Alternatively or additionally, the LAA reshaper penetrates up to 2.5 cm, for example up to 2 cm, up to 1.5 cm, up to 0.5 cm, up to 0.1 cm or any intermediate, smaller or larger value into the LAA wall from within the LAA cavity. In some embodiments the LAA reshaper is pushed against the LAA wall and/or penetrates through the LAA wall from within the LAA cavity to anchor the LAA reshaper at least partly within the LAA cavity. Optionally, the LAA reshaper is reversibly anchored within the LAA cavity and is configured to detach from the LAA wall, for example in response to a signal from outside the body. In some embodiments, the LAA reshaper is reversibly anchored, by acquiring an expanded state configured to place the LAA reshaper in contact with the LAA wall during anchoring, and a collapsed state configured to detach the LAA reshaper from the LAA wall. In some embodiments, during anchoring, for example reversible anchoring, the LAA reshaper applies force of up to 30 Newtons, for example up to 25 Newtons, up to 20 Newtons, up to 15 Newtons, up to 10 Newtons or any intermediate, smaller or larger value, on the LAA wall.

According to some embodiments, retraction of the LAA reshaper into the LA, while the LAA reshaper is in contact with the LAA wall, invaginates at least a portion of the LAA. In some embodiments, the invaginated portion is entirely positioned within the LAA cavity. Alternatively, the invaginated portion of the LAA is introduced at least partly into the LA. In some embodiments, the invaginated portion of the LAA is completely invaginated into the LA. In some embodiments, during retraction of the LAA reshaper into the LA, the LAA reshaper detaches from the LAA wall.

According to some embodiments, the LAA reshaper contacts the LAA wall, for example an inner portion of the LAA, when suction is applied on the LAA cavity. In some embodiments, vacuum forces applied by the suction induces an inward collapse of the LAA on a portion of the LAA reshaper positioned inside the LAA cavity. In some embodiments, the LAA reshaper is in a flow communication with a suction channel. In some embodiments, vacuum is applied through openings, for example adjustable openings, positioned to direct the collapse of the LAA on the LAA reshaper. In some embodiments, the collapse of the LAA onto the LAA reshaper reversibly attaches the LAA reshaper to the LAA wall. In some embodiments, retraction of the LAA reshaper into the LA cavity at least partly invaginates the collapsed LAA into the LA. Optionally, retraction of the LAA reshaper into the LA detaches the LAA wall of the collapsed LAA from the LAA reshaper.

According to some exemplary embodiments, the LAA reshaper is configured to extend from a distal opening of a working channel of a catheter or from a suction channel positioned within the working channel. In some embodiments, the LAA reshaper extends at least partly into the LAA through the LAA opening, for example up to 20 mm, up to 15 mm, up to 10 mm or any intermediate, smaller or larger value, from the LAA opening in the LA. In some embodiments, the LAA reshaper is configured to be reversibly attachable to a wall of the LAA from within the LAA, for example by expansion and collapse of the LAA reshaper within the LAA. In some embodiments, the LAA reshaper is reversibly attached to the LAA by friction only, without any anchors penetrating into the LAA tissue. Alternatively, the LAA is reversibly attached to the LAA by inserting one or more anchors, for example hooks, into the LAA tissue during the expansion of the LAA reshaper, and removing the one or more anchors from the LAA tissue during LAA reshaper collapse.

An aspect of some embodiments relates to aligning a catheter with a body cavity orifice, for example an opening of the LAA. In some embodiments, the catheter is aligned with the body cavity orifice, for example an LAA opening by anchoring an LAA reshaper at least partly within the LAA cavity. In some embodiments, the LAA reshaper is mechanically connected to the catheter, for example a working channel of the catheter. Alternatively, the LAA reshaper extends into the catheter, for example into the working channel of the catheter. In some embodiments, anchoring the LAA reshaper at least partly within the LAA cavity generates a guiding route between the catheter, for example a working channel of the catheter, and the LAA cavity or the LAA opening located in the LA.

An aspect of some embodiments relates to invaginating a body cavity, for example the LAA, by applying suction forces from outside the body cavity. In some embodiments, the suction forces are applied on the LAA cavity from outside the LAA cavity, for example from the LA. In some embodiments, the applied suction forces invaginate at least a portion of the LAA, at least partly into the LA.

According to some embodiments, application of suction forces from a vacuum inlet, for example a suction cup, of a suction channel positioned in the LA, attaches the vacuum inlet to the LA wall around the LAA opening. In some embodiments, the vacuum inlet is firmly attached to the LA wall with forces sufficient to form a sealed flow path between the suction channel and the LAA cavity. In some embodiments, the vacuum inlet is attached to the LA wall around the LAA opening without damaging the LA wall.

An aspect of some embodiments relates to sealing the LAA from within the LAA prior to LAA manipulation. In some embodiments, the LAA is sealed by an LAA reshaper configured to reshape the LAA during LAA invagination. In some embodiments, the LAA is invaginated using vacuum applied through an opening, for example a distal opening of the sealed LAA reshaper. Optionally, an external seal, for example the vacuum inlet placed in the LA around the LAA opening, is used in combination with the sealed LAA reshaper.

According to some embodiments, a fastener coupled, for example reversibly coupled to the LAA reshaper, is used to fasten the LAA. In some embodiments, the fastener is used to fasten a portion of the LAA evaginated and/or onto the LAA reshaper. In some embodiments, during fastening, the fastener is decoupled from the LAA reshaper.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Process for Invagination of a Body Cavity

According to some exemplary embodiments, a body cavity closure device is configured to close a body cavity, for example to prevent entrance of blood into the blood cavity and/or exit of blood clots or other floating particles from the body cavity into the blood stream. Reference is now made to FIG. 1, depicting a general process for closure of a body cavity, for example the LAA, according to some exemplary embodiments of the invention.

According to some exemplary embodiments, a body cavity closure device is aligned with an opening of a body cavity, for example with the LAA opening at block 102. In some embodiments, a guiding instrument of the body cavity closure device, for example a catheter, is aligned with the LAA opening. In some embodiments, the catheter is inserted, for example transseptally inserted, into the LA. In some embodiments, an LAA reshaper is advanced from a distal opening of a working channel of the catheter and is anchored at least partly within the LAA. In some embodiments, the LAA reshaper is connected to the catheter by an elongated LAA reshaper guide. Alternatively, the LAA reshaper is an expandable section, for example a distal expandable section of the LAA reshaper guide. In some embodiments, anchoring the catheter to the LAA allows, for example to advance one or more tools, for example tissue manipulating tool, towards the LAA opening in the LA and/or into the LAA.

According to some exemplary embodiments, vacuum is applied on the body cavity, for example on the LAA, at block 104. In some embodiments, vacuum is applied on the LAA cavity from outside the LAA cavity. Alternatively, vacuum is applied on the LAA cavity, at least partly from within the cavity. In some embodiments, a vacuum inlet is advanced towards the LAA from the catheter, for example along the LAA reshaper guide. In some embodiments, the vacuum inlet comprises an expandable vacuum inlet configured to expand from the working channel of the catheter. In some embodiments, the vacuum inlet is attached to the LA wall around the LAA opening. In some embodiments, the vacuum inlet applies vacuum on the LAA, for example to attach at least a portion of the vacuum inlet to the LA wall around the LAA opening. Alternatively or additionally, vacuum is applied by the vacuum inlet to invaginate at least a portion of the LAA either within the LAA or into the LA.

According to some exemplary embodiments, at least a portion of the body cavity, for example the LAA, is invaginated at block 106. In some embodiments, the LAA is at least partly invaginated into the LA. Alternatively, the LAA is completely invaginated into the LA. In some embodiments, two or more portions of the LAA are invaginated into the LA, for example 2 portions, 3 portions, 4 portions, 5 portions of the LAA are invaginated into the LA. In some embodiments, at least a portion of the LAA is invaginated by applying vacuum from outside of the LAA or at least partly from within the LAA. In some embodiments, vacuum is selectively applied to invaginate specific portions of the LAA.

According to some exemplary embodiments, the body cavity, for example the LAA, is reshaped during invagination and/or vacuum application at block 108. In some embodiments, the LAA is reshaped by inducing the collapse of selected portions of the LAA, for example applying vacuum on some LAA portions while supporting other portions of the LAA. Alternatively or additionally, the LAA is reshaped by invaginating selected portions of the LAA into the LA, for example as described at block 106.

According to some exemplary embodiments, two or more invaginated portions of the body cavity are fastened at block 110. In some embodiments, two or more invaginated portions of the LAA are fastened within the LA, for example by placing a tissue ligator, for example a tissue fastener, comprising a loop-shaped ligator or a band ligator around some or all of the invaginated portions.

Exemplary Device for Invagination of a Body Cavity

Figure 2A:
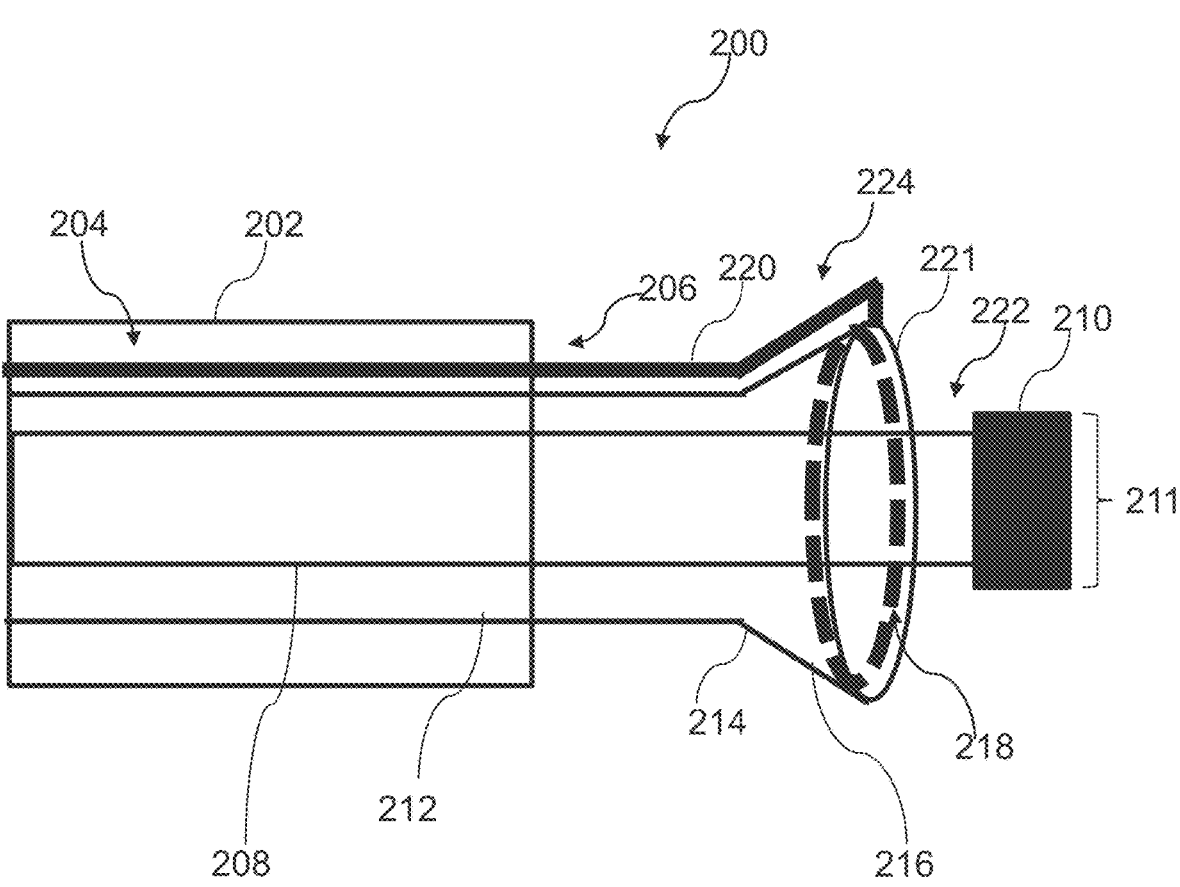
FIGS. 2A and 2B are block diagrams of a device for closure of a body cavity, according to some exemplary embodiments of the invention.

According to some exemplary embodiments, a device for invagination of a body cavity, for example the LAA, is thin and flexible enough to allow navigation of the device to remote organs through blood vessels. Reference is now made to FIG. 2A, depicting a body cavity closure device, according to some exemplary embodiments of the invention.

According to some exemplary embodiments, a device for invagination of a body cavity, for example device 200 comprises an elongated catheter 202 having an internal working channel 204 and a distal opening 206 of the working channel. In some embodiment a distal opening of the catheter is an opening facing the body cavity or an opening that is positioned in a close proximity to the body cavity opening. In some embodiments, one or more proximal openings positioned at a distance from the body cavity are located outside the body. In some embodiments, the distal opening 206 has a maximal width in a range of 1-20 mm, for example 1-10 mm, 5-15 mm, 12-20 mm or any intermediate, smaller or larger range of values.

According to some exemplary embodiments, the elongated catheter, for example elongated catheter 202 has an outer diameter in a range of 1-20 mm, for example 1-10 mm, 5-15 mm, 12-20 mm or any intermediate, smaller or larger range of values. In some embodiments, a thickness of a wall of the elongated catheter, for example elongated catheter 202, is in a range of 0.5-1.5 mm, for example 0.5-1.2 mm, 0.9-1.5 mm or any intermediate, smaller or larger range of values.

According to some exemplary embodiments, the catheter is shaped and sized to be introduced into the left atria (LA), for example transseptally introduced into the LA. In some embodiments, a width of the catheter 202 is smaller than 24 mm, for example smaller than 20 mm, smaller than 15 mm or any intermediate, smaller or larger width. In some embodiments, a width of the catheter, for example an external width of the catheter is smaller than 30 French, for example smaller than 20 French, smaller than 10 French, smaller than 7 French or any intermediate, smaller or larger value. In some embodiments, the width of the catheter is smaller than 24 mm, for example to allow introduction of the catheter via the superior or inferior vena cava into the right atria (RA). In some embodiments, a width of a catheter portion that is transseptally introduced into the LA is in a range of 6-30 French, for example 6-15 French, 10-20 French, 19-30 French or any intermediate, smaller or larger value.

According to some exemplary embodiments, the device 200 comprises an elongated LAA reshaper guide 208 having an LAA reshaper 210 at a distal end of the 222 of the guide 208. In some embodiments, the elongated guide 208 is shaped and sized to pass within the catheter 202, for example within the working channel 204 of the catheter 202. In some embodiments, the elongated guide is extendable from the distal opening 206 of the working channel 204. In some embodiments, the elongated guide is at least partially elastic and/or bendable, for example to allow the passage of the elongated guide 208 within the catheter 202 when the catheter is bended inside the body, for example inside blood vessels.

According to some exemplary embodiments, the LAA reshaper 210 is shaped and sized to be introduced into the LAA. In some embodiments, the LAA guide 208 and the LAA reshaper 210 are forwardly extended from the distal opening 206 into the LA and into the LAA. In some embodiments, the LAA reshaper 210 is expandable. In some embodiments, the LAA reshaper 210 moves between a collapsed state, for example when the LAA reshaper is within the working channel 204 of the catheter 202, and an expanded state, for example within the LAA. In some embodiments, in a collapsed state, a width 211 of the LAA reshaper is smaller than a width of the LAA opening, for example to allow at least a partial insertion of the LAA reshaper 210 into the LAA cavity. In some embodiments, a maximal width of the LAA reshaper, for example LAA reshaper 210, in a collapsed state is in a range of 1-30 mm, for example in a range of 1-10 mm 5-15 mm, 10-20 mm, 18-30 mm or any intermediate, smaller or larger range of values. In some embodiments, a maximal width of the LAA reshaper, for example LAA reshaper 210, in an expanded state is in a range of 5-50 mm, for example 5-15 mm, 10-25 mm, 20-35 mm, 30-50 mm, or any intermediate, smaller or larger range of values.

Figure 2B:
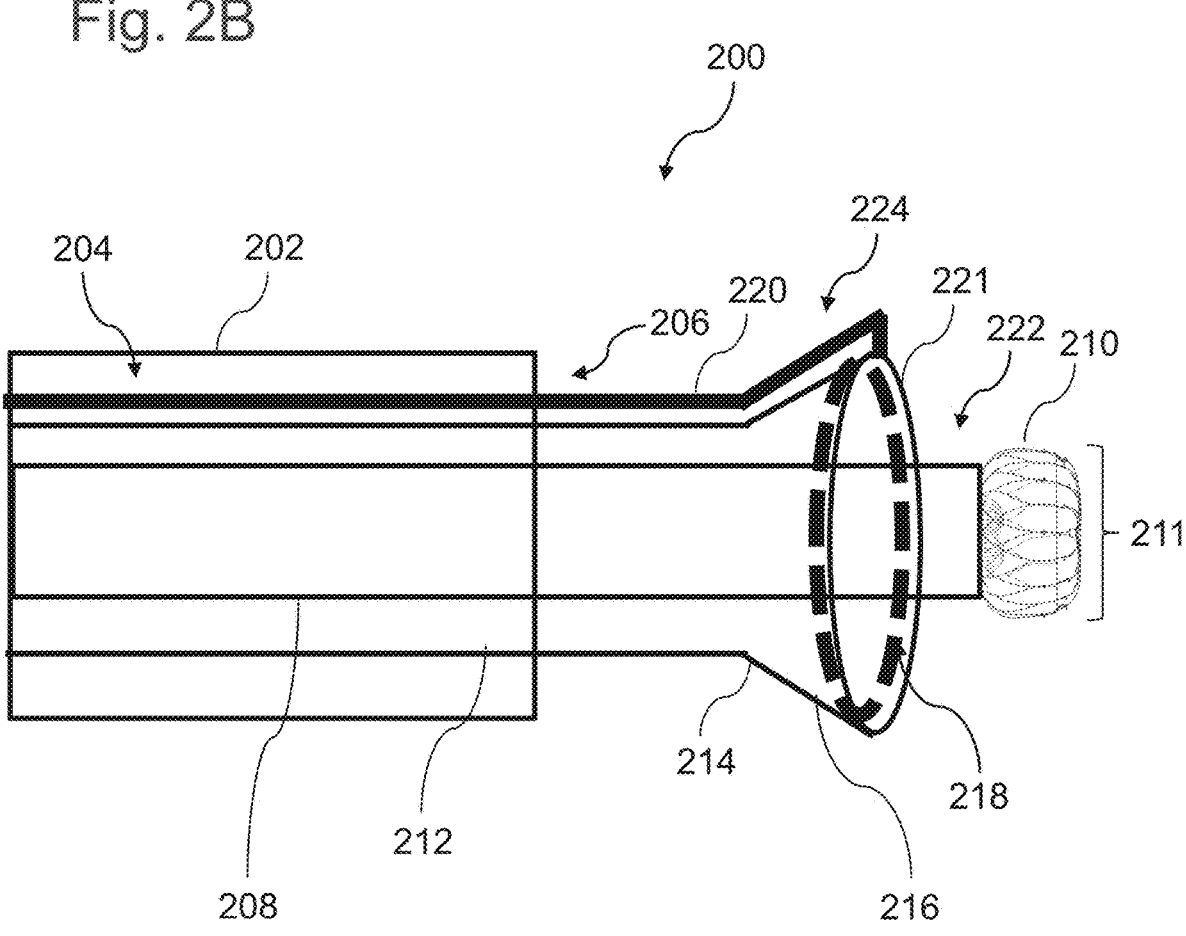

According to some exemplary embodiments, the expandable LAA reshaper is formed from a mesh of wires, configured to expand, upon forwardly extending from the distal opening 206 of the working channel, for example within the LAA. In some embodiments, the LAA reshaper expands within the LAA and applies pressure, for example radial pressure against the LAA wall. In some embodiments, for example as shown in FIG. 2B, the device, for example the device 200 is configured to utilize the WATCHMAN™ device as a reshaper, for example the LAA reshaper 210. In some embodiments, the expandable LAA reshaper has a cylindrical shape with an inner lumen. In some embodiments, a distal opening of the LAA reshaper in an expanded state is closed. Alternatively, the distal opening of the LAA reshaper in an expanded state is open. In some embodiments, the LAA reshaper is formed at least partly from a shape memory alloy, for example Nitinol. According to some exemplary embodiments, the LAA reshaper, for example LAA reshaper 210, comprises one or more anchors configured to anchor the LAA reshaper in an expanded state to the LAA wall. In some embodiments, when the LAA reshaper is in a collapsed state, the anchors are folded, for example to prevent damage to the LAA reshaper. In some embodiments, when the LAA reshaper expands, the one or more anchors unfold and optionally face the LAA wall. In some embodiments, the one or more anchors comprise at least one hook, and/or at least one pin.

According to some exemplary embodiments, the expandable LAA reshaper comprises an inflatable balloon, which is configured to inflate within the LAA, for example to apply force against the LAA wall. In some embodiments, the LAA reshaper guide comprises an inflation channel, configured to inflate the LAA reshaper by fluid, for example liquid or gas.

According to some exemplary embodiments, the LAA reshaper 210, for example an expandable LAA reshaper, comprises one of more anchors configured to reversibly anchor the LAA reshaper to the LAA wall inside the LAA. In some embodiments, the one or more anchors are hidden or folded anchors, configured to be hidden or folded within the catheter and to reveal or unfold when the LAA reshaper is located within the LAA.

According to some exemplary embodiments, the device 200 comprises an elongated suction channel 212 shaped and sized to pass within the working channel 204 of the catheter 202. In some embodiments, the diameter or the width of the suction channel 212 is smaller than the internal width or internal diameter of the working channel 204. In some embodiments, the elongated suction channel 212 terminates with vacuum inlet 216 at a distal end of the suction channel 212 facing the LAA. In some embodiments, the vacuum inlet 216 comprises an expandable inlet configured to be in a collapsed state within the working channel 204, and to expand within the LA and/or when exiting from the distal opening 206 of the working channel 204.

According to some exemplary embodiments, the vacuum inlet 216 is at least partly elastic, for example to allow attachment of the vacuum inlet 216, for example attachment of one or more lips surrounding an opening of the vacuum inlet 216, to the LAA wall. In some embodiments, the one or more lips of the vacuum inlet 216 are at least partly elastic. In some embodiments, the vacuum inlet 216 is at least partly elastic, for example at least partly reversibly deformable, to allow attachment of the vacuum inlet 216 to the LA wall around the LAA opening.

According to some exemplary embodiments, a width, for example a maximal width, of the vacuum inlet is larger than the maximal width of the LAA opening, for example to allow attachment of the vacuum inlet to the LA wall and around the LAA opening. In some embodiments, a maximal width is a maximal width of the vacuum inlet when the vacuum inlet is in a fully expanded state. In some embodiments, a maximal width of the vacuum inlet is larger than the width of the catheter 202. In some embodiments, a maximal width of the vacuum inlet 216 is in a range of 10-50 mm, for example 10-20 mm, 15-30 mm, 25-40 mm, 35-50 mm, or any intermediate, smaller or larger range of values.

According to some exemplary embodiments, the vacuum inlet 216 in an expanded state has a narrow proximal section 214 connected to the suction channel 212, and a wider forwardly facing distal section 221. In some embodiments, the maximal width or diameter of the wider distal section 221 is larger than the maximal width of the LAA opening. Additionally, the maximal width or diameter of the wider distal section 221 is larger than the distal opening 206 of the catheter 202 and/or the width of the catheter 202. In some embodiments, a maximal width of the wider distal section 221 is in a range of 10-50 mm, for example 10-20 mm, 15-30 mm, 25-40 mm, 35-50 mm, or any intermediate, smaller or larger range of values.

According to some exemplary embodiments, a distal end of the vacuum inlet, for example an edge of the vacuum inlet surrounding a wide distal opening of the vacuum inlet is configured to be attached to the LA around the LAA opening at a distance in a range of 1-15 mm, for example 1-7 mm, 5-10 mm, 8-15 mm from the LAA opening. In some embodiments, the vacuum inlet, for example a frame of the vacuum inlet is formed from one or more of Nitinol, stainless steel, Silicone, Polyurethane and/or rubber. In some embodiments, the frame of the vacuum inlet is covered with a medical-grade coating, for example Silicon or other sealed fabrics. In some embodiments, an inner surface of the coating comprises bulges or bumps, for example to increase friction with tissue.

According to some exemplary embodiments, the device, for example the vacuum inlet comprises one or more sensors, configured to sense the amount of invaginated tissue, for example by measuring electrical properties of the invaginated tissue. In some embodiments, the electrical properties comprise one or both of impedance and conductivity. Alternatively or additionally, the one or more sensors comprise pressure sensor, configured to sense contact with the LA wall or LAA wall. Alternatively or additionally, the one or more sensors are configured to sense at least one parameter related to electrical conductivity, for example to check that the invagination process did not damage heart electrical conductivity. In some embodiments, the body cavity closure device comprises at least one vacuum sensor, for example to sense the levels of vacuum applied through the suction channel and/or through the vacuum inlet on the tissue, for example on the LAA tissue. In some embodiments, the one or more sensors are configured to sense electrical properties of the LA, for example to sense contact of the vacuum inlet with the LA wall.

According to some exemplary embodiments, the device comprises one or more pressure sensors configured to sense pressure applied for example by the LAA reshaper on the LAA tissue and/or pressure applied by the vacuum inlet on a wall of the LA around the LAA opening.

According to some exemplary embodiments, one or more electrodes of the device, for example electrodes coupled to the vacuum inlet, are configured to sense electrical properties of the tissue, for example impedance, before, during and/or after the invagination process. In some embodiments, a control circuitry connected to the one or more electrodes measures the conductivity and/or changes in conductivity of the heart based on the sensed electrical properties According to some exemplary embodiments, the vacuum inlet has a symmetric or an asymmetric shape. In some embodiments, the shape and size of the vacuum inlet varies, for example by contracting portion of the vacuum inlet by the catheter, for example catheter 202. In some embodiments, the shape and/or size of the vacuum inlet in an expanded state varies when the vacuum inlet portions are introduced into the inner lumen of the catheter, for example catheter 202.

According to some exemplary embodiments, the LAA reshaper guide 208 and the LAA reshaper 210 are shaped and sized to pass within the suction channel 212. In some embodiments, a width or a diameter of the guide 208 is smaller than the width or diameter of the suction channel. In some embodiments, a maximal width of the LAA reshaper 210, for example in a collapsed state, is smaller than a width of the suction channel. In some embodiments, the maximal width or the diameter of the suction channel is in a range of 1-15 mm, for example 1-7 mm, 5-12 mm, 10-15 mm, or any intermediate, smaller or larger range of values.

According to some exemplary embodiments, the device 200 comprises a tissue ligator, for example fastener 224. In some embodiments, the ligator comprises a loop-shaped ligator, for example a band ligator. In some embodiments, the ligator, for example fastener 224, is configured to fasten one or more invaginated portions of the LAA. In some embodiments, the fastener 224 is shaped and sized to be fastened around the one or more invaginated portions of the LAA. Additionally, the fastener 224 is configured to be tightened around the one or more invaginated portions of the LAA. In some embodiments, tightening of the fastener around two or more invaginated portions of the LAA closes the LAA opening and/or any other flow path between the LA and the LAA.

According to some exemplary embodiments, the fastener 224 comprises a fastener loop 218 and a fastener manipulator 220 connected to the fastener loop 218. In some embodiments, the fastener loop 218 is elastic, foldable and/or collapsible to be positioned within a working channel 204 of the catheter 202. Additionally, the fastener manipulator is thin and/or has a transverse cross-section which is smaller than a width of the working channel 204.

According to some exemplary embodiments, the fastener loop 218 in an open state has a width or a diameter which is larger than the maximal width of the one or more invaginated portions of the LAA. In some embodiments, the maximal width or maximal diameter of the fastener loop 218 in an open state is in a range of 10-50 mm, for example 10-20 mm, 15-30 mm, 25-40 mm, 35-50 mm, or any intermediate, smaller or larger range of values. In some embodiments, the fastener loop 218 in an open state has a width which is larger than a maximal width of the vacuum inlet 216, for example to allow passing of the fastener over the vacuum inlet. Alternatively, the fastener loop 218 in an open state has a width which is smaller than the maximal width of the vacuum inlet 216, for example to allow fastening of one or more invaginated portions of the LAA from within the vacuum inlet 216.

According to some exemplary embodiments, the fastener loop 218, for example in an open state, is connected to the distal section 221 of the vacuum inlet 216. In some embodiments, the fastener loop 218, for example in an open state, is positioned within the vacuum inlet 216. Alternatively, the fastener loop 218 is positioned outside the vacuum inlet 216. In some embodiments, the fastener loop 218 comprises a wire and/or a string. In some embodiments, the fastener loop 218 comprises a mesh, for example a mesh of wires.

According to some exemplary embodiments, the fastener manipulator 220 is shaped and sized to be positioned within the working channel 204 and outside the suction channel 212. Alternatively, the fastener manipulator 220 is shaped and sized to be positioned within the suction channel 212. In some embodiments, the fastener manipulator 220 is rigid enough to be moved, for example retracted and/or forwardly advanced, from outside the body. In some embodiments, moving the fastener manipulator 220 from outside the body opens and/or fastens the fastener, for example fastener loop 218.

According to some exemplary embodiments, the fastener loop is coupled to the vacuum inlet by one or more of hooks, wires, elastic wires, cords, and/or elastic cords. In some embodiments, the fastener loop is made from ePTFE, polypropylene, peek, and/or polyurethane. In some embodiments, the fastener loop has a thickness in a range of 0.1-2 mm, for example 0.1-0.8 mm, 0.5-1.5 mm, 1.2-2 mm or any intermediate, smaller or larger range of values. In some embodiments, the external surface of the fastener, for example the fastener loop, is covered with one or more of bumps, bulges and protrusions, for example to allow improved contact and/or friction between the fastener loop and the tissue. Optionally, the one or more of bumps, bulges and protrusions are formed from a hardened material. In some embodiments, the one or more of bumps, bulges and protrusions are positioned on the external surface of a sleeve covering the fastener loop.

According to some exemplary embodiments, the force applied by the fastener loop on the LAA tissue is up to 35 Newtons (N), for example up to 25N, up to 20N, up to 15N, up to 10N or any intermediate, smaller or larger value.

According to some exemplary embodiments, one or more of: the catheter, for example catheter 202, the LAA reshaper guide, for example LAA reshaper guide 208, the LAA reshaper, for example LAA reshaper 210, the suction channel, for example the suction channel 212, the vacuum inlet, for example vacuum inlet 216, the fastener manipulator, for example fastener manipulator 220, the fastener, for example fastener loop 218, are coated or comprise at least partially one or more radiopaque materials, configured to increase x-ray detection. In some embodiments, the one or more radiopaque materials comprise one or more of barium sulfate, bismuth compounds, tungsten or any other material, for example metal that absorbs x-rays.

Alternatively or additionally, the one or more of: the catheter, for example catheter 202, the LAA reshaper guide, for example LAA reshaper guide 208, the LAA reshaper, for example LAA reshaper 210, the suction channel, for example the suction channel 212, the vacuum inlet, for example vacuum inlet 216, the fastener manipulator, for example fastener manipulator 220, the fastener, for example fastener loop 218, are coated or comprise at least partially one or more hyperechoic materials, for example metal, plastic or any other material that increases ultrasound detection.

Exemplary Detailed Process for Closure of the LAA

Figure 3:
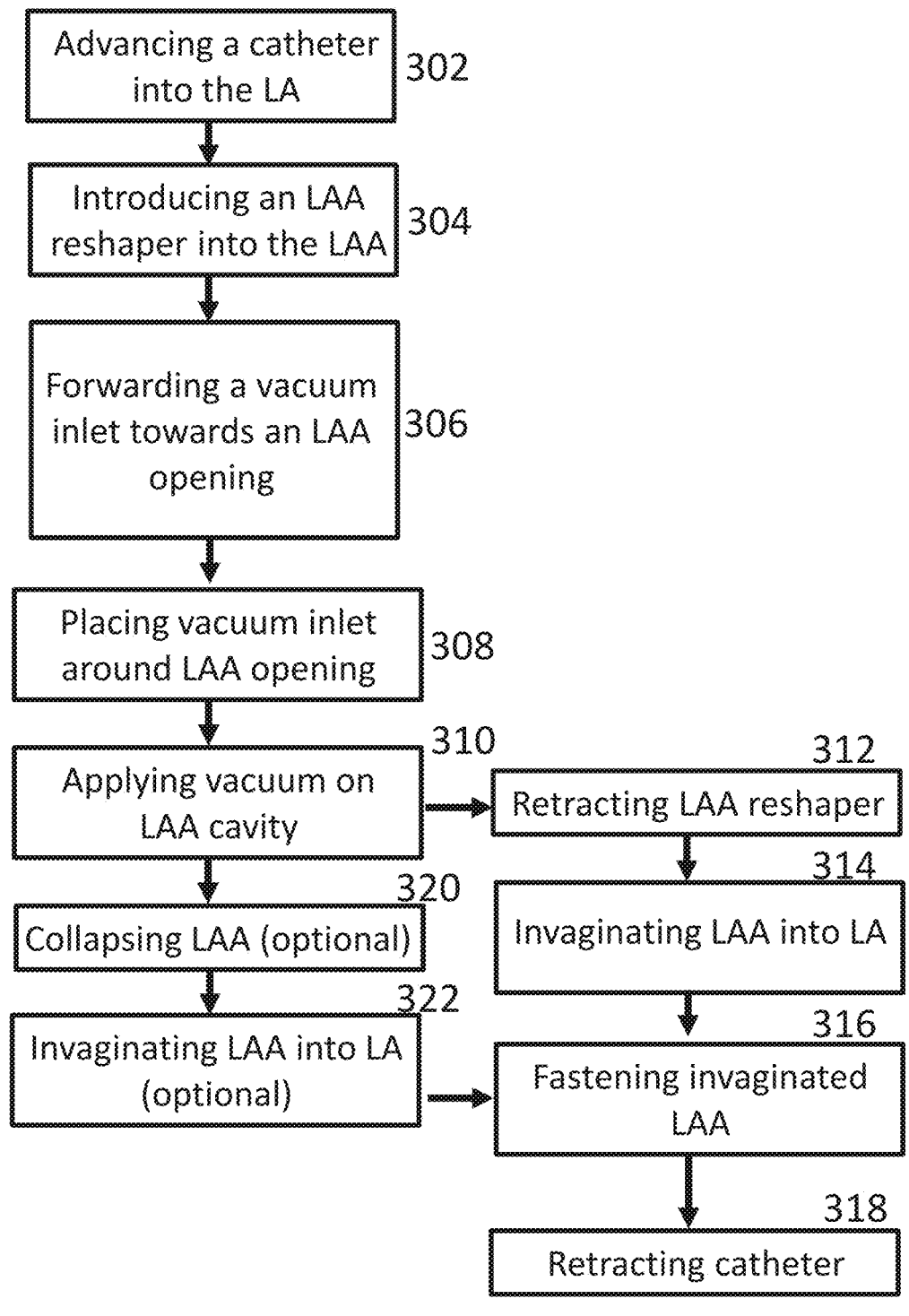
FIG. 3 is a detailed flow chart for closure of the LAA, according to some exemplary embodiments of the invention.

According to some exemplary embodiments, the LAA is closed, for example to prevent blood flow from the LA into the LAA, and to prevent formation and release of blood clots from the LAA cavity into the LA and into the blood stream. In some embodiments, the LAA is closed by a device, for example device 200 shown in FIGS. 2A-B, that is navigated into the LA, for example by penetrating through the septum into the LA from the RA. Reference is now made to FIG. 3 depicting a detailed process for closure of the LAA, according to some exemplary embodiments of the invention.

According to some exemplary embodiments, a catheter, for example catheter 202 shown in FIGS. 2A-B, of a closure device is advanced into the LA at block 302. In some embodiments, the catheter is navigated into the RA, for example via the superior vena cava or the inferior vena cava. In some embodiments, the catheter is transeptally introduced into the LA through the septum.

According to some exemplary embodiments, an LAA reshaper, for example LAA reshaper 210 shown in FIGS. 2A-B, is advanced through the LAA opening at least partly into the LAA, at block 304. In some embodiments, the LAA reshaper is anchored within the LAA. In some embodiments, the LAA reshaper is expanded within the LAA, for example to contact the LAA wall within the LAA with sufficient force to anchor the LAA reshaper.

According to some exemplary embodiments, a suction channel terminating with a vacuum inlet is forwarded towards the LAA opening at block 306. In some embodiments, the vacuum inlet exits through a distal opening of the catheter and expands within the LA. Alternatively or additionally, the vacuum inlet expands when reaching the LAA opening. In some embodiments, the expansion of the vacuum inlet is controlled from outside the body.

According to some exemplary embodiments, the vacuum inlet, is placed over the LAA opening. In some embodiments, the vacuum inlet is attached to the LA wall, around the LAA opening. In some embodiments, lips of a distal section of the vacuum inlet are attached to the LA wall around the LAA opening. In some embodiments, the vacuum inlet is attached to the LA wall while applying vacuum, for example low pressure vacuum. In some embodiments, vacuum, for example low pressure vacuum, is applied in order to firmly attach the vacuum inlet to the LA wall.

In some embodiments, low pressure vacuum is in a range of 0-500 mmHg, for example 0-200 mmHg, 150-350 mmHg, 300-450 mmHg, 380-500 mmHg or any intermediate, smaller or larger range of values.

According to some exemplary embodiments, vacuum is applied through the vacuum inlet on the LAA cavity at block 310. In some embodiments, high pressure vacuum is applied on the LAA cavity. In some embodiments, a high pressure vacuum is in a range of 400-900 mmHg, for example 400-600 mmHg, 550-800 mmHg, 650-900 mmHg or any intermediate, smaller or larger range of values. In some embodiments, the high pressure vacuum is applied with a pressure value sufficient to invaginate one or more, for example two, three, four or any number of portions of the LAA, at least partly into the LA. Alternatively or additionally, vacuum is applied in order to prevent the release of floating material, for example blood clots and/or debris from the LAA into the LA.

According to some exemplary embodiments, the LAA reshaper is retracted at block 312. In some embodiments, the LAA reshaper is retracted while vacuum is applied on the LAA, for example as described at block 310. In some embodiments, the LAA reshaper is retracted into the LA while applying force to the LAA wall. Alternatively or additionally, the LAA reshaper is retracted into the LA while being in contact with the LAA wall.

According to some exemplary embodiments, the LAA is at least partly invaginated at block 314. In some embodiments, the LAA is at least partly invaginated into the LA. In some embodiments, one or more portions of the LAA, for example 2, 3, 4, 5 or any number of LAA portions are invaginated into the LA. In some embodiments, the LAA is invaginated into the LA using the vacuum applied on the LAA cavity and the retraction of the LAA reshaper into the LA. Optionally, the LAA is invaginated into the LA using only the retraction of the LAA reshaper, where the applied vacuum is used to remove floating particles during LAA manipulation.

According to some exemplary embodiments, the LAA is collapsed at block 320. In some embodiments, the vacuum applied on the LAA cavity induces the collapse, for example internal collapse of one or more sections of the LAA. In some embodiments, the one or more collapsed sections are sections that are not supported by an LAA reshaper positioned within the LAA cavity. Optionally, the LAA reshaper prevents collapse of LAA sections that are placed in contact with the LAA reshaper.

According to some exemplary embodiments, for example when the LAA reshaper is placed at least partly within the LAA and is not in contact with the LAA, the collapsed sections collapse on the LAA reshaper. In some embodiments, vacuum applied through the LAA reshaper on the LAA wall induces the collapse of LAA sections on the LAA reshaper.

According to some exemplary embodiments, the LAA is invaginated at least partly into the LA at block 322. In some embodiments, the vacuum applied on the LAA cavity induces the invagination of one or more portions, for example 2, 3, 4 or any number of LAA portions into the LA. In some embodiments, the collapsed sections of the LAA, for example as described at block 320, are invaginated at least partly into the LA. In some embodiments, LAA collapsing on the LAA reshaper positions one or more portions of the LA at least partly within the LA.

According to some exemplary embodiments, the invaginated LAA is fastened at block 316. In some embodiments, the one or more invaginated portions of the LAA are fastened at block 316. In some embodiments, the LAA is fastened by placing a fastener, for example a fastener loop 218 of fastener 224 around one or more, for example 2, 3, 4 or any number of invaginated portions. In some embodiments, the LAA is closed by the fastening of the invaginated portions of the LAA. Alternatively or additionally, the LAA opening in the LA is closed by the fastening of the invaginated LAA portions.

According to some exemplary embodiments, once the LAA is invaginated into the LA and/or is fastened, the LAA reshaper is retracted into the working channel of the catheter. In some embodiments, the LAA reshaper is collapsed into the working channel of the catheter or into the suction channel, for example suction channel 212 shown in FIGS. 2A-B.

According to some exemplary embodiments, the catheter is retracted at block 318. In some embodiments, once the invaginated portions of the LAA are fastened, the vacuum inlet is retracted into the working channel of the catheter. Additionally, the vacuum inlet is collapsed or folded into the working channel of the catheter. In some embodiments, the catheter is retracted out from the LA and the body at block 318.

Exemplary Aligning of a Catheter and Closure of a Body Cavity

According to some exemplary embodiments, a catheter is aligned with an opening of a body cavity, for example the LAA opening prior to body cavity manipulation, for example closure of the body cavity and/or the body cavity opening. Reference is now made to FIGS. 4A-4F depicting aligning of a catheter of a body cavity closure device with a body cavity opening and closure of the body cavity, according to some exemplary embodiments of the invention.

Figure 4A:
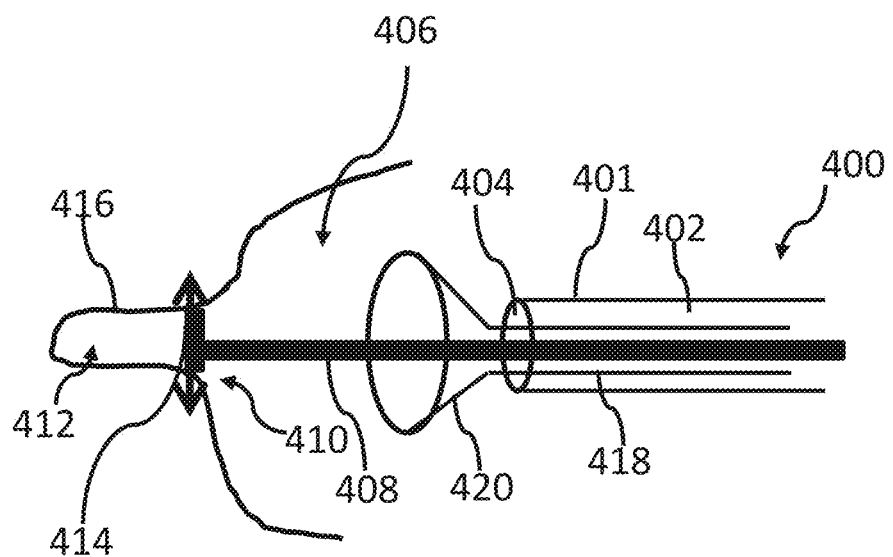
FIG. 4A is a schematic illustration of alignment of a body cavity closure device with a body cavity, according to some exemplary embodiments of the invention.

According to some exemplary embodiments, for example as shown in FIG. 4A, a catheter 401 of a body cavity closure device 400 is navigated into the body cavity, for example the LA 406. In some embodiments, an LAA reshaper 414 is forwardly advanced from the working channel 402 of the catheter 401 at least partly into the LAA cavity 412. Optionally, the LAA reshaper is forwardly advanced from a suction channel 418 positioned within the working channel 402.

According to some exemplary embodiments, the LAA reshaper 414 is anchored within the LAA cavity 412, for example by contacting the wall 416 of the LAA cavity 412. In some embodiments, the LAA reshaper 414 expands within the LAA cavity 412. In some embodiments, expansion of the LAA reshaper 414 within the LAA cavity 412 pushes the external surface of the LAA reshaper against the wall 416 of the LAA cavity 412 with forces that are sufficient to anchor the LAA reshaper without tearing or damaging the wall 416.

According to some exemplary embodiments, a vacuum inlet 420, for example a cone-shaped vacuum inlet or a concave-shaped vacuum inlet, positioned at a distal end of the suction channel 418 expands when exiting from the working channel 402 of the catheter 401. In some embodiments, the expanded vacuum inlet 420 is advanced along an LAA reshaper guide 408 connecting the anchored LAA reshaper 414 and the catheter 401, towards the LAA opening 410. Optionally, the catheter 401 is advanced along the guide 408 towards the LAA opening.

Figure 4B:
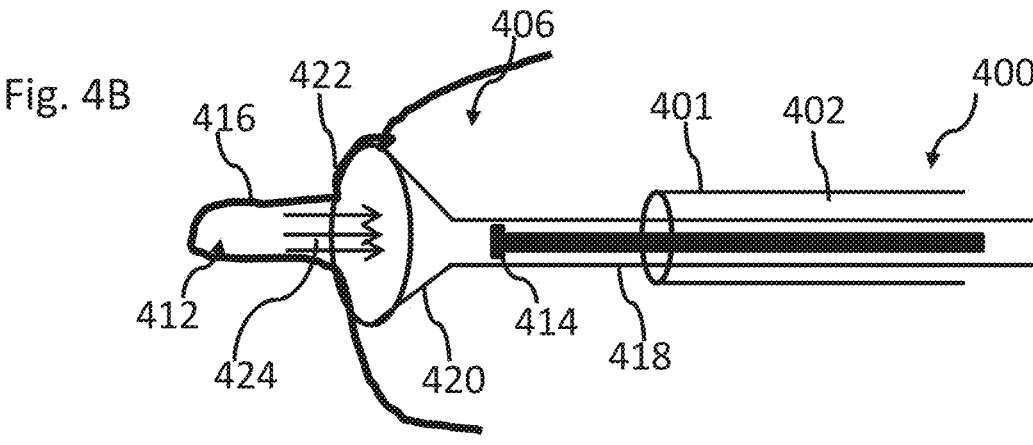
FIGS. 4B-4F are schematic illustrations of LAA invagination, according to some exemplary embodiments of the invention.

According to some exemplary embodiments, for example as shown in FIG. 4B, the vacuum inlet 420 is placed in contact with the LA wall 422 surrounding the LAA opening 410. In some embodiments, one or more lips of the vacuum inlet 420, facing the LA wall, are pushed against the LA wall. In some embodiments, vacuum 424, for example low pressure vacuum, is applied during the attachment of the vacuum inlet 420 to the LA wall 422, for example to ensure tight interaction between the LA wall and the vacuum inlet 420. In some embodiments, once the vacuum inlet is in contact with the LA wall 422, the LAA reshaper 414 is released from the LAA cavity and retracted back into the working channel 402 of the catheter 401. Optionally, the LAA reshaper 414 is retracted into the suction channel 418. In some embodiments, the LAA reshaper 414 collapses when retracting into the working channel 402 or into the suction channel 418. In some embodiments, when low pressure vacuum and/or high pressure vacuum is applied through the vacuum inlet 420 on the LAA, blood clots in the LAA are sucked and removed from the LAA into the suction channel 418.

Figure 4C:
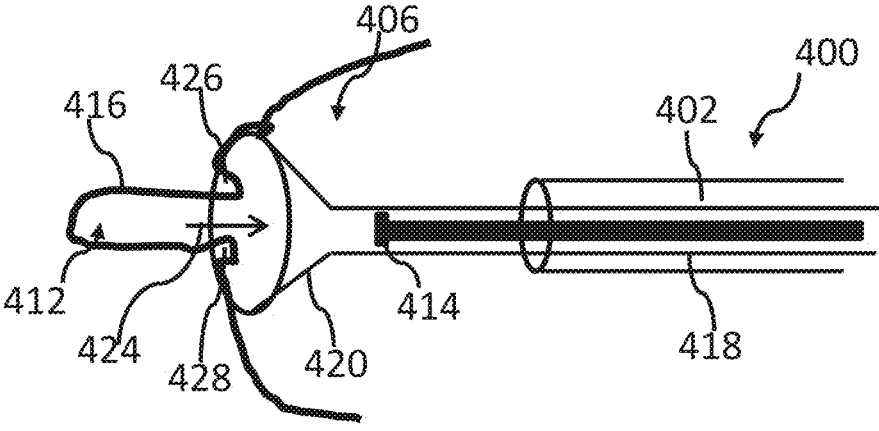

According to some exemplary embodiments, for example as shown in FIG. 4C, vacuum, for example high pressure vacuum, is applied from the vacuum inlet 420 on the LAA, for example on the LAA cavity 412. In some embodiments, the high pressure vacuum invaginates two or more portions of the LAA, for example portions 426 and 428, into the LA 406. In some embodiments, the two or more portions are invaginated into the vacuum inlet 420.

Figure 4D:
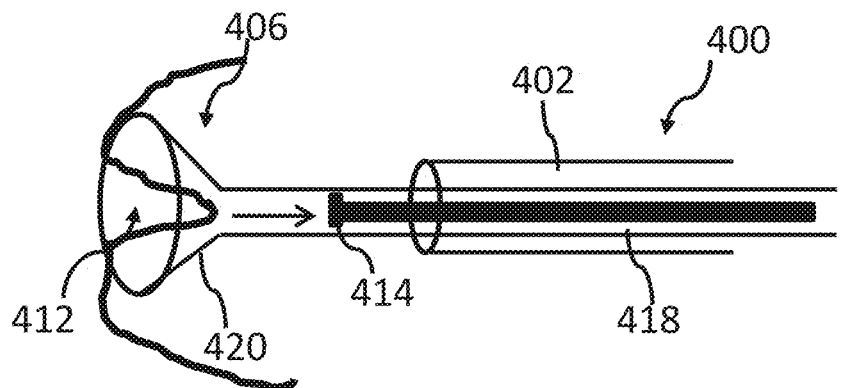

Alternatively and according to some exemplary embodiments, for example as shown in FIG. 4D, the LAA 412 is completely invaginated into the LA 406. In some embodiments, the LAA 412 is completely invaginated into the vacuum inlet 420. In some embodiments, the LAA 412 is completely invaginated by the application of high pressure vacuum.

Figure 4E:
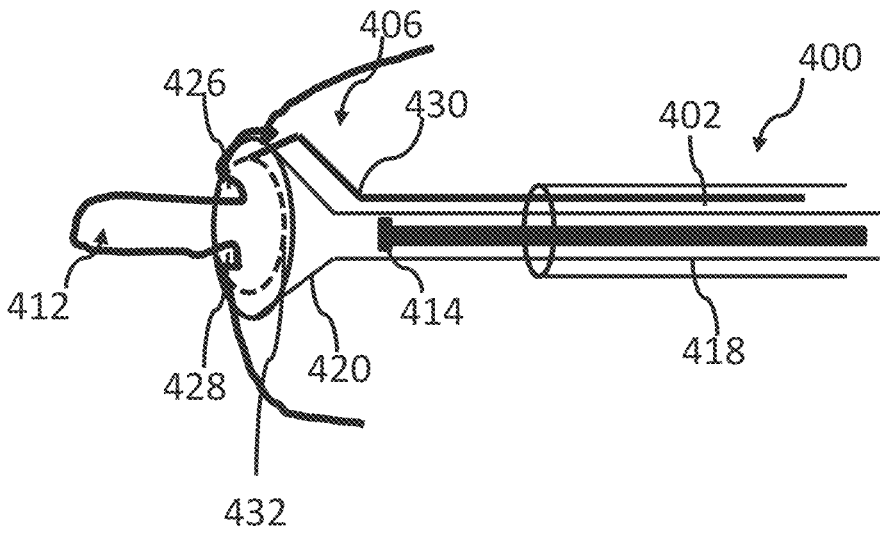

According to some exemplary embodiments, for example as shown in FIG. 4E, a fastener, for example a fastener loop 432, is positioned around the two or more invaginated portions of the LAA 412, for example portions 426 and 428. In some embodiments, the fastener loop 432 is coupled to the inner surface of the vacuum inlet 420. Alternatively, the fastener loop 432 is coupled to the outer surface of the vacuum inlet 420.

According to some exemplary embodiments, the fastener loop 432 is mechanically connected to a fastener manipulator 430. In some embodiments, the fastener manipulator is located outside the vacuum inlet 420. In some embodiments, the fastener manipulator 430 comprises an elongated fastener manipulator which is shaped and sized to be advanced into the LA 406 from within the working channel 402 of the catheter. In some embodiments, the fastener manipulator, for example fastener manipulator 430, is shaped and sized to be advanced into the LA 406 from within the suction channel 418. Optionally, the fastener manipulator 430 is at least partly rigid to allow manipulation of the fastener loop 432 from outside the body. In some embodiments, retraction or advancement of the fastener manipulator 430 fastens the fastener loop 432 around the two or more invaginated portions of the LAA. Alternatively, rotation of the fastener manipulator 430 fastens the fastener loop 432 around the two or more invaginated portions of the LAA.

Figure 4F:
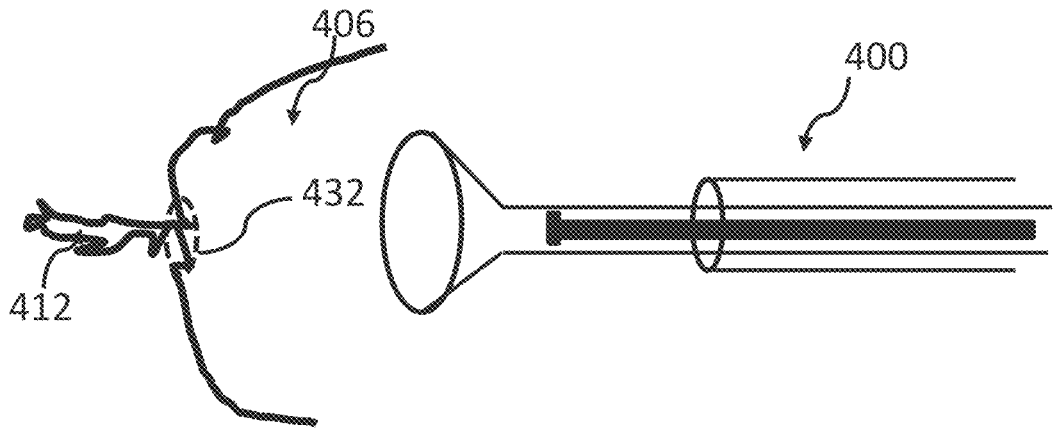

According to some exemplary embodiments, for example as shown in FIG. 4F, once the invaginated portions of the LAA are fastened within the LA, the device 400 is retracted from the LA. In some embodiments, up to 50% of the LAA tissue, for example up to 30%, up to 10%, up to 5% or any intermediate, smaller or larger percentage of LAA tissue is positioned within the LA following the invagination and fastening. In some embodiments, the LAA portion that was not invaginated, collapses. In some embodiments, fastening of the invaginated portions of the LAA closes the LAA opening. Additionally, fastening of the invaginated LAA portions isolates the LAA 412 from the LA 406.

Exemplary LAA Reshaping During Vacuum Application

According to some exemplary embodiments, the LAA reshaper is positioned within the LAA and regulates the flow of suction forces within the LAA cavity, for example to invaginate specific regions of the LAA. Alternatively or additionally, the LAA reshaper maintains an open flow path into the LAA, for example by preventing the collapse of selected regions of the LAA during vacuum application. Reference is now made to FIGS. 5A-5E depicting regulation of suction forces and/or LAA collapse during vacuum application, according to some exemplary embodiments of the invention.

Figure 5A:
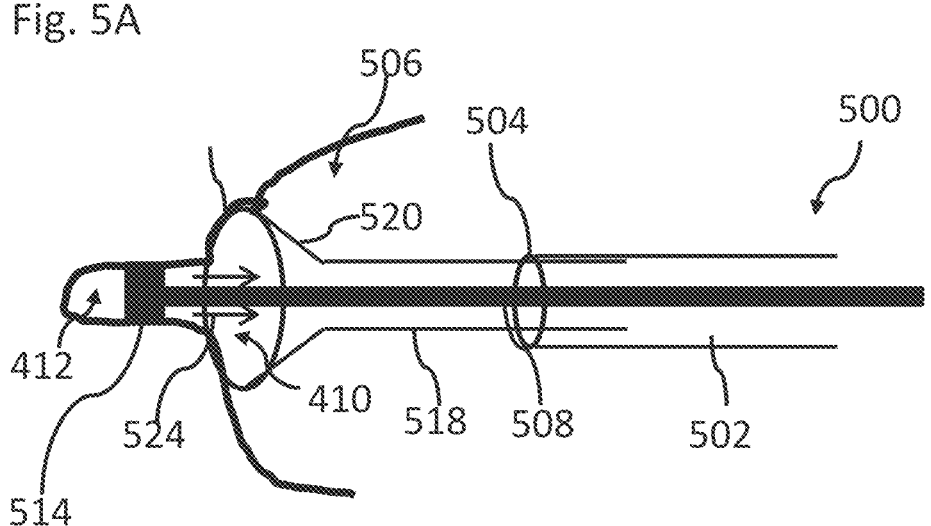
FIGS. 5A-5E are schematic illustrations of directed LAA invagination, according to some exemplary embodiments of the invention.

According to some exemplary embodiments, for example as shown in FIG. 5A, an LAA reshaper 514 is positioned within the LAA 412. In some embodiments, the LAA reshaper 514 expands and applies force against the LAA wall from within the LAA. In some embodiments, a vacuum inlet 520 of device 500 located at a distal end of a suction channel 518, is attached to an LAA opening 410, while optionally applying vacuum from the vacuum channel 518 on the LAA through the vacuum inlet 520.

Figure 5B:
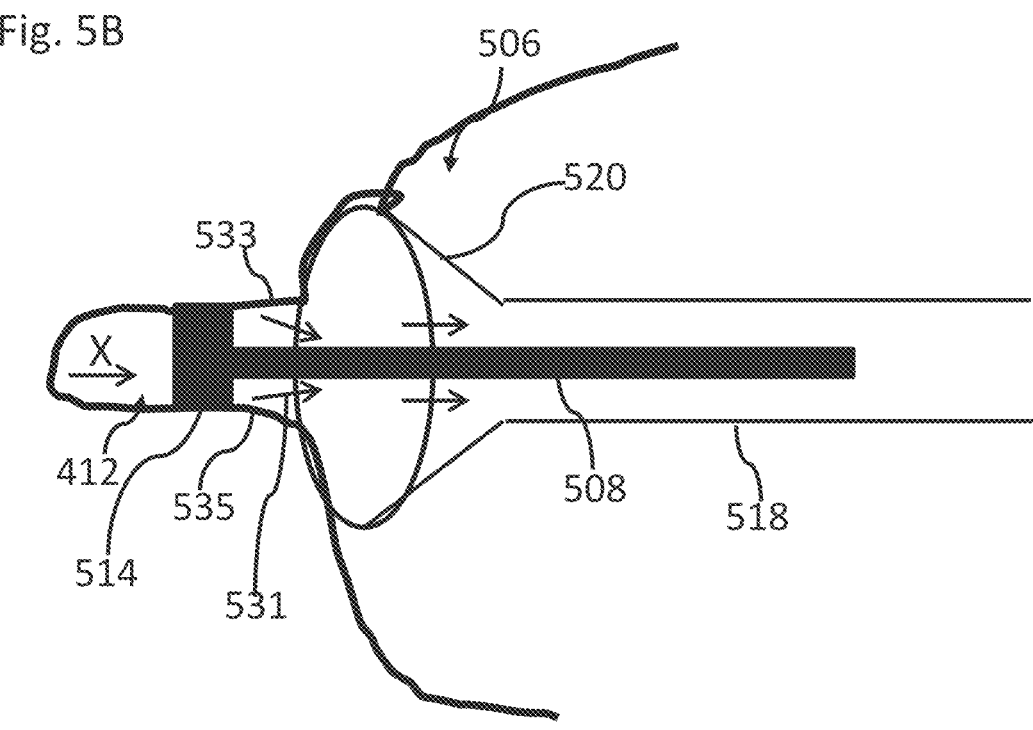

According to some exemplary embodiments, for example as shown in FIG. 5B, vacuum 531 applied on the LAA affects portions of the LAA wall that are not supported by the LAA reshaper 514, for example portions 533 and 535. In some embodiments, the LAA reshaper 514 has a front closed end and/or one or more closed portions, that allows up to 30%, for example up to 10%, up to 7%, up to 5% or any intermediate, smaller or larger percentage of vacuum to pass into distal portions of the LAA. In some embodiments, preventing vacuum application on distal portions of the LAA maintains an open LAA while allowing invagination of LAA portions closer to the LAA opening.

Figure 5C:
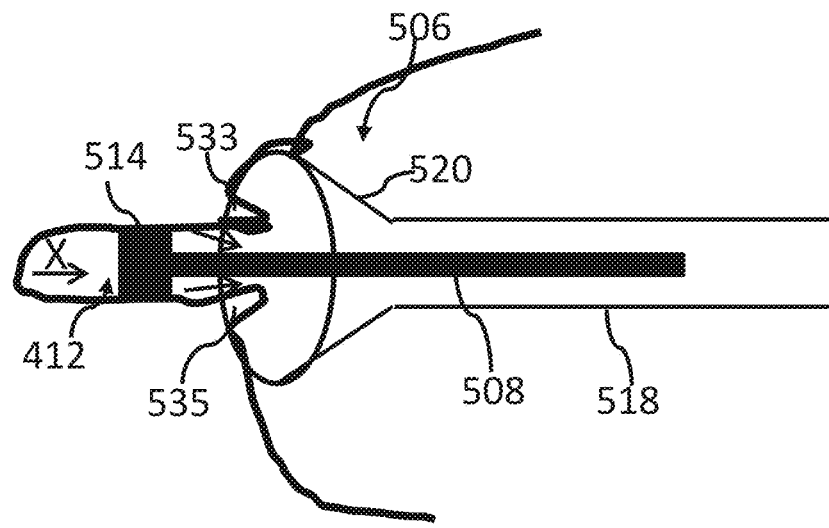

According to some exemplary embodiments, for example as shown in FIG. 5C, two or more portions of the LAA 412, for example portions 533 and 535 are invaginated into the LA 506. In some embodiments, the two or more portions are invaginated into the vacuum inlet 520. In some embodiments, the two or more portions are invaginated while keeping at least a portion of the LAA supported by the LAA reshaper 514. In some embodiments, support of the LAA by the LAA reshaper 514, prevents the collapse of the supported portions by the applied vacuum.

Figure 5D:
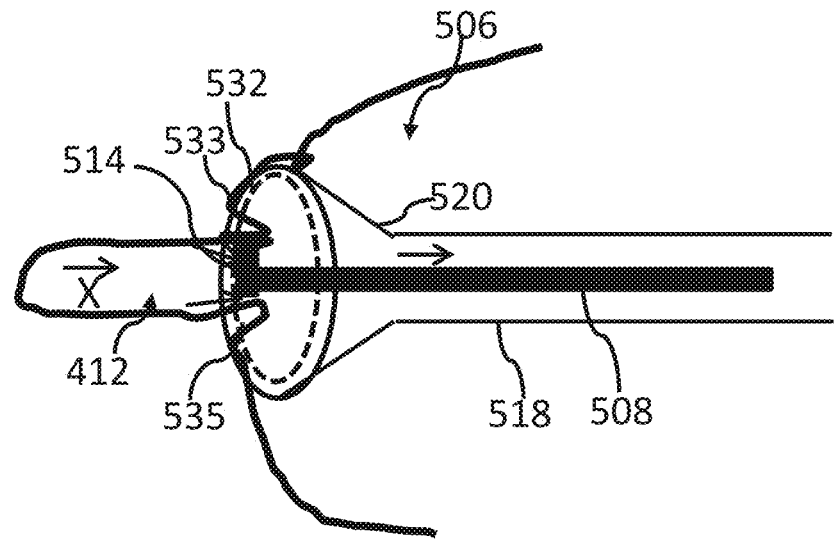

According to some exemplary embodiments, for example as shown in FIG. 5D, the LAA reshaper 514 is retracted into the vacuum inlet 520 while invaginating LAA regions contacting the LAA reshaper into the LA 506 and/or into the vacuum inlet 520. In some embodiments, during the retraction of the LAA reshaper 514 into the vacuum inlet 520, the LAA reshaper 514 detaches from the LAA wall. In some embodiments, when retracted into the suction channel 518 via the vacuum inlet 520, the LAA reshaper 514 collapses or folds to fit inside the suction channel 518.

According to some exemplary embodiments, during and/or after the invagination of the LAA into the LA, a fastener, for example a fastener loop 532 is advanced towards the invaginated portions of the LAA, for example portions 533 and 535. Alternatively, the fastener loop 532 is connected or is coupled to the vacuum inlet 520. In some embodiments, the fastener loop 532 is positioned around the invaginated portions of the LAA.

Figure 5E:
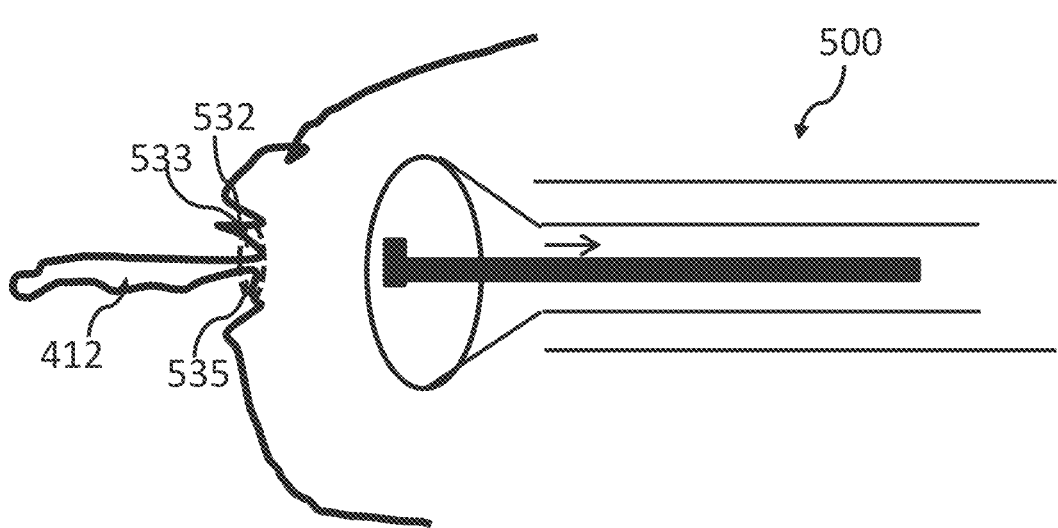

According to some exemplary embodiments, for example as shown in FIG. 5E, the fastener loop 532 fastens the invaginated portions of the LAA, for example portions 533 and 535, while disconnecting from the device 500. In some embodiments, the fastener loop 532 disconnects from the device 500 after the fastening of the inverted portions of the LAA.

Exemplary LAA Reshaping During Invagination

According to some exemplary embodiments, the LAA is reshaped during invagination into the LA. In some embodiments, an LAA reshaper positioned within the LAA reshapes the LAA by contacting and moving the contacted regions of the LAA into the LA. Alternatively or additionally, the LAA reshaper reshapes the LAA by controlling the collapse and/or shrinkage of LAA regions that are not invaginated into the LA. Reference is now made to FIGS. 6A-6I depicting LAA reshaping during invagination, according to some exemplary embodiments of the invention.

Figure 6A:
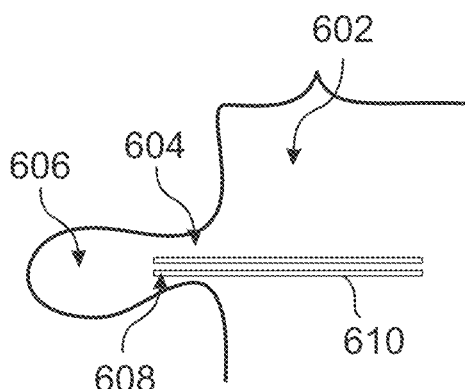

According to some exemplary embodiments, for example as shown in FIG. 6A, a distal section 608 of an LAA reshaper guide 610 is introduced at least partly from the LA 602 through the LAA opening 604 into the LAA, for example into the LAA cavity 606. In some embodiments, the LAA reshaper guide 610 is introduced into a distance of up to 35 mm from the LAA opening 604 into the LAA cavity 606, for example up to 30 mm, up to 20 mm, up to 15 mm, up to 10 mm or any intermediate, smaller or larger distance from the LAA opening 604.

Figure 6B:
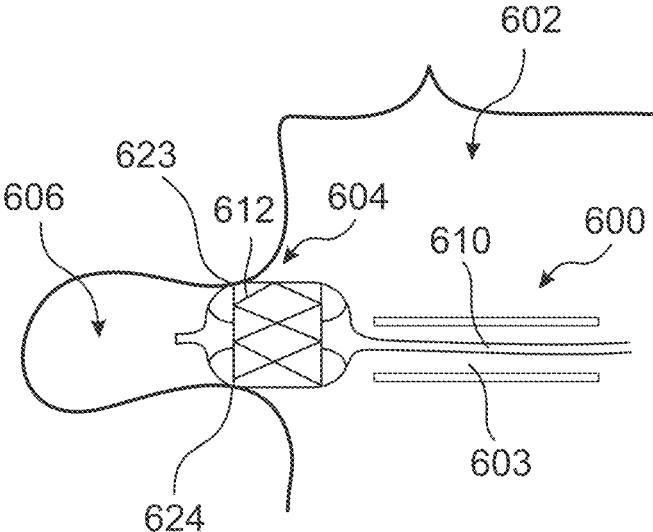

According to some exemplary embodiments, for example as shown in FIG. 6B, an LAA reshaper 612 located at a distal section of the LAA reshaper guide 610 expands at least partly within the LAA cavity 606. In some embodiments, the LAA reshaper 612 is an integral part of the LAA reshaper guide 610. Alternatively, the LAA reshaper 612 is functionally connected or coupled to the LAA reshaper guide 610. In some embodiments, expansion of the LAA reshaper 612 within the LAA cavity 606 pushes an outer surface of the LAA reshaper 612 against regions of the LAA wall, for example regions 623 and 624 of the LAA wall. In some embodiments, the LAA reshaper 612 is formed from a mesh of wires, for example bio-compatible wires. Optionally, the mesh is formed at least partially from a shape memory alloy, for example Nitinol. In some embodiments, in an expanded state, the LAA reshaper 612 acquires a substantially cylindrical shape having a diameter which is equal to or larger than a diameter or width of the LAA cavity 606, for example to allow contact between the LAA reshaper 612 and the LAA wall from within the LAA cavity 606.

According to some exemplary embodiments, a catheter of a closure device 600 having a working channel 603 is advanced along the LAA reshaper guide 610 towards the LA opening 604. In some embodiments, the LAA reshaper guide 610 is advanced into the LAA cavity 606, for example as shown in FIG. 6A, from within the working channel 603 of the catheter located in the LA.

Figure 6C:
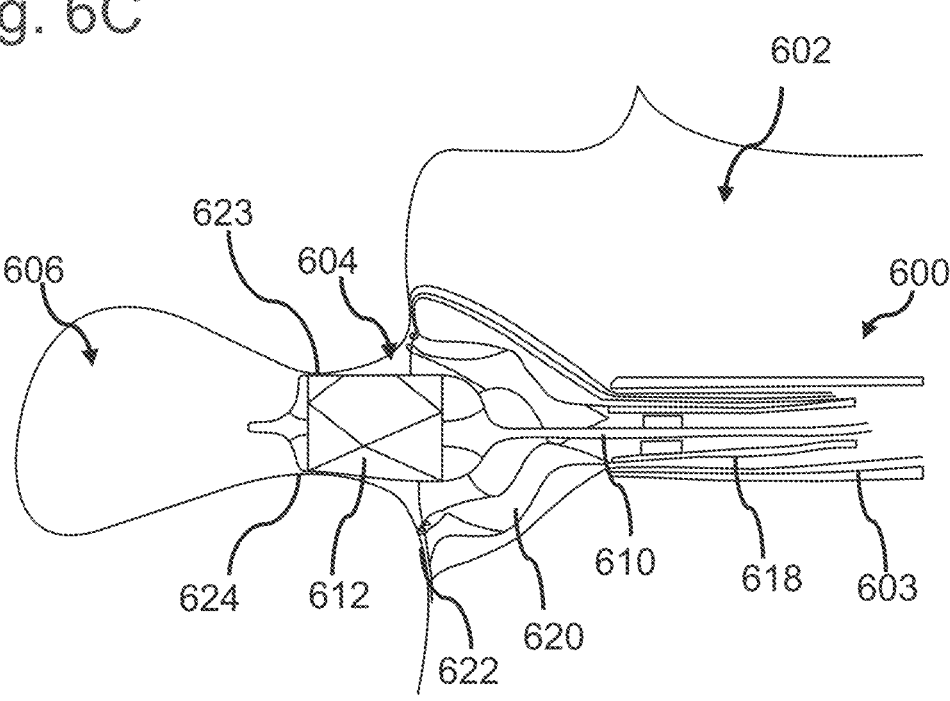

According to some exemplary embodiments, for example as shown in FIG. 6C, a vacuum inlet 620 located at a distal end of a suction channel 618 is forwardly advanced out from the working channel 603 of the catheter, towards the LAA opening 604. In some embodiments, the vacuum inlet 620 comprises an expandable vacuum inlet configured to expand when exiting from the working channel 603.

According to some exemplary embodiments, the expanded vacuum inlet 620, is shaped as a cone, cup or any other geometrical shape having a wider distal end facing the LAA opening and a narrow proximal end connected to the suction channel 618, including a flow path from outside the vacuum inlet 620 into the suction channel 618 via the wider distal end and the proximal narrow end. In some embodiments, an edge or lips of the wider distal end are attached to the LA wall 622 and around the LAA opening 604.

According to some exemplary embodiments, attachment of the vacuum inlet 620 to the LA wall 622 around the LAA opening 604 isolates the LAA 606 from the LA 602, for example to prevent the release of blood clots, floating particles, tissue debris or any other biological floating material from the LAA 606 into the LA 602 and into the blood stream. In some embodiments, the blood clots, floating particles, tissue debris or any other biological floating material inside the LAA is sucked by the applied vacuum into the suction channel 618 of the device 600. In some embodiments, the vacuum inlet 620 is attached to the LA wall 622 around the LAA opening 604 while applying vacuum, for example to increase a tight interaction between the edge or lips of the vacuum inlet 620 and the LA wall 622.

Figure 6D:
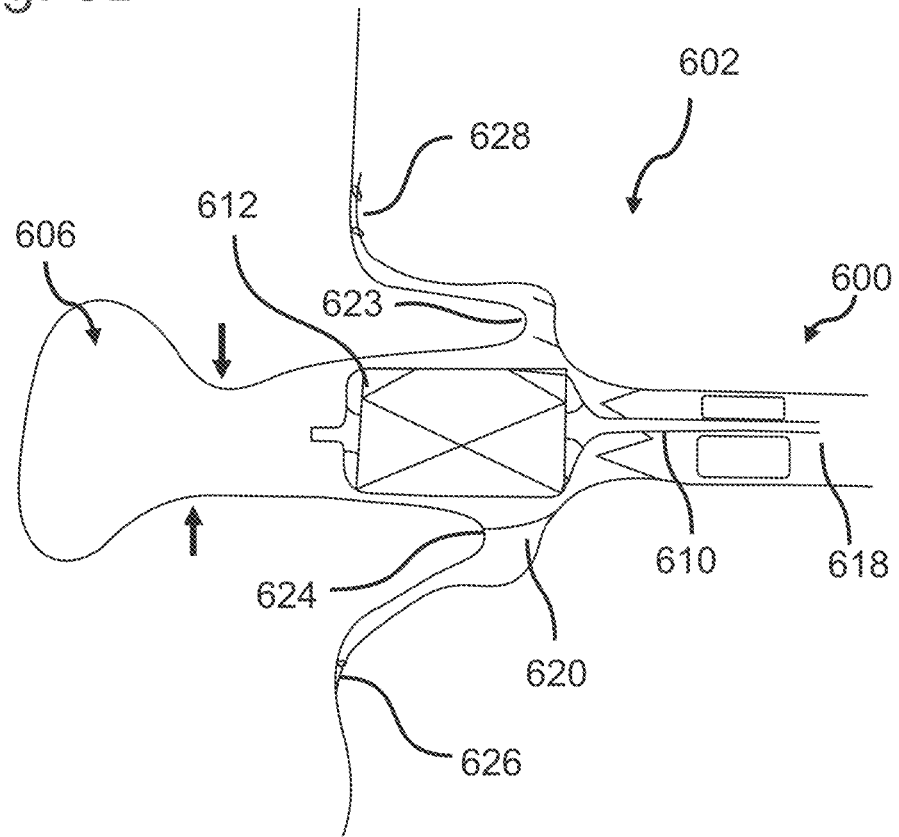

According to some exemplary embodiments, for example as shown in FIG. 6D, the LAA reshaper 612 is retracted into the LA, while vacuum is applied on the LAA 606. In some embodiments, the retraction of the LAA reshaper 612 and the applied vacuum induce invagination of two or more portions of the LAA, for example portions 623 and 624, into the LA 602 and/or into the vacuum inlet 620. Alternatively or additionally, the applied vacuum is used to maintain the isolation of the LAA from the LA during invagination and/or to remove floating particles or any other floating material exiting from the LAA during invagination.

According to some exemplary embodiments, the LAA reshaper 612 comprises a mesh structure, for example a mesh structure that is configured to allow vacuum to pass through pores of the mesh structure into the LAA. In some embodiments, the applied vacuum induces collapse for example an inward collapse, of the LAA. In some embodiments, the LAA reshaper 612 prevents the collapse of LAA regions supported by the LAA reshaper 612.

Figure 6E:
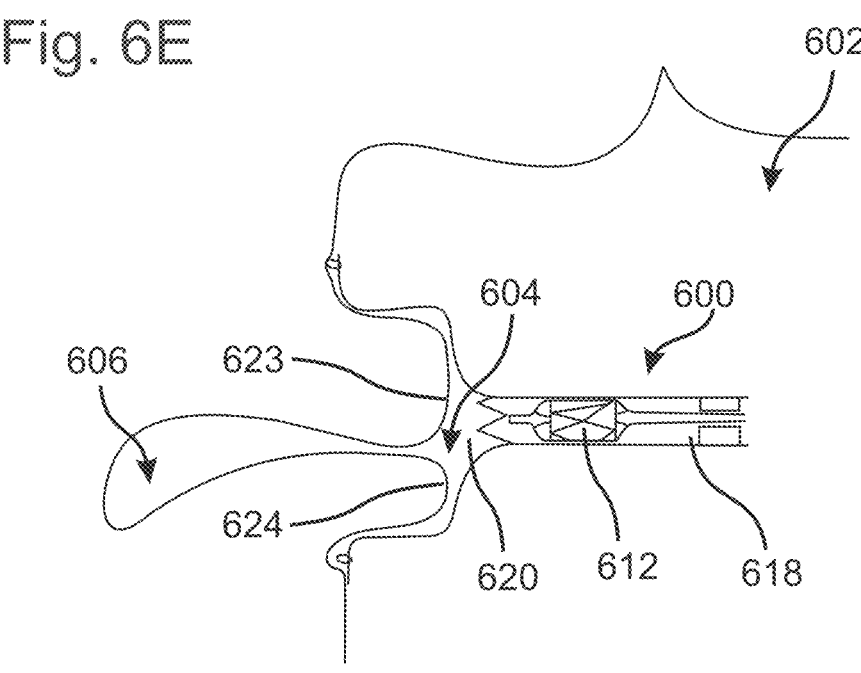
Figure 6F:
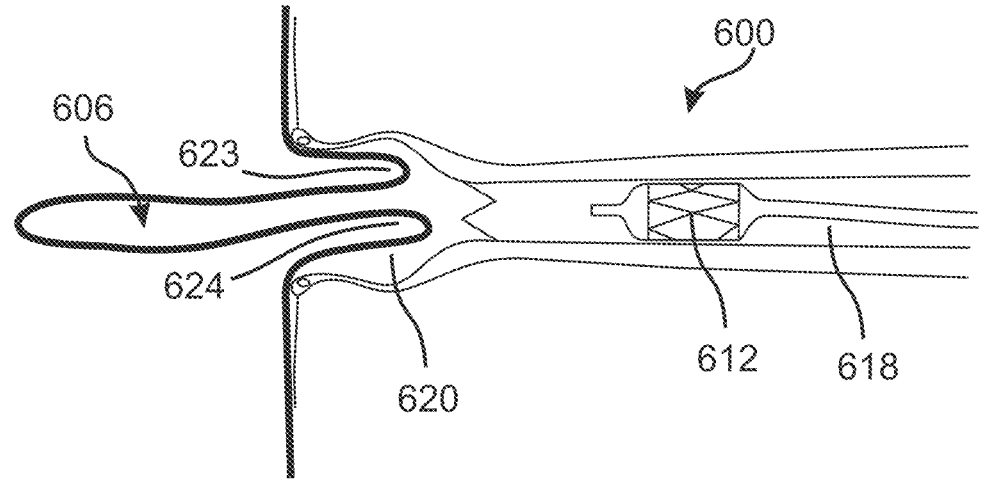

According to some exemplary embodiments, for example as shown in FIGS. 6E and 6F, the applied vacuum induces a continuous collapse of the LAA cavity 606 while the vacuum inlet 620 is constantly positioned around the LAA opening 604. In some embodiments, the vacuum inlet 620 is elastic and is configured to inwardly bend following the reshaping of the LAA and/or the reshaping of the invaginated portions of the LAA attached to the vacuum inlet 620. In some embodiments, the vacuum inlet 620 is elastic to allow bending of the LAA reshaper 612 as the LA wall surrounding the LAA opening is reshaped during the LAA collapse and/or the LAA shrinkage.

Figure 6G:
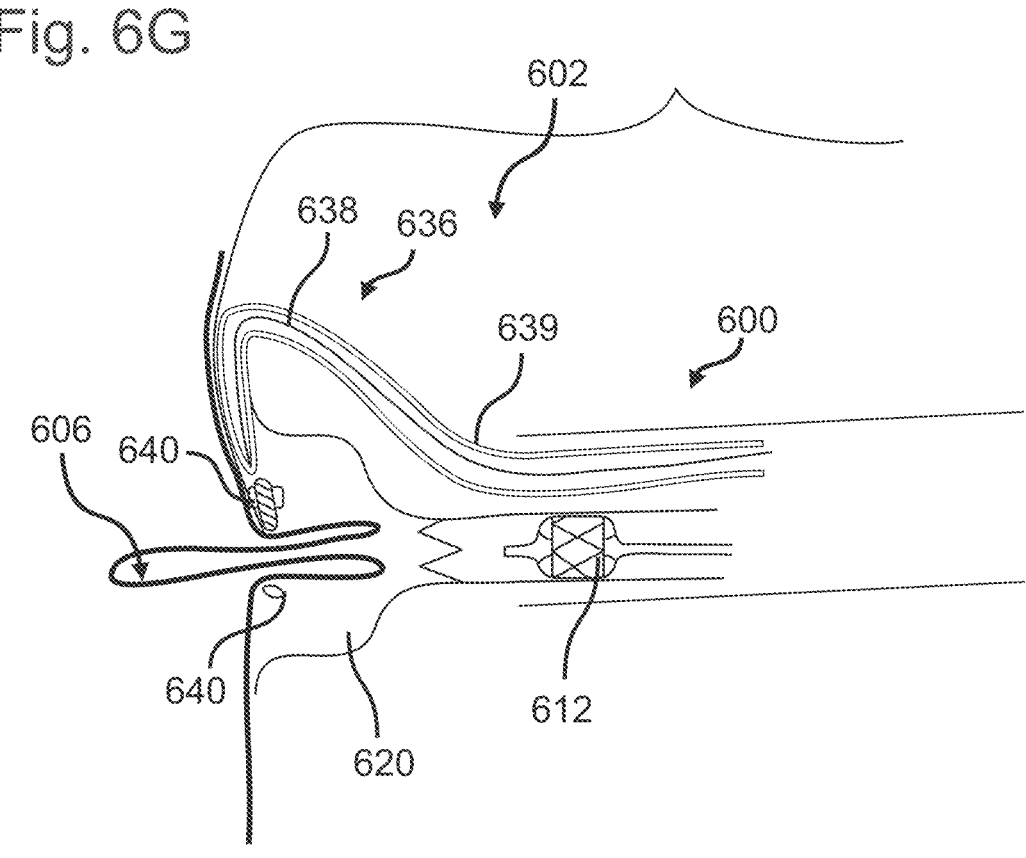

According to some exemplary embodiments, for example as shown in FIG. 6G, the invaginated portions of the LAA are fastened using a fastener assembly, for example fastener mechanism 636. In some embodiments, a fastener assembly comprises a fastener, for example a fastener loop 640, and a fastener manipulator, for example fastener manipulator 638 connected to the fastener loop 640, and a cover, for example sleeve 639. In some embodiments, the fastener manipulator 638 comprises a wire configured to transfer mechanical force to the fastener loop, for example to allow closure and/or tightening of the fastener loop around tissue. In some embodiments, the sleeve 639 is shaped and sized to cover the fastener manipulator 638, for example within the working channel of the catheter. In some embodiments, the sleeve 639 is shaped and sized to cover both the fastener loop 640 and the fastener manipulator 638, for example within the working channel of the catheter.

According to some exemplary embodiments, the fastener, for example a fastener loop 640, is positioned around the two or more invaginated portions of the LAA. In some embodiments, the fastener is positioned around the invaginated LAA portions, near the LA wall. In some embodiments, the fastener is positioned at a distance of up to 20 mm from the LA wall, for example up to 20 mm, up to 15 mm, up to 10 mm or any intermediate, smaller or larger distance from the LA wall. In some embodiments, the fastener loop 640 is positioned within the vacuum inlet 620. Optionally, the fastener loop 640 is attached to the inner portion of the vacuum inlet 620.

According to some exemplary embodiments, a fastener manipulator 638 connected to the fastener loop 640 is configured to allow fastening of the fastener loop 640 around the invaginated portions of the LAA from outside the body. In some embodiments, pulling or retraction of the fastener manipulator 638, for example within the sleeve 639 tightens the fastener loop 640 around the invaginated portions of the LAA. In some embodiments, tightening of the fastener loop 640, optionally while retracting the vacuum inlet 620, disconnects the fastener loop 640 from the vacuum inlet 620. Additionally, retraction of the vacuum inlet 620 disconnects the fastener manipulator 638 from the fastener loop 640.

Figure 6H:
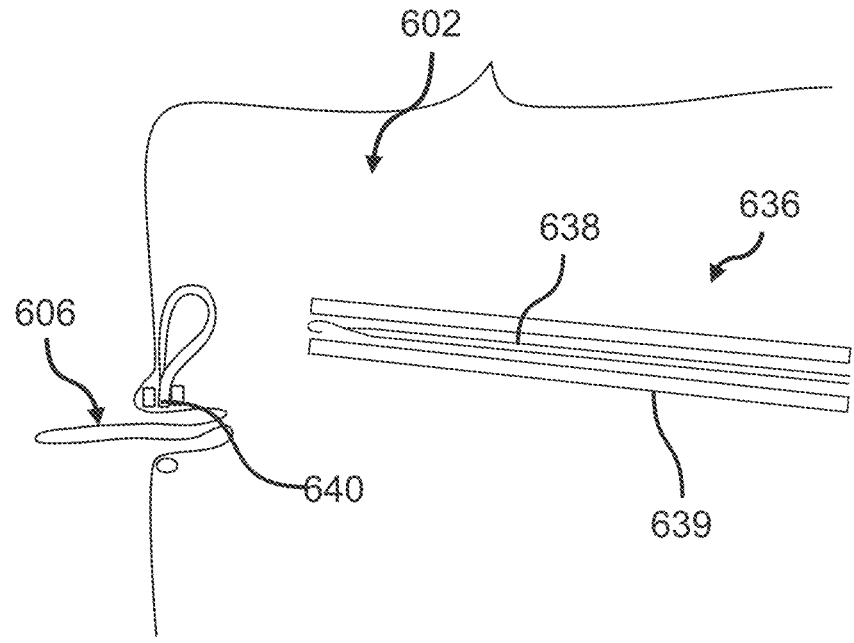

According to some exemplary embodiments, for example as shown in FIG. 6H, once the fastener loop 640 disconnects from the fastener manipulator 638, the fastener manipulator 638 is retracted into the sleeve 639, and the covered fastener manipulator 638 is then retracted into the working channel of the catheter (not shown in FIG. 6H).

Figure 6I:
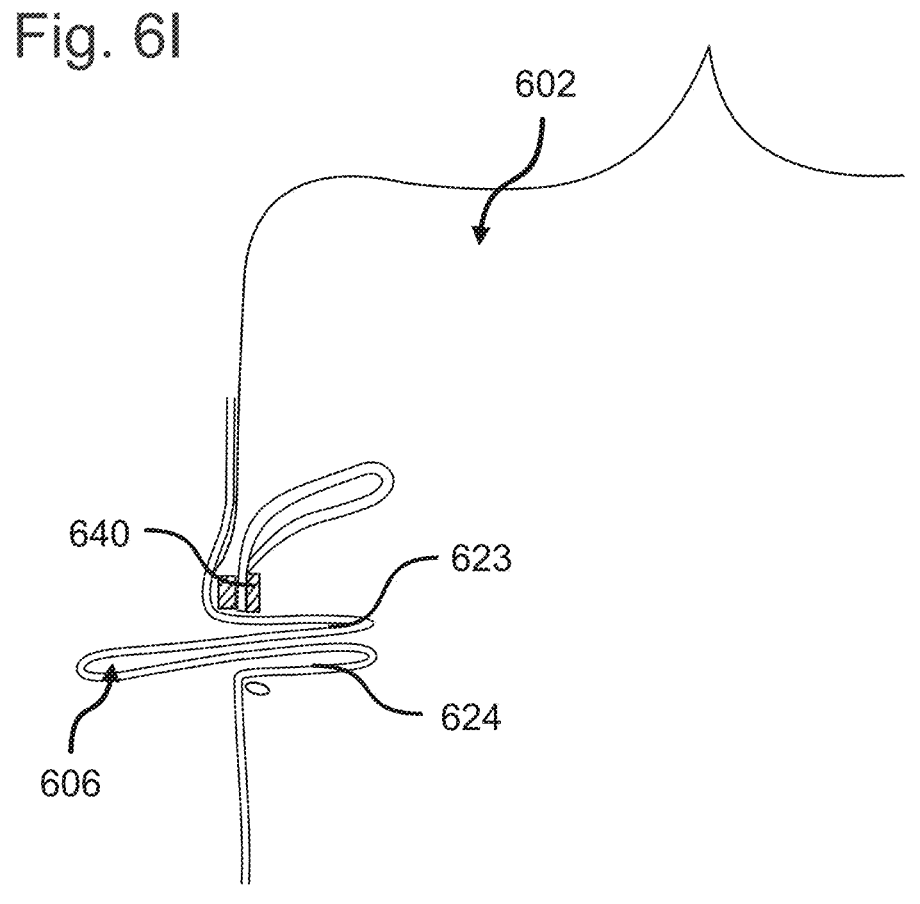

According to some exemplary embodiments, for example as shown in FIG. 6I, the catheter is retracted from the LA 602 and from the body. In some embodiments, the fastener loop 640 fastened around two or more invaginated portions of the LAA, for example portions 623 and 624, are left within the LA 602. In some embodiments, fastening of two or more portions by the fastener attaches, for example tightly attaches, the two or more invaginated LAA portions to each other. In some embodiments, the tight attachment of the two or more invaginated LAA portions closes the LAA opening and prevents the entry of blood into the LAA 606 from the LA 602. Alternatively or additionally, the tight attachment of the two or more invaginated LAA portions prevents flow of floating particles out from the LAA into the LA.

Exemplary Vacuum Inlet

According to some exemplary embodiments, a vacuum inlet is located at a distal end of a suction channel forming a sealed flow path between the vacuum inlet and the suction channel. In some embodiments, the vacuum inlet has an expandable structure configured to be in a collapsed state within a working channel of a catheter and to expand when exiting from the working channel.

According to some exemplary embodiments, the vacuum inlet comprises a conical vacuum inlet or a semi-spherical vacuum inlet, for example a concave vacuum inlet. In some embodiments, the concave vacuum inlet has a forwardly facing wide opening and a narrow opening connected to the suction channel. In some embodiments, a width of the wide opening is larger than a width of the LAA opening, for example to allow positioning of the forwardly facing wide opening around the LAA opening. Reference is now made to FIGS. 7A-7C depicting a vacuum inlet frame, according to some exemplary embodiments of the invention.

According to some exemplary embodiments, the vacuum inlet, for example vacuum inlet 700, comprises a frame, for example frame 702. In some embodiments, the frame 702 is an expandable frame. In some embodiments, the frame 702 comprises a mesh-like, for example a net-like structure, optionally formed from one or more wires, one or more tubes connected together and/or from a perforated sheet material. In some embodiments, the frame is made from a shape memory alloy, for example Nitinol.

According to some exemplary embodiments, the frame 702 comprises a semi-spherical net-like structure, for example a concave or a cone-like structure. In some embodiments, the frame 702, optionally a net-like frame, comprises, for example in an expanded state, a wide opening 712, shaped and sized to be positioned around the LAA opening or at least partly within the LAA and a narrow opening 704 functionally connectable to the suction channel.

According to some exemplary embodiments, the frame 702 comprises two or more distally extending protrusions 706 surrounding the wide opening 712. In some embodiments, at least some of the protrusions 706 comprise a flattened end 708 configured to be placed in contact with the LA wall. In some embodiments, the flattened end 708 is bended, for example bended inwardly or outwardly from the wide opening 712. In some embodiments, each of the flattened end 708 is bended to be positioned at an acute angle with relation to the LA wall, for example to disperse a pressure applied on the LA wall on a larger surface area. In some embodiments, dispersing the pressure applied on the LA wall allows, for example, to minimize injury risk to the LA wall while pressing the vacuum inlet against the LA wall. In some embodiments, at least some of the flattened ends comprise one or more openings, for example opening 710, for coupling a fastener, for example a fastener loop, to the vacuum inlet around the wide opening.

According to some exemplary embodiments, one or more of the distally extending protrusions are configured for coupling a fastener, to the vacuum inlet. In some embodiments, at least some of the protrusions are identical to each other. In some embodiments, at least some of the protrusions are different from each other. In some embodiments, protrusions that are configured to couple the fastener to the vacuum inlet are different from the rest of the protrusions. Optionally, at least some of the protrusions that are configured to couple the fastener to the vacuum inlet are identical to each other.

According to some exemplary embodiments, the frame 702 is covered with a sheet, for example a membrane. In some embodiments, the sheet is sealed to air. In some embodiments, the sheet covers an inner face of the frame 702. Alternatively, the sheet covers an outer face of the frame 702.

Exemplary Fastener

Figures 8A, 8B:
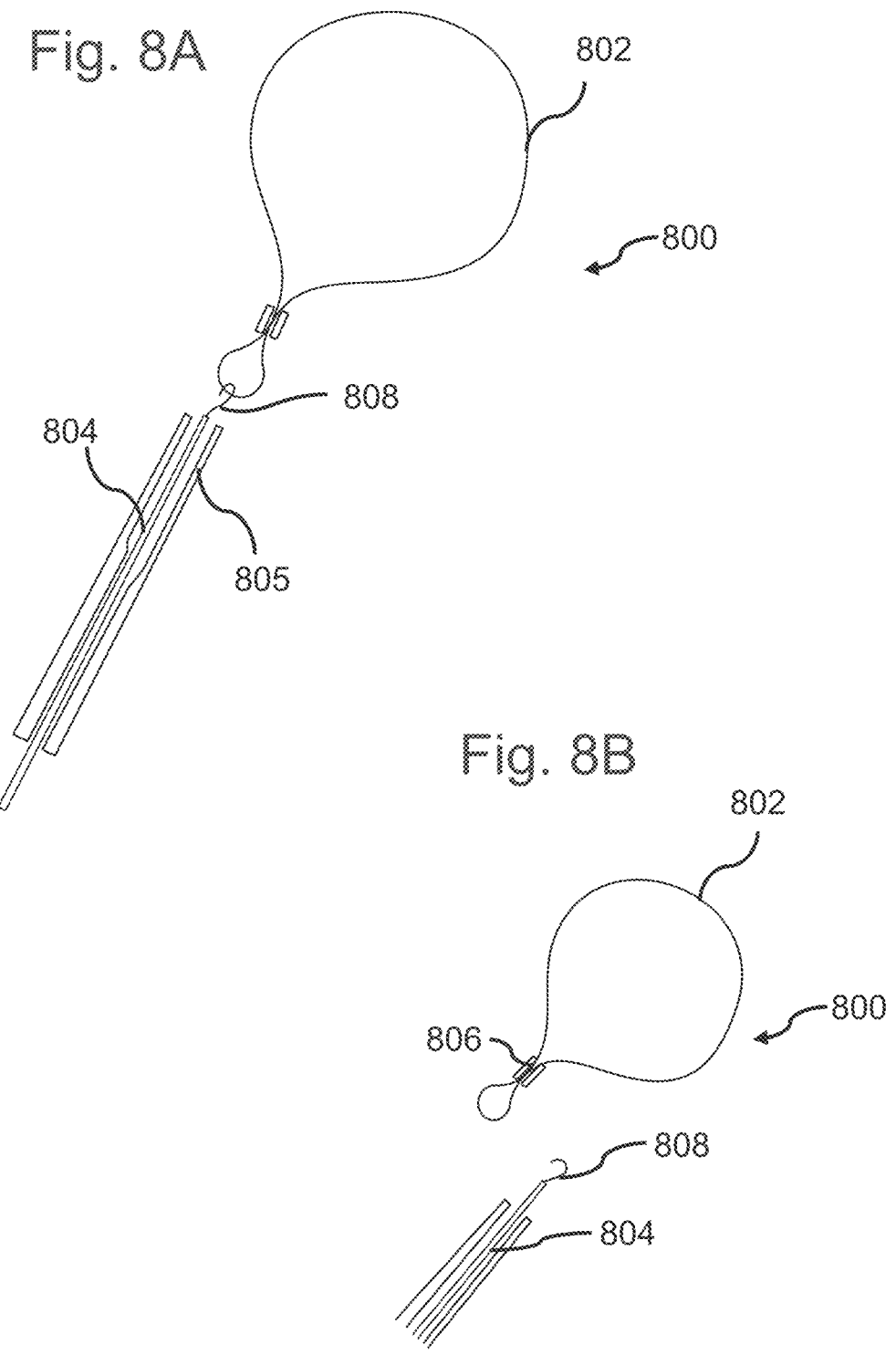
FIGS. 8A and 8B are schematic illustrations of a fastener, according to some exemplary embodiments of the invention.

Reference is now made to FIGS. 8A and 8B depicting a fastener assembly, for example a fastener mechanism 800, according to some exemplary embodiments of the invention.

According to some exemplary embodiments, a fastener, for example a fastener loop 802, is removably coupled to a fastener manipulator 804. In some embodiments, retraction or advancement of the fastener manipulator 804, for example within a sleeve 805, tightens or loosens the fastener loop 802. Alternatively or additionally, rotation of the fastener manipulator 804, for example rotation of the fastener manipulator within the sleeve 805, tightens or loosens the fastener loop 802. In some embodiments, retraction, advancement and/or rotation of the fastener manipulator 804 releases the fastener manipulator 804 from the fastener loop 802, for example as shown in FIG. 8B.

According to some exemplary embodiments, the fastener manipulator 804 comprises a hook 808 configured to removably couple the fastener manipulator 804 to the fastener loop 802.

According to some exemplary embodiments, the fastener loop 802 comprises one or more wires or strings. In some embodiments, the fastener loop 802 comprises a braided cable.

Exemplary Vacuum Inlet-Fastener Assembly

According to some exemplary embodiments, the fastener, for example a fastener loop, is coupled to a vacuum inlet of a suction channel. In some embodiments, the fastener loop is coupled to the inner surface of the vacuum inlet. Alternatively, the fastener loop is coupled to the outer surface of the vacuum inlet. In some embodiments, coupling between the fastener loop and the vacuum inlet allows, for example, to introduce them together into the LA and to position them near the LAA opening in a single step. Additionally, coupling the fastener loop to the vacuum inlet allows, for example, to have a desired relative alignment between the fastener loop and the vacuum inlet to make sure that the fastener loop surrounds invaginated LAA portion/s positioned within the vacuum inlet. Reference is now made to FIGS. 9A-9E, depicting coupling between a fastener and a vacuum inlet of a body cavity closure device, according to some exemplary embodiments of the invention.

Figure 9D:
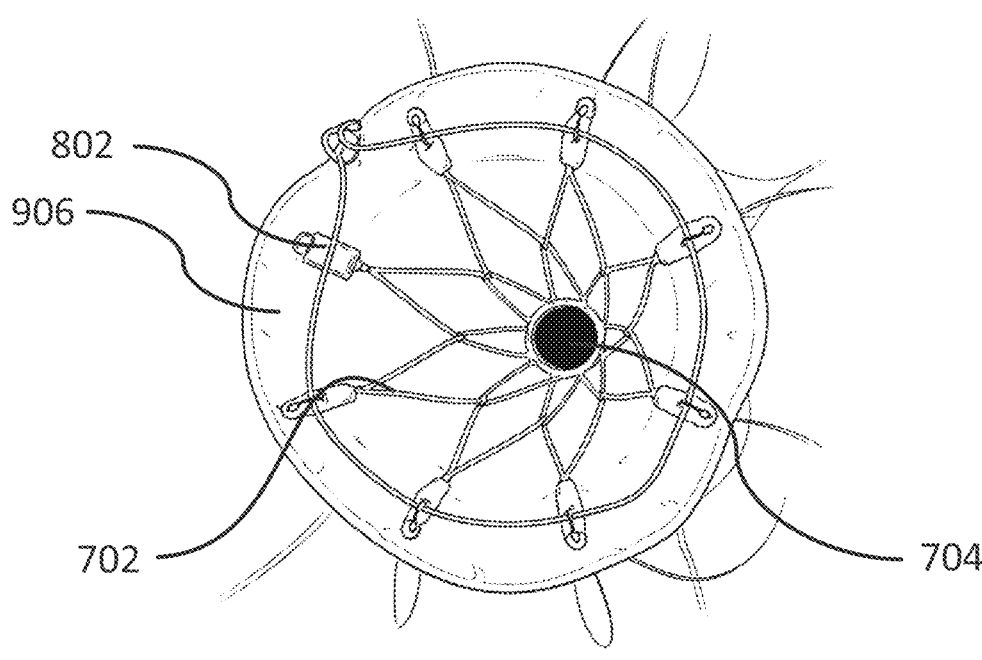
Figure 9E:
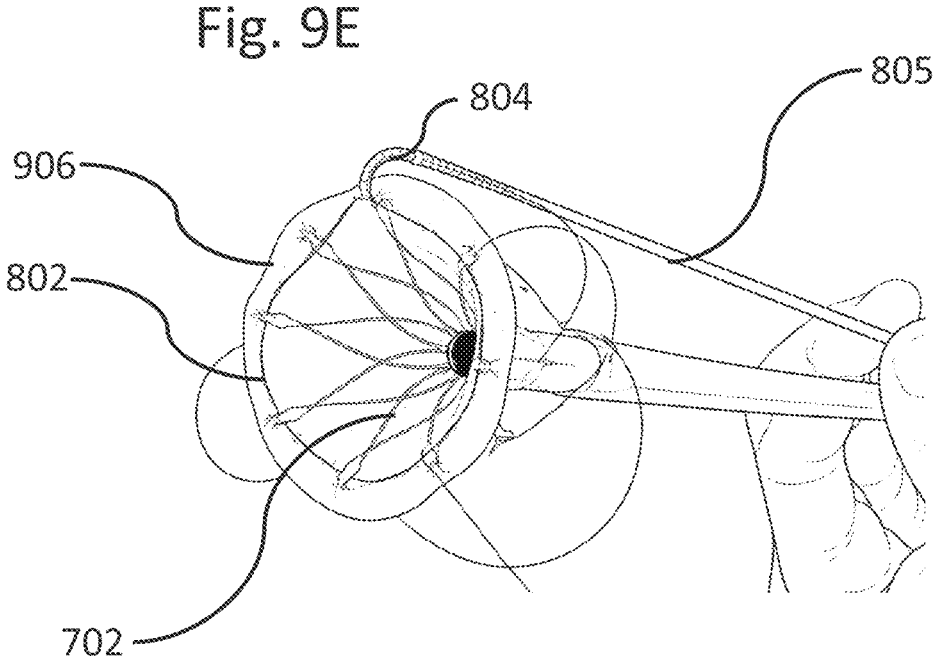

According to some exemplary embodiments, a sheet, for example flexible sheet 906 shown in FIGS. 9D and 9E, covers an inner surface of the concave vacuum inlet frame 702. In some embodiments, a fastener, for example a fastener loop 802, is positioned within the vacuum inlet. In some embodiments, the fastener loop 802 is coupled to the inner surface of the flexible sheet 906.

According to some exemplary embodiments, the flexible sheet 906 acquires a cup shape based on the shape of the frame 702. In some embodiments, the fastener loop 802 is coupled to the sheet 906 at a distance of at least 1 mm, for example 2 mm, 5 mm, 8 mm or any intermediate, smaller or larger distance from the circumference of the cup-shaped vacuum inlet. In some embodiments, the fastener loop 802 is coupled to the cup-shaped vacuum inlet at a distance from the circumference of the vacuum inlet, for example to allow uninterrupted movement of the fastener loop while the vacuum inlet is pressed against the LA wall.

Figures 10A, 10B, 10C:
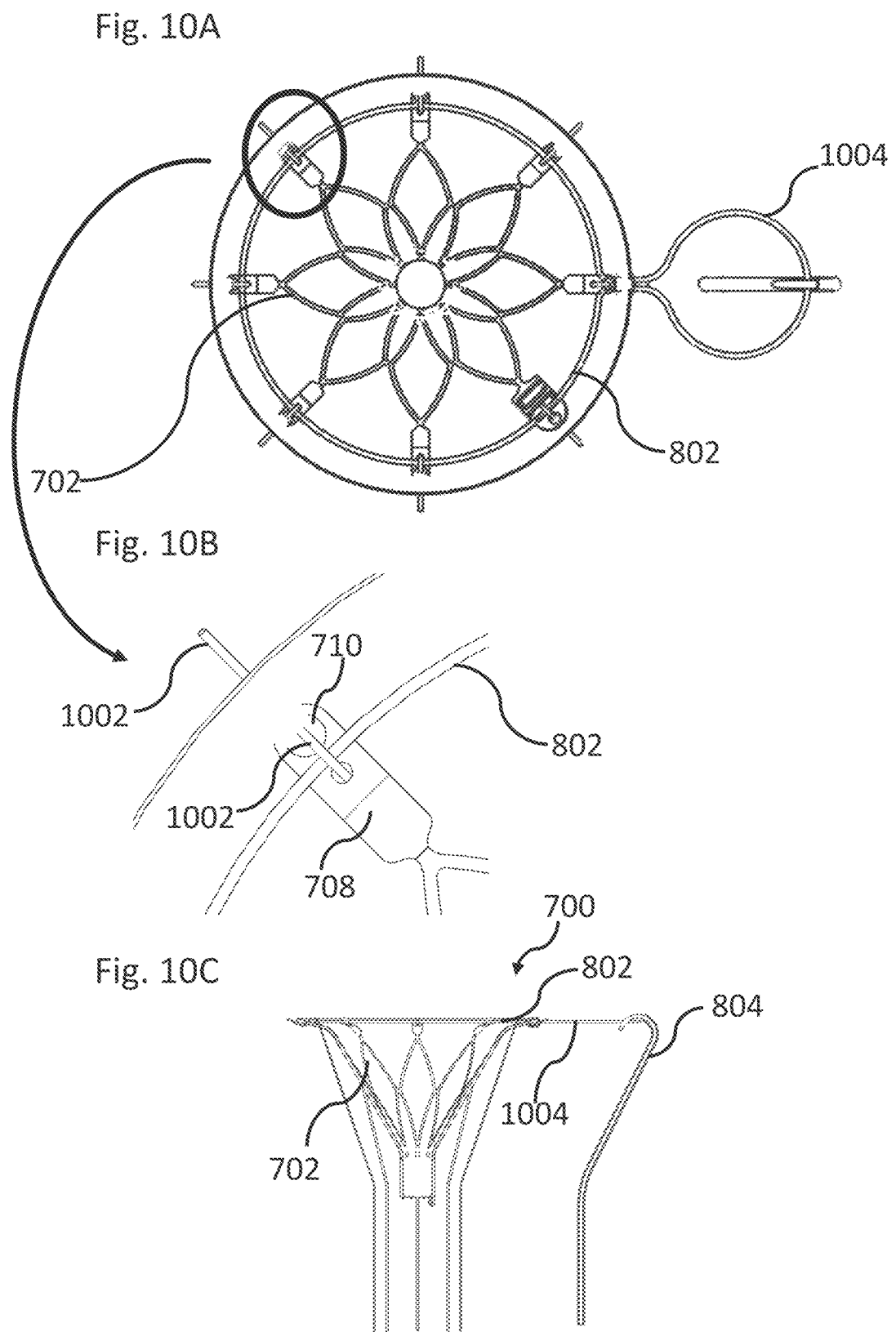
FIGS. 10A-10C are schematic illustrations of a coupling mechanism between a vacuum inlet and a fastener, according to some exemplary embodiments of the invention.

According to some exemplary embodiments, for example as shown in FIGS. 10A and 10B, the fastener loop 802 is coupled to the inner surface of the sheet by one or more wires 1002 passing through openings in the sheet and around the fastener loop 802, connecting the fastener loop to the frame 702, for example to the flattened ends 708 of the frame 702.

According to some exemplary embodiments, for example as shown in FIG. 10C, the fastener manipulator 804 is positioned outside the vacuum inlet 700. Alternatively, the fastener manipulator is positioned within the vacuum inlet 700. In some embodiments, the fastener manipulator 804 is connected via an adaptor 1004 to the fastener loop 802 positioned inside the vacuum inlet. In some embodiments, the adaptor 1004 is configured to translate retraction or advancement of the fastener manipulator 804 in a first plane to fastening of the fastener loop 802 in a second plane which is perpendicular to the first plane. Additionally or alternatively, the adaptor 1004 is configured to deliver a force and/or a movement of the fastener manipulator 804 outside the vacuum inlet to the fastener loop 802 within the vacuum inlet, optionally without interference caused by the interaction between the LA wall and the vacuum inlet 700.

Figure 9F:
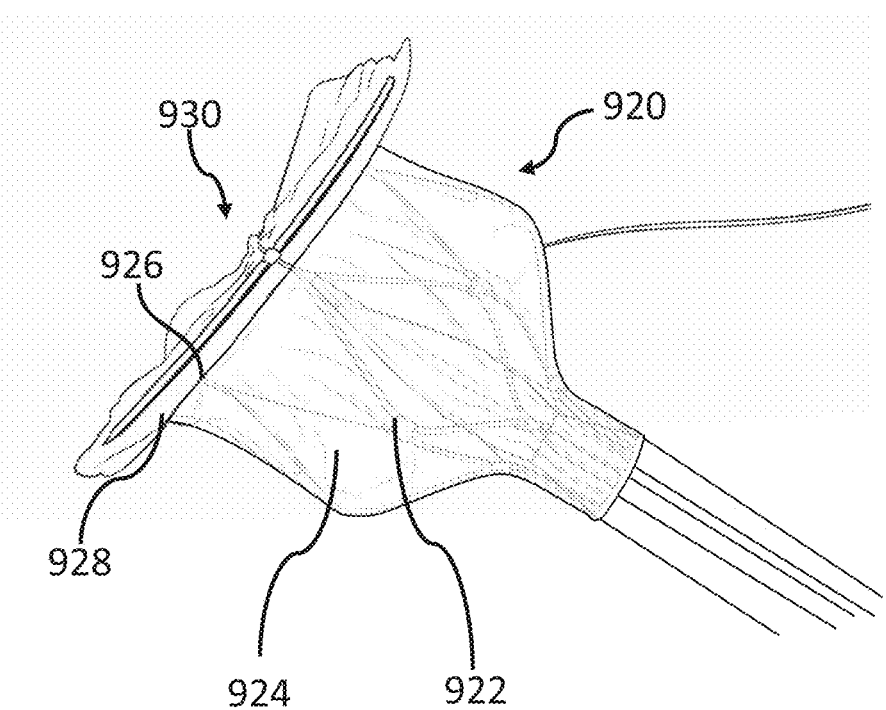
FIG. 9F is an image of a vacuum inlet with an integrated fastener, according to some embodiments of the invention.

Reference is now made to FIG. 9F, depicting a vacuum inlet with an integral fastener, according to some exemplary embodiments of the invention.

According to some exemplary embodiments, a vacuum inlet, for example vacuum inlet 920 comprises a frame, for example frame 922 covered with a sheet 924. In some embodiments, the vacuum inlet 920 comprises a fastener, for example a fastener loop 926. In some embodiments, the fastener loop 926 is integrated with the vacuum inlet 920, for example the fastener loop 926 is positioned within a channel 928 formed in the vacuum inlet 920. In some embodiments, the channel 928 is formed by folding the sheet 924. Alternatively, the channel is formed by at least partly attaching a second layer of a sheet to the sheet 924. In some embodiments, the channel is located around a distal, forwardly facing opening 930 of the vacuum inlet 920. In some embodiments, the channel 928 is located at a distance of up to 10 mm, for example up to 8 mm, up to 5 mm, up to 2 mm from the opening 930. In some embodiments, the channel 928 comprises one or more openings or voids.

Exemplary LAA Reshaper

Reference is now made to FIGS. 11A-11E depicting LAA reshapers, according to some exemplary embodiments of the invention.

According to some exemplary embodiments, an LAA reshaper, for example LAA reshaper 1100 and LAA reshaper 1106 are expandable LAA reshapers, configured to expand when exiting from a working channel of a catheter or when exiting from an inner lumen of a sleeve. In some embodiments, LAA reshaper 1100 is configured to expand into a porous net-like cylindrical body 1102. In some embodiments, the LAA reshaper 1100 expands into a closed net-like cylindrical body. In some embodiments, the cylindrical body is connected to an elongated LAA reshaper guide 1104. Optionally, the guide 1104 is formed from a hollow tube.

According to some exemplary embodiments, the LAA reshaper, for example LAA reshaper 1106, is configured to expand into a porous concave or cup-shaped ne-like body 1108 having a forwardly facing opening 1110. In some embodiments, the LAA reshaper 1106 is connected to a distal end of an elongated LAA reshaper guide 1112.

Figure 11A:
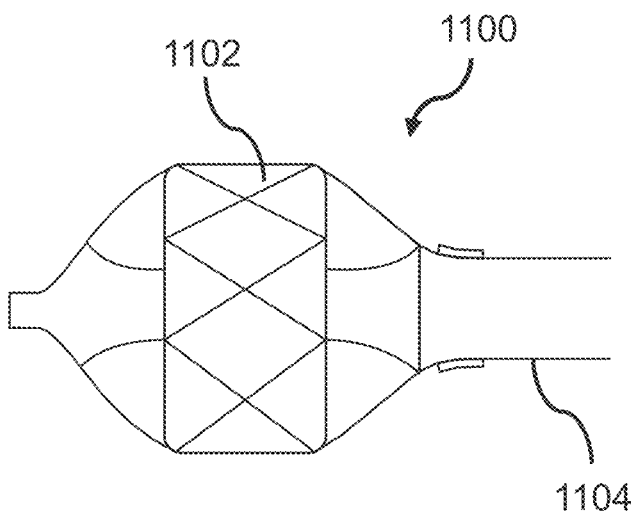
FIGS. 11A and 11B are schematic illustrations of an LAA reshaper which is optionally used for anchoring at least partially within the LAA, according to some exemplary embodiments of the invention.
Figure 11B:
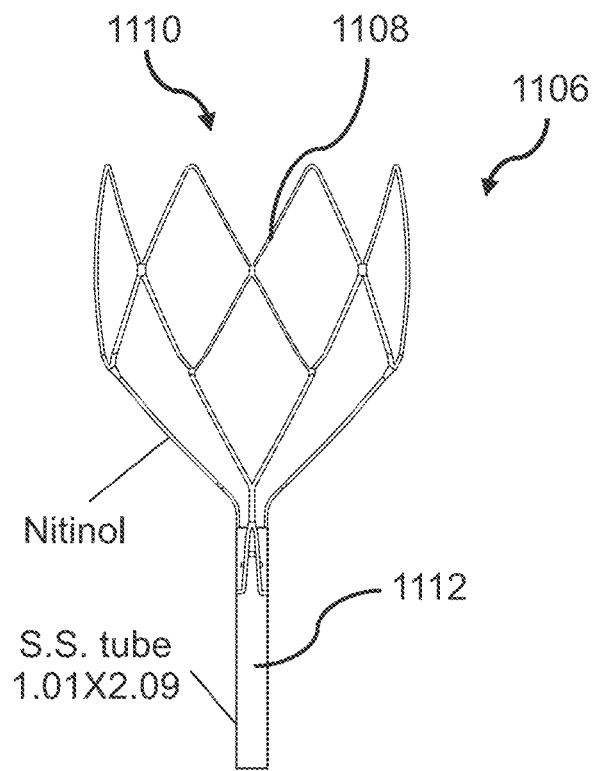
Figure 11C:
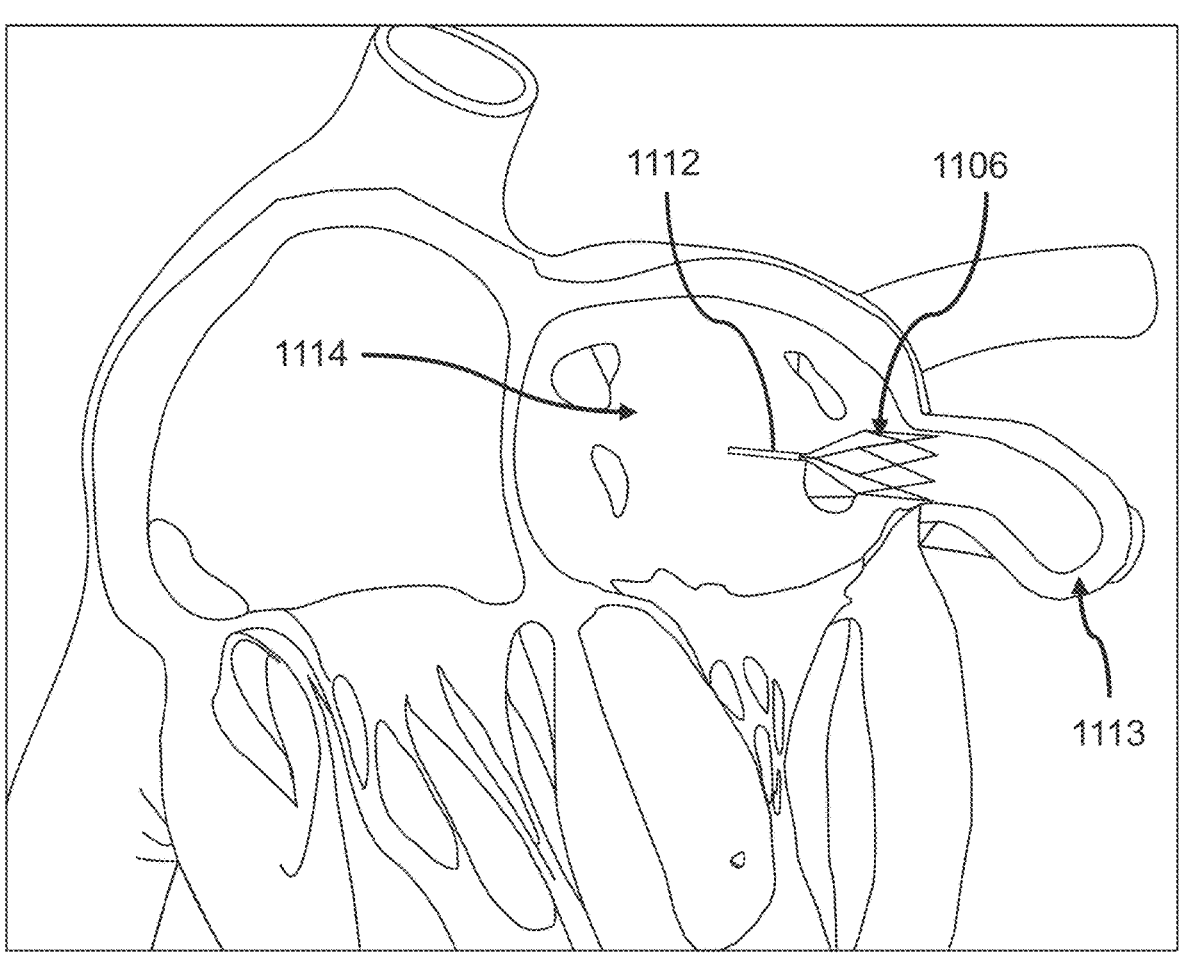
FIG. 11C is a schematic illustration of the LAA reshaper shown in FIG. 11B at least partly within the LAA, according to some exemplary embodiments of the invention.

According to some exemplary embodiments, the LAA reshaper, for example LAA reshaper 1100 and LAA reshaper 1106, is formed from one or more wires, cables or strands, that are optionally made from a shape memory alloy, for example Nitinol. In some embodiments, the LAA reshaper guide, for example LAA reshaper guide 1104 and LAA reshaper guide 1112, comprises one or more elongated stainless steel tubes. In some embodiments, the LAA reshaper guide comprises a bendable tube configured to elastically bend, for example to allow navigation of the LAA reshaper connected to the guide to different locations within the LA. In some embodiments, the LAA reshaper guide is movable within a cover, for example a sleeve or an inner lumen of a channel. In some embodiments, when placed within the cover, the LAA reshaper is in a collapsed state. In some embodiments, retraction of the cover or advancement of the LAA reshaper guide, moves the LAA reshaper, for example LAA reshaper 1106, outside the cover and at least partly into the LAA 1113, for example as shown in FIG. 11C. In some embodiments, the LAA reshaper 1106 expands within the LAA 1113 and applies force against the LAA wall, while the LAA reshaper guide 1112 remains connected to the LAA reshaper 1106 and is located in the LA 1114.

Figure 11D:
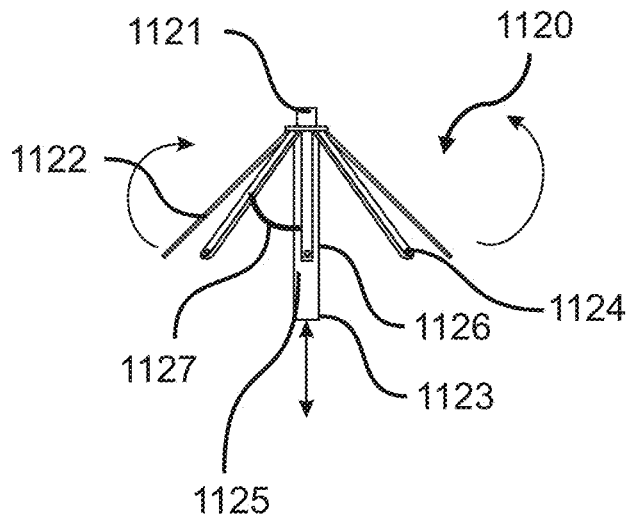
FIG. 11D is a schematic illustration of an LAA reshaper which is optionally used to direct a collapse of at least a portion of the LAA into a vacuum inlet, according to some exemplary embodiments of the invention.
Figure 11E:
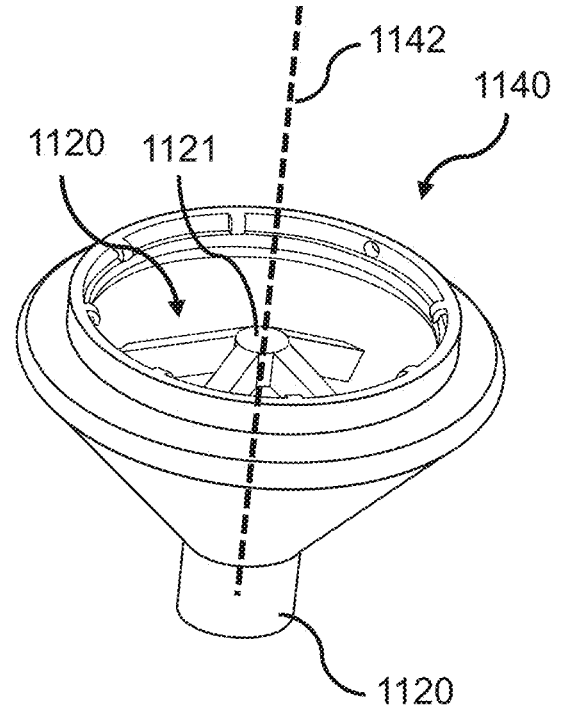
FIG. 11E is a schematic illustration of a vacuum inlet comprising the LAA reshaper shown in FIG. 11D, according to some exemplary embodiments of the invention.

According to some exemplary embodiments, for example as shown in FIGS. 11D and 11E, the LAA reshaper is used to reshape portions of the LAA that are invaginated into the vacuum inlet. In some embodiments, the LAA reshaper has a conical shape with an inner lumen. In some embodiments, a surface of the cone-shaped LAA reshaper comprises a plurality of openings, shaped and sized to allow vacuum application from within the lumen of the conical LAA reshaper. In some embodiments, an apex of the conical LAA reshaper is located distally to a suction channel. Additionally, a base of the conical LAA reshaper is coupled to a vacuum inlet of the suction channel. In some embodiments, a distance between the apex and the base of the conical LAA reshaper is adjustable, for example according to a signal delivered from outside the body. In some embodiments, the apex of the conical LAA reshaper extends at least partly into the LAA, while optionally the base remains outside the LAA, for example in the LA. Alternatively, both the apex and the base of the LAA reshaper remain outside the LAA in the LA.

According to some exemplary embodiments, for example as shown in FIG. 11D, the LAA reshaper, for example LAA reshaper 1120, comprises one or more elongated bars, for example bar 1126 having a longitudinal axis, a distal end 1121 and a proximal end 1123. Optionally, the bar 1126 is vertical. In some embodiments, the LAA reshaper 1120 has a conical shape, where the distal end 1121 of the bar 1126 is the apex of the conical shape. In some embodiments, the term "distal end" refers to an end which is located closer to the LAA, and the term "proximal end" refers to an end positioned farther away from the LAA. In some embodiments, the LAA reshaper 1120 comprises one or more rods, for example 2, 3, 4, 5, 6, 7, 8 rods or any larger number of rods, for example rod 1124, connected with one end to the bar 1126 and extending sideways from the bar 1126, for example to contact an internal surface of a vacuum inlet, for example vacuum inlet 1140 shown in FIG. 11E. In some embodiments, the contacting points between the conical LAA reshaper, for example the contacting points between the rods forming the conical shape, and the vacuum inlet, define a base of the conical LAA reshaper.

According to some exemplary embodiments, the one or more rods, for example rods 1122 and 1124, are connected to the bar 1126 near the distal end 1121 of the bar 1126, for example at a distance of up to 10 mm from the distal end 1121. In some embodiments, the rods are connected to the bar at locations that have a similar axial position and different circumferential position on the circumference of the bar 1126. In some embodiments, an angle, for example angle 1127, between one or more of the rods and a portion of the bar 1126 between the connection point of the rod to the bar and a proximal end of the bar, for example portion 1125, is an acute angle smaller than 90 degrees. In some embodiments, one end of each of the rods is connected to the bar and a second end of each of the rods is connected to an inner surface of a vacuum inlet, for example vacuum inlet 1140 shown in FIG. 11E.

According to some exemplary embodiments, the elongated bar 1126 is axially movable. In some embodiments, each of the rods, for example rods 1122 and 1124, is pivotally connected to the bar 1126, for example to allow changing of the angle 1127. In some embodiments, changing the angle 1127 allows, for example, to control the volume and/or the size of the LAA tissue invaginated into the vacuum inlet 1140 and/or into the LA. In some embodiments, decreasing the angle 1127 allows, for example, to invaginate a larger volume and/or size of LAA into the vacuum inlet 1140 by allowing more LAA tissue to penetrate into the vacuum inlet 1140. Alternatively, increasing the angle 1127 allows, for example, to reduce the amount and/or volume of invaginated LAA tissue into the vacuum inlet 1140.

According to some exemplary embodiments, for example as shown in FIG. 11E, the LAA reshaper 1120 is positioned inside the vacuum inlet, for example vacuum inlet 1140. In some embodiments, the vacuum inlet is shaped as a hollow cone having a longitudinal axis 1142, a wide distal portion and a narrow proximal portion. In some embodiments, the wide distal portion and the narrow proximal portion are aligned along the longitudinal axis 1142 of the vacuum inlet 1140.

According to some exemplary embodiments, a central elongated bar of the LAA reshaper, for example bar 1126, is axially aligned along the longitudinal axis 1142 of the vacuum inlet 1140. In some embodiments, the bar 1126, is movable into and out from a suction channel connected to an opening in the proximal narrow portion of the vacuum inlet 1140. Alternatively, the LAA reshaper 1120 is an integral part of the inner lumen of the vacuum inlet 1140.

According to some exemplary embodiments, inside the vacuum inlet 1140 lumen, a central portion of the LAA reshaper, for example the distal end 1121 of the bar 1126 is distal to other portions of the LAA reshaper, for example bars 1122 and 1124, for example to direct the collapse of inner side walls of the LAA into the vacuum inlet lumen while keeping a central vacuum flow path open.

Exemplary LAA Closure Device

Figure 12A:
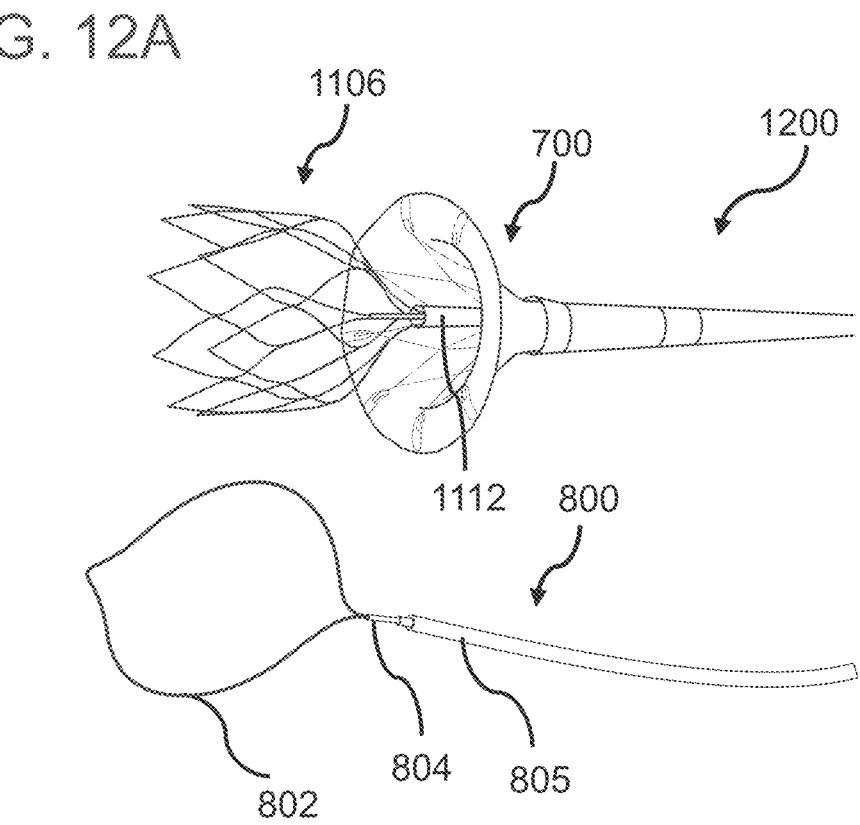
FIGS. 12A-12B are images of an LAA closure device, according to some exemplary embodiments of the invention.
Figure 12B:
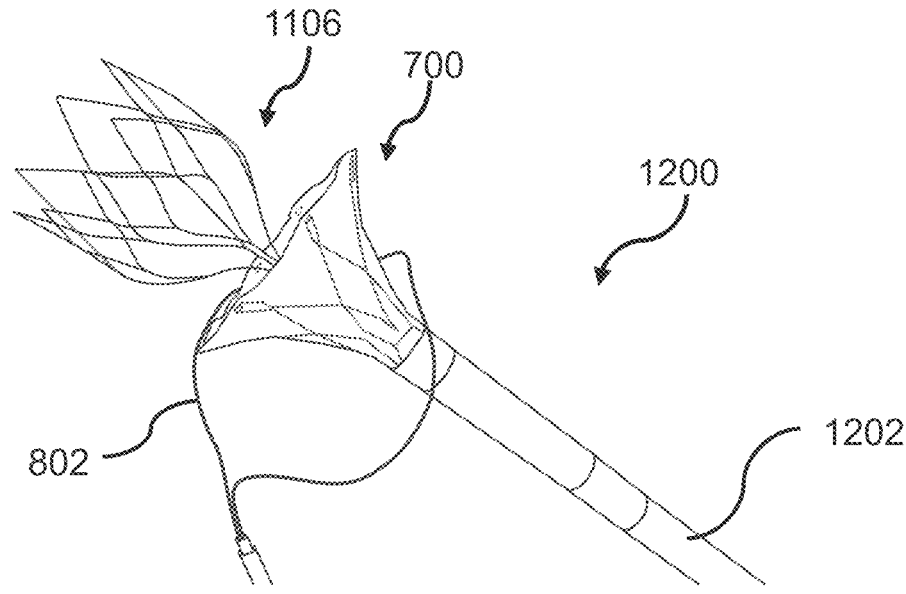

Reference is now made to FIGS. 12A-12B depicting an LAA closure device, according to some exemplary embodiments of the invention.

According to some exemplary embodiments, an LAA closure device, for example closure device 1200 comprising a catheter, for example catheter 1202, having an inner working channel with a distal end configured to be navigated into the LA and a proximal opening, for example a proximal opening located outside the body. In some embodiments, an elongated suction channel terminating with an expandable vacuum inlet 700 is disposed within the working channel of the catheter 1202.

According to some exemplary embodiments, the LAA closure device, for example closure device 1200 comprises a fastener mechanism 800. In some embodiments, the fastener mechanism 800 comprises a fastener, for example a fastener loop 802, connected to a fastener manipulator 804.

In some embodiments, the fastener is placed within a sleeve 805. In some embodiments, the fastener loop 802 is coupled to an inner surface or an outer surface of the vacuum inlet, for example as shown in FIGS. 9D and 9E. Alternatively, the fastener loop is separated from the vacuum inlet, and is shaped and sized to pass over the vacuum inlet and fasten one or more invaginated portions of the LAA. Alternatively, the fastener loop is separated from the vacuum inlet and is shaped and sized to fasten one or more invaginated portions of the LAA from within the vacuum inlet.

According to some exemplary embodiments, an LAA reshaper, for example an expandable LAA reshaper 1106, is connected to a distal end of an LAA reshaper guide 1112 which passes within the suction channel or outside the suction channel within the working channel of the catheter.

According to some exemplary embodiments, when the catheter 1202 enters into the LA, the LAA reshaper is advanced in a collapsed state within the working channel of the catheter 1202. In some embodiments, the LAA reshaper is then inserted at least partly into the LAA and expands therein. In some embodiments, the expandable vacuum inlet 700 is advanced within the working channel, for example along the LAA reshaper guide. In some embodiments, the vacuum inlet 700 expands within the LA and placed in contact with the LA wall around the LAA opening, In some embodiments, the vacuum inlet 700 is at least partly flexible and/or elastic, for example to allow tight contact between the inner surface of the vacuum inlet and non-planar, for example curved regions of the LA.

According to some exemplary embodiments, vacuum is applied through the vacuum inlet 700 on the LAA cavity, for example to allow tight contact between the inner surface of the vacuum inlet 700 and the LA wall and/or to invaginate one or more portions of the LAA into the vacuum inlet 700. In some embodiments, a fastener loop 802 is positioned around the invaginated portions and is fastened, for example by retraction of the fastener manipulator 804, optionally into a sleeve 805. In some embodiments, the sleeve 805 and/or the fastener manipulator 804 pass within the suction channel. Alternatively, the fastener manipulator 804 and/or the sleeve 805 pass outside the suction channel within the working channel of the catheter 1202.

According to some exemplary embodiments, if the fastener loop is coupled to the vacuum inlet, for example as shown in FIGS. 9D and 9E, fastening of the fastener loop 802 separates the fastener loop 802 from the vacuum inlet. In some embodiments, the LAA reshaper 1106 retracts into the vacuum inlet 700 during the invagination process. In some embodiments, the LAA reshaper guide 1112 is configured to retract into the suction channel, for example to allow retraction of the LAA reshaper 1106 into the vacuum inlet 700.

According to some exemplary embodiments, once at least some of the invaginated portions of the LAA are fastened, the vacuum inlet 700 and the fastener are retracted into the working channel of the catheter, for example catheter 1202.

Figure 13A:
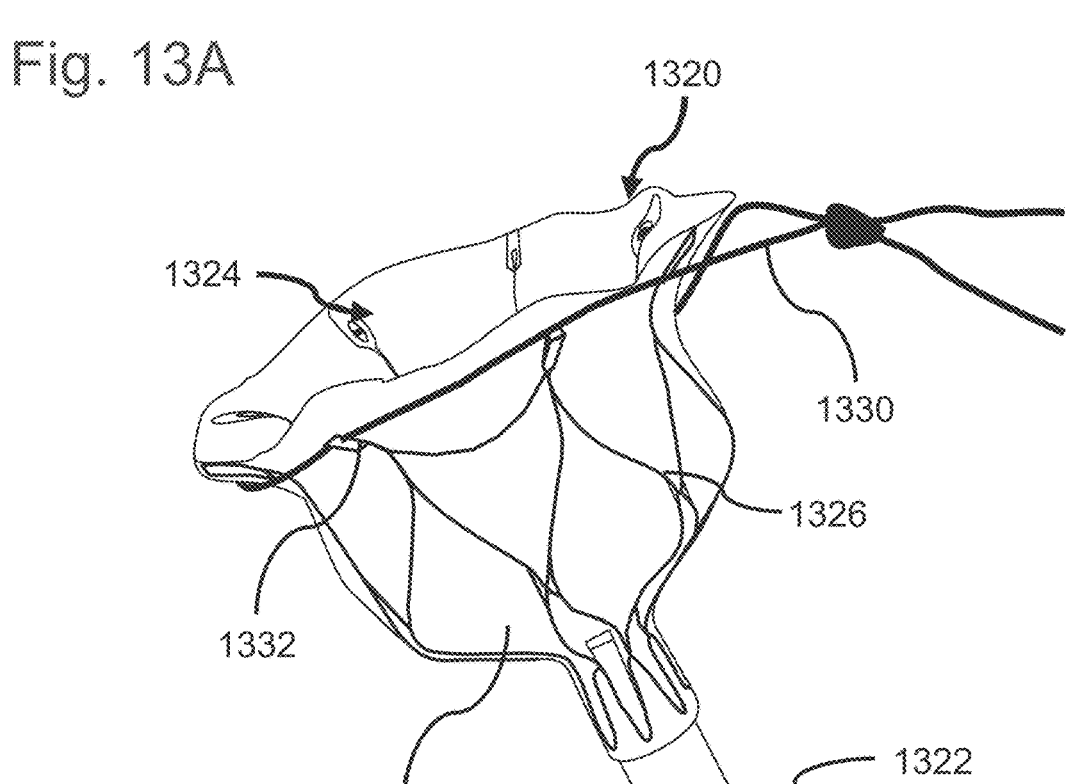
FIGS. 13A-13C are images of an LAA closure device having an LAA reshaper with a distally extending guide, according to some exemplary embodiments of the invention.

According to some exemplary embodiments, for example as shown in FIG. 13A, an LAA closure device, comprising an elongated suction channel, for example suction channel 1322, terminating with a vacuum inlet 1320. In some embodiments, the vacuum inlet 1320 has a concave shape with a forwardly facing opening 1324. In some embodiments, the forwardly facing opening 1324 is located at a distal end of the vacuum inlet 1320, away from the suction channel 1322.

According to some exemplary embodiments, the vacuum inlet 1320 comprises a frame 1326, for example a collapsible frame. In some embodiments, the frame 1326 is formed from a shape memory alloy, for example Nitinol. In some embodiments, the frame 1326 is configured to expand out from a working channel of a catheter, for example into the LA, and to collapse into the working channel when the LAA invagination process is completed. In some embodiments, the frame 1326 is formed from one or more wires, bended to form the concave shape.

According to some exemplary embodiments, an inner surface and/or an outer surface of the frame is covered with a sheet, for example sheet 1328. In some embodiments, the sheet is formed at least partly from Silicon or Polyurethane. In some embodiments, the sheet is at least 80% sealed, for example at least 85% sealed, at least 90% sealed or any intermediate, smaller or larger percentage, to allow application of vacuum from the suction channel 1322 through the vacuum inlet 1320. Alternatively, the sheet 1328 is completely sealed.

According to some exemplary embodiments, a fastener, for example a fastener loop 1330 is coupled to the vacuum inlet 1320. In some embodiments, the fastener loop is formed from a wire or a thread. In some embodiments, for example as shown in FIG. 13A, the fastener loop 1330 is coupled to the vacuum inlet 1320 by passing the fastener loop 1330 through one or more slits in the sheet 1328, for example slit 1332. In some embodiments, the sheet 1328 is at least partly folded over the fastener loop 1330. In some embodiments, the one or more slits in the sheet 1328 through which the fastener loop 1330 passes are shaped and sized to be cut when the fastener loop 1330 is fastened, for example to allow decoupling of the fastener loop 1330 from the vacuum inlet 1220.

Figure 13B:
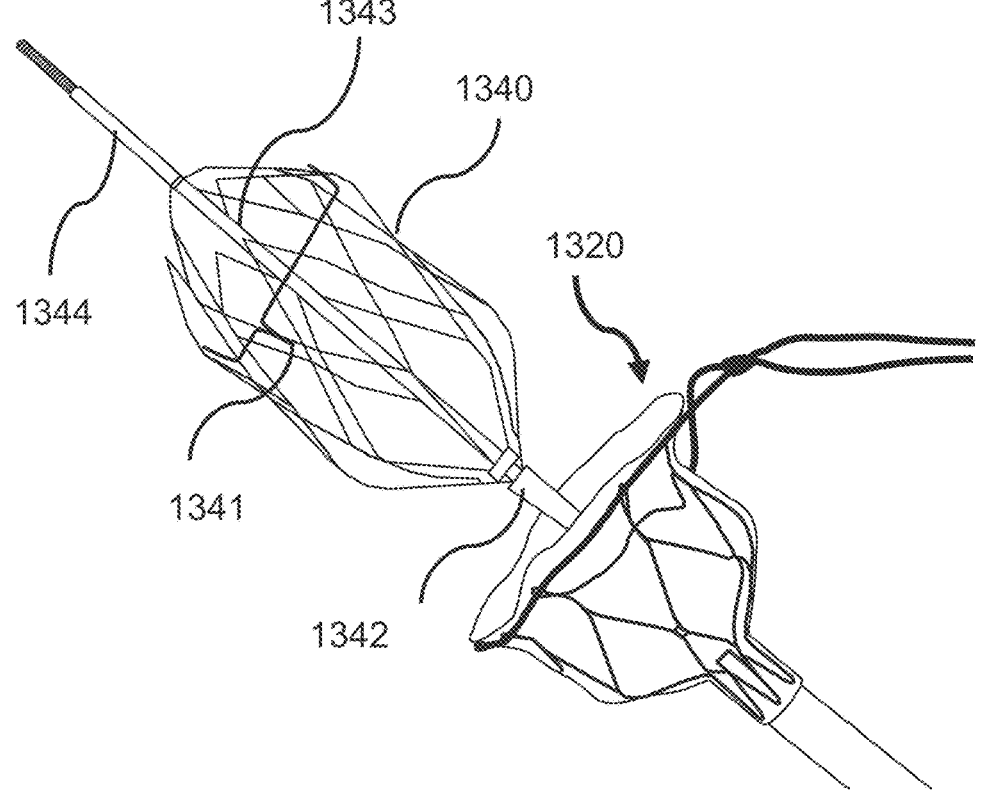
Figure 13C:
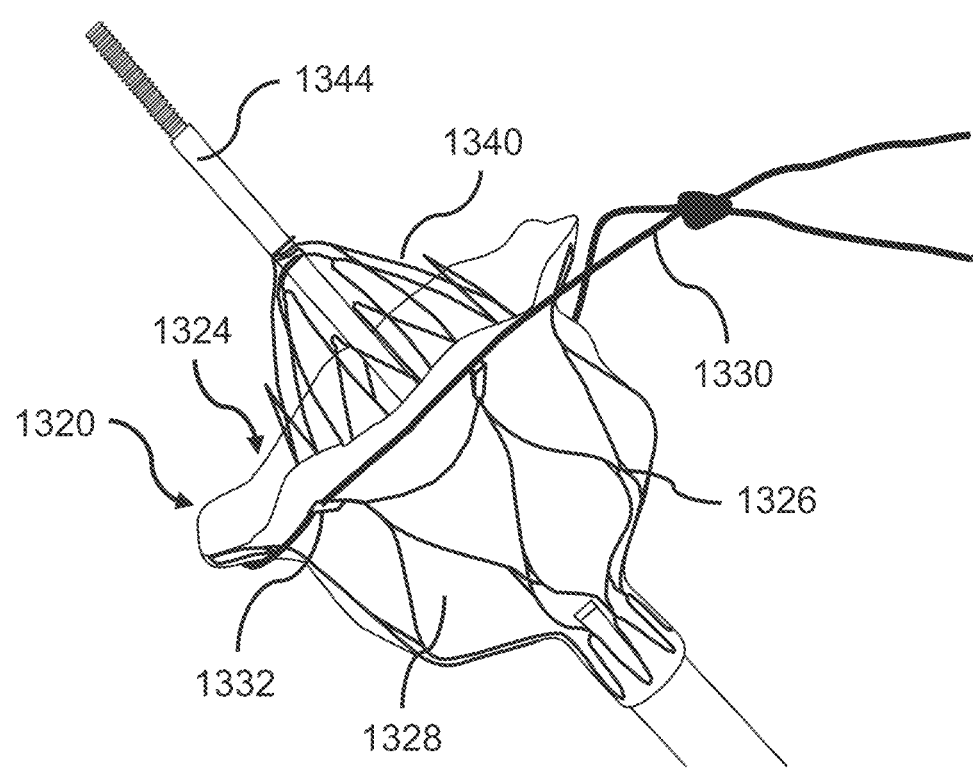

According to some exemplary embodiments, for example as shown in FIGS. 13B and 13C, an LAA reshaper, for example LAA reshaper 1340 is connected to an LAA reshaper guide, for example guide 1342. In some embodiments, the guide comprises an elongated rod, optionally a flexible elongated rod. In some embodiments, the LAA reshaper 1340 comprises a wire, a braided wire, a wire mesh or a slotted tube, shaped to form a closed or an opened tubular structure. In some embodiments, the LAA reshaper 1340 is formed from a one or more wires of a shape memory alloy, for example Nitinol. In some embodiments, the LAA reshaper 1340 is configured to be in a collapsed state within the working channel of the catheter or within the suction channel 1222, for example when inserting the catheter into the LA. Additionally, the LAA reshaper 1340 is configured to expand to an expanded state at least partly within the LAA. In some embodiments, in an expanded state, a maximal dimension of the LAA reshaper 1340, for example a maximal width 1341 of the LAA reshaper 1340 is larger than a width of the suction channel, for example suction channel 1322 or the width of the working channel of the catheter. In some embodiments, for example as shown in FIG. 13C, a maximal dimension of the LAA reshaper 1340 is smaller than a width of the opening 1324 of the vacuum inlet 1320, for example to allow movement of the LAA reshaper 1320 in and out from the vacuum inlet 1320 when the vacuum inlet 1320 is in an expanded state.

According to some exemplary embodiments, a portion of the guide 1342, for example portion 1343 passes through the LAA reshaper 1340. In some embodiments, a portion of the guide 1342, for example portion 1344, further extends out from the LAA reshaper 1340.

Exemplary LAA Closure

Reference is now made to FIGS. 14A-14I depicting closure of the LAA, according to some exemplary embodiments of the invention.

Figure 14A:
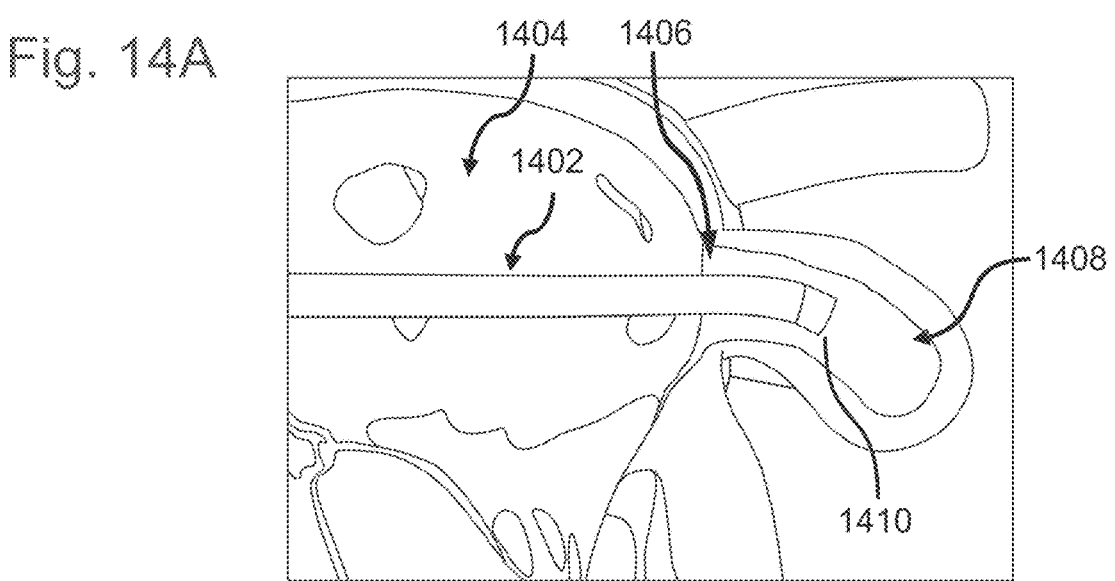
FIGS. 14A-14I are schematic illustrations demonstrating closure of the LAA, according to some exemplary embodiments of the invention.

According to some exemplary embodiments, for example as shown in FIG. 14A, a catheter of a body cavity closure device, for example catheter 1402 is navigated into the LA 1404. In some embodiments, the catheter 1402 is transseptally navigated into the LA 1404 from the RA (not shown). In some embodiments, the catheter is advanced through the LAA opening 1406 into the LAA 1408, for example to place a distal opening 1410 of the catheter 1402 within the LAA 1408. In some embodiments, the distal opening 1410 of the catheter 1402 is inserted to a distance of up to 20 mm, for example up to 15 mm, up to 10 mm or any intermediate, smaller or larger value, from the LAA opening 1406.

Figure 14B:
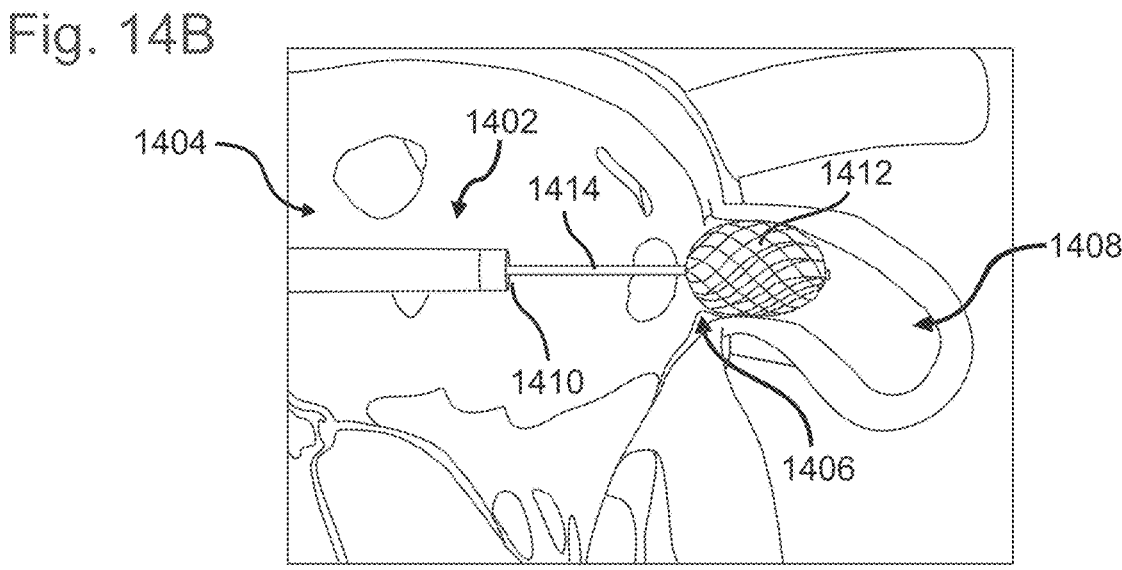

According to some exemplary embodiments, for example as shown in FIG. 14B, an LAA reshaper 1412 is expanded at least partly within the LAA 1408. In some embodiments, the LAA reshaper is expanded at least partly within the LAA opening 1406. In some embodiments, a guide 1414 of the LAA reshaper 1412 comprises an elongated rod, optionally a flexible elongated rod, having an expandable LAA reshaper 1412 at a distal end of the guide 1414. In some embodiments, the guide 1414 and the LAA reshaper 1412 are advanced within an inner working channel of the catheter 1402 towards the distal opening 1410 of the catheter 1402.

According to some exemplary embodiments, the guide 1414 and the LAA reshaper 1412 are forwardly advanced through the distal opening 1410 into the LAA 1408. Alternatively or additionally, the catheter 1402 is retracted, for example to expose the LAA reshaper 1412. In some embodiments, the LAA reshaper 1412 expands at least partly within the LAA 1408, for example to block passage of floating material and particles, from the LAA 1408 into the LA 1404, through the LAA opening 1406. In some embodiments, the LAA reshaper 1412 is semi-permeable, for example to block passage of blood clots and cell debris but to allow passage of blood between the LA 1404 and the LAA 1408.

According to some exemplary embodiments, the LAA reshaper 1412 comprises one or more openings having a maximal dimension, for example a maximal width or a maximal diameter, in a range of 5 μm-1000 μm, for example 50 μm-200 μm, 100 μm-500 μm, 300 μm-500 μm, 400 μm-800 μm, 600 μm-1000 μm or any intermediate, smaller or larger range of values. In some embodiments, the LAA reshaper 1412 comprises a mesh having pores having a maximal dimension, for example maximal width or maximal diameter in a range of 5 μm-1000 μm, for example 50 μm-200 μm, 100 μm-500 μm, 300 μm-500 μm, 400 μm-800 μm, 600 μm-1000 μm or any intermediate, smaller or larger range of values.

Figure 14C:
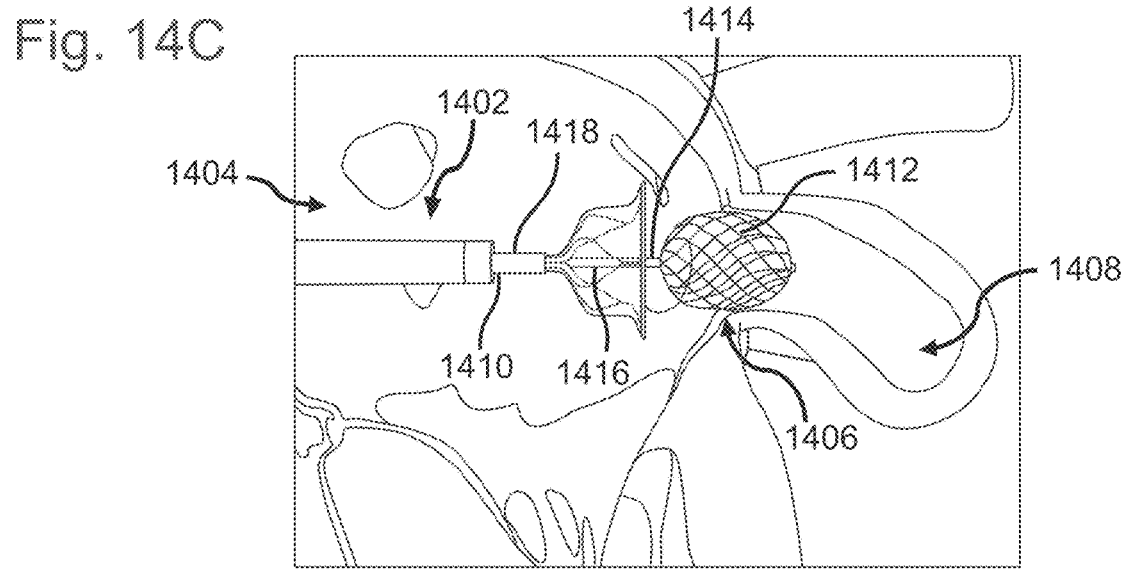

According to some exemplary embodiments, for example as shown in FIG. 14C, an elongated suction channel 1418 terminating with a vacuum inlet 1416 is forwardly advanced from within the inner working channel of the catheter 1402 and through the distal opening 1410 of the catheter 1402 into the LA 1404. In some embodiments, the vacuum inlet 1416 comprises an expandable vacuum inlet, configured to expand when exiting through the distal opening 1410. In some embodiments, the vacuum inlet 1416 expands within the LA.

Figures 14D, 14E, 14F:
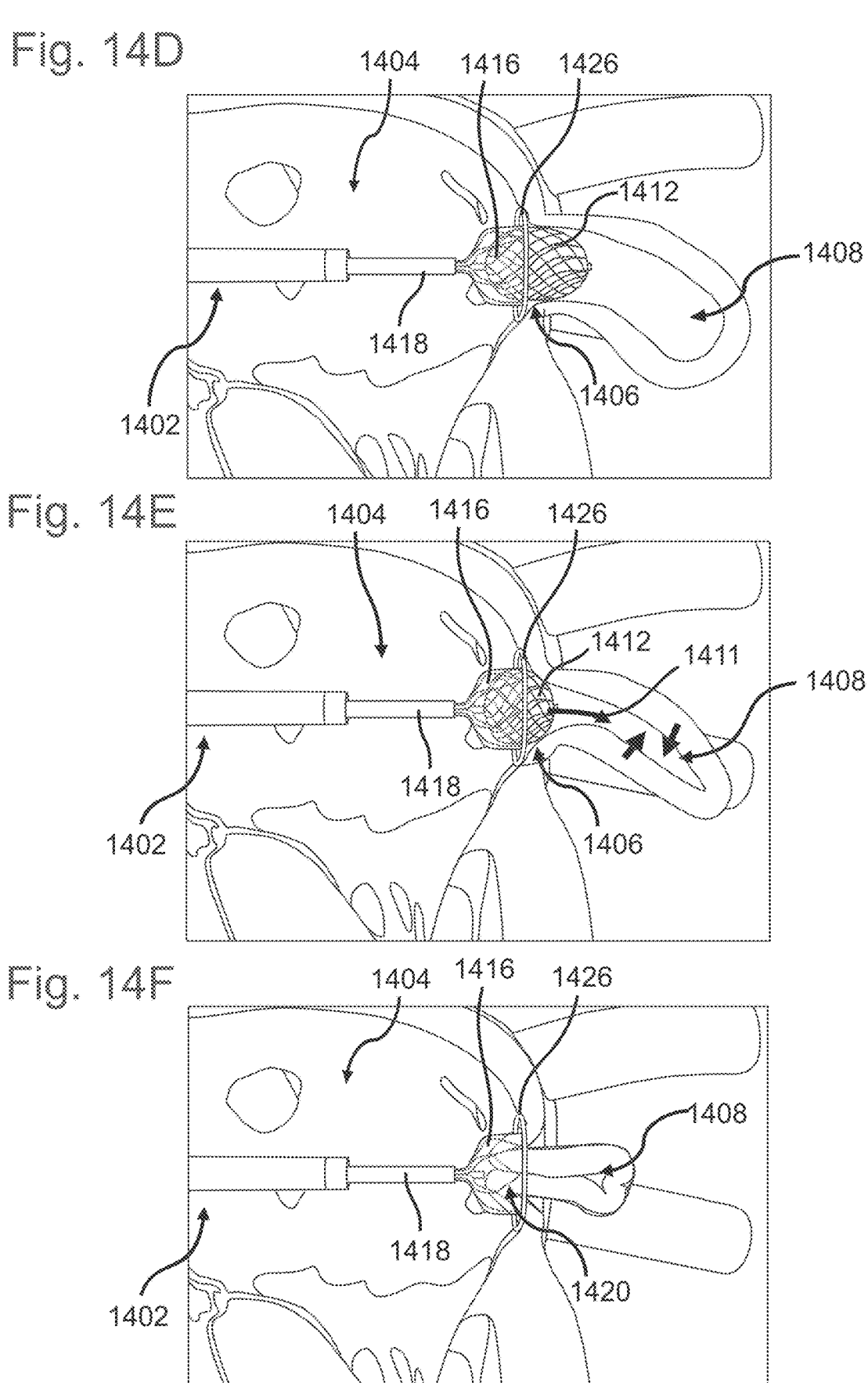

According to some exemplary embodiments, for example as shown in FIG. 14D, the vacuum inlet 1416, for example a distal opening of the vacuum inlet 1416 facing the LAA, is pushed against the LA wall surrounding the LAA opening 1406. In some embodiments, the vacuum inlet 1416 is pushed against the LA wall with a force sufficient to form a sealed passage between the suction channel 1418 and the LAA 1408. In some embodiments, the sealed passage limits the passage between the LAA 1408 and the LA 1404 in at least 80%, for example at least 80%, at least 85%, at least 90%, at least 95% or any intermediate, smaller or larger percentage.

According to some exemplary embodiments, a fastener, for example a fastener loop 1426 is coupled to the vacuum inlet 1416. In some embodiments, the fastener loop 1426 is coupled to the vacuum inlet 1416 around the distal opening of the vacuum inlet 1416. In some embodiments, the fastener loop 1426 is coupled to the vacuum inlet 1416 at a distance of up to 20 mm, for example up to 15 mm, up to 10 mm, up to 5 mm from a contact site between the vacuum inlet 1416 and the LA wall.

According to some exemplary embodiments, for example as shown in FIG. 14E, vacuum 1411 is applied through the vacuum inlet 1416 into the LAA 1408. In some embodiments, the vacuum 1411 applies a force of up to 30 Newtons (N), for example up to 10N, up to 15N, up to 20N, up to 25N, up to 30N or any intermediate, smaller or larger value, on the LAA tissue. In some embodiments, the applied vacuum causes a collapse, for example an inward collapse of the LAA. In some embodiments, the vacuum is applied while the vacuum inlet 1416 is in contact with the LA wall surrounding the LA opening 1406. In some embodiments, the LAA reshaper 1412 is retracted into the catheter 1402 while vacuum is applied onto the LAA 1408.

According to some exemplary embodiments, for example as shown in FIG. 14F, the applied vacuum invaginates at least a portion of the LAA, for example portion 1420, into the vacuum inlet 1416, positioned in the LA 1404. In some embodiments, at least 5%, for example at least 10%, at least 15% or any intermediate, smaller or larger range of percentage of the LAA 1408, is invaginated into the LA 1404.

Figure 14G:
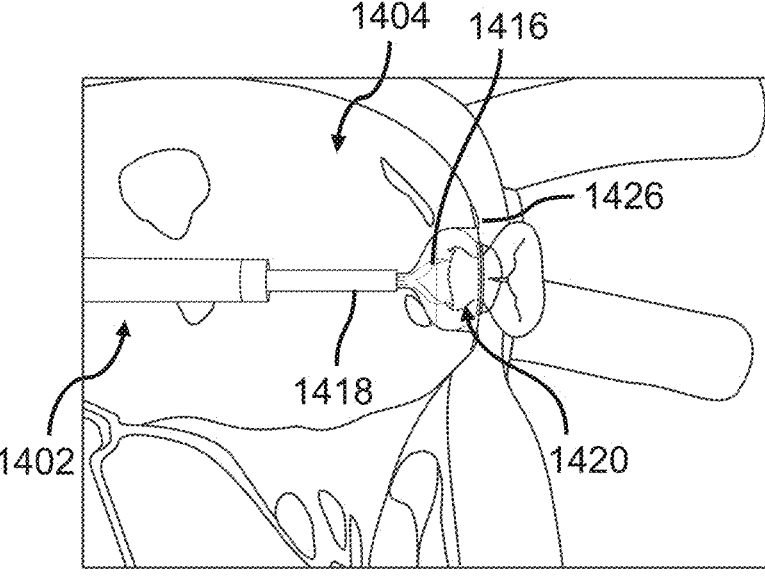

According to some exemplary embodiments, for example as shown in FIG. 14G, a fastener, for example fastener loop 1426 coupled to the vacuum inlet 1416, is positioned around the invaginated portion of the LAA, for example portion 1420. In some embodiments, the fastener is positioned around a base of the invaginated portion 1420 located within the vacuum inlet 1416. In some embodiments, the fastener loop 1426 is fastened around the invaginated portion 1420 while the invaginated portion 1420 is at least partly within the vacuum inlet 1416. In some embodiments, the fastener, for example fastener loop 1426 comprises one or more anchors (not shown), for example a hook or a pin, shaped and sized to penetrate into the invaginated portion 1420 of the LAA. In some embodiments, the one or more anchors are configured to anchor the fastener to the invaginated portion. Optionally, the one or more anchors are configured to irreversibly anchor the fastener to the invaginated portion of the LAA. In some embodiments, the fastener is fastened around the invaginated portion with a force that closes the LAA opening, for example permanently closes the LAA opening.

Figure 14H:
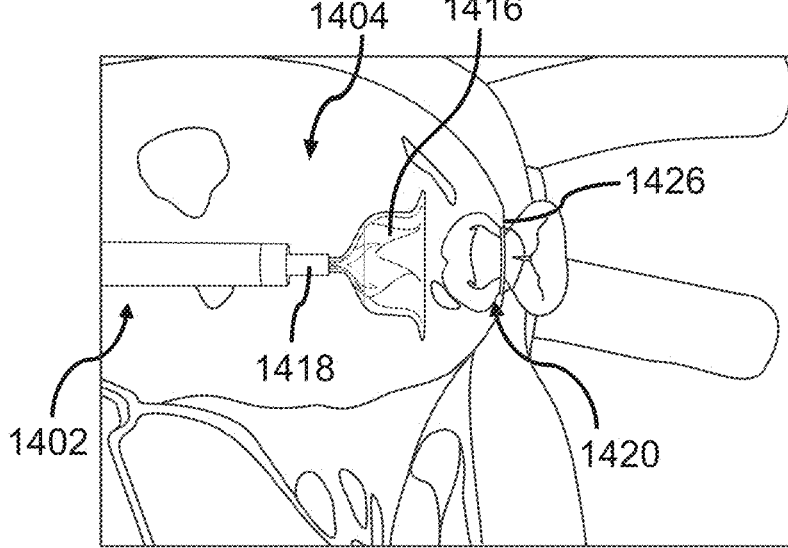

According to some exemplary embodiments, for example as shown in FIG. 14H, the fastener, for example fastener loop 1426, is decoupled from the vacuum inlet 1416 when fastened around the invaginated portion 1420. In some embodiments, the fastener is decoupled from the vacuum inlet 1416 when the fastener is anchored to the invaginated portion 1420. Additionally or alternatively, the fastener is decoupled from the vacuum inlet 1416, when the suction channel 1418 and the vacuum inlet 1416 are retracted into the working channel of the catheter 1402.

Figure 14I:
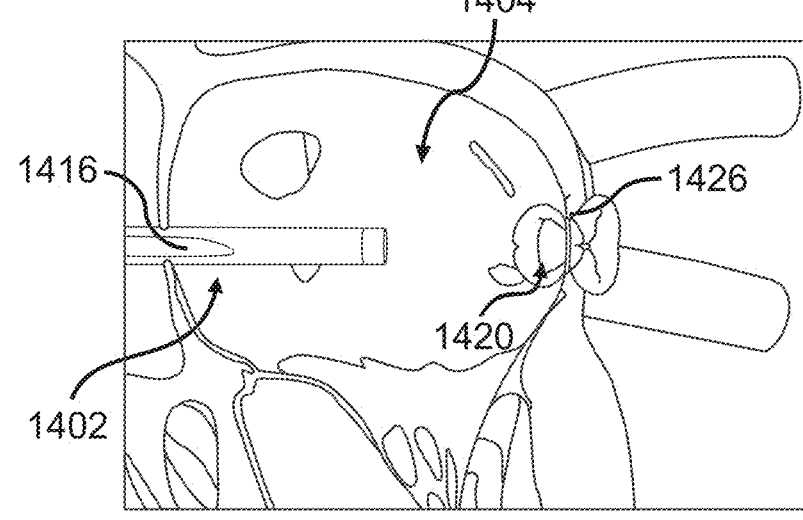
Figure 15:
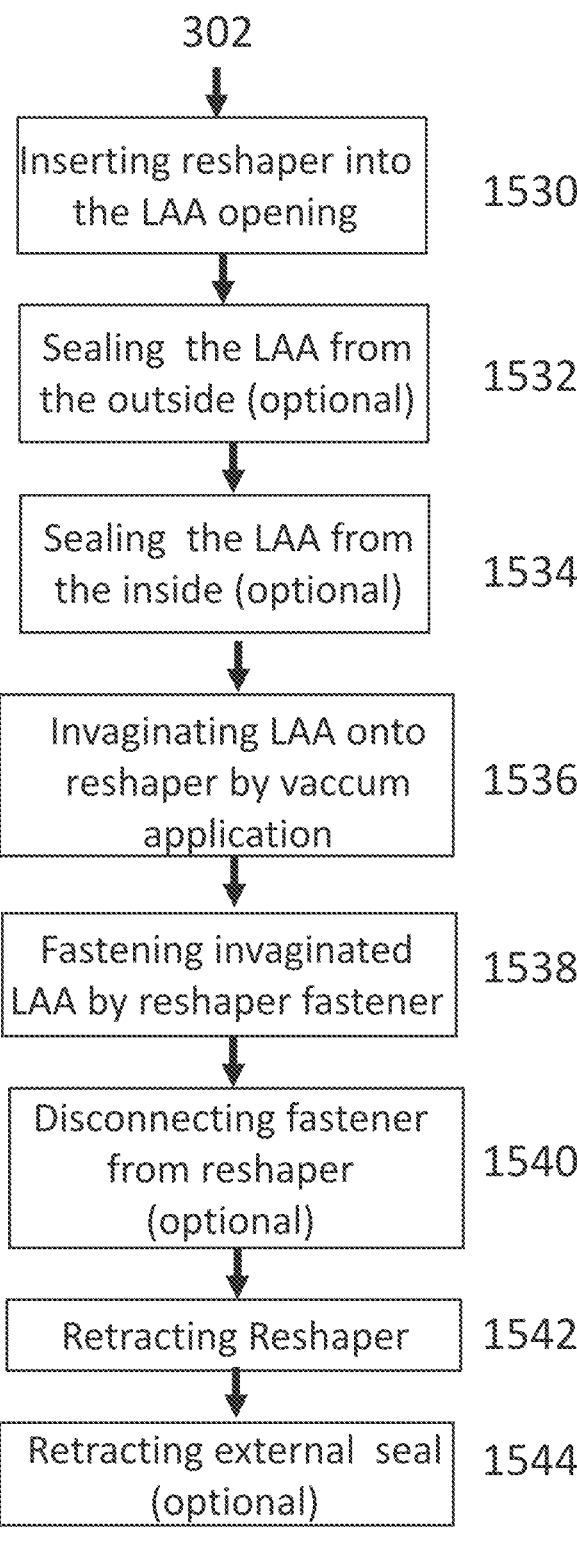
FIG. 15 is a flow chart of a process for closing the LAA by a ligator, for example a fastener, coupled to an LAA reshaper, according to some exemplary embodiments of the invention.

According to some exemplary embodiments, for example as shown in FIG. 14I, the vacuum inlet 1416 is collapsed and retracted into the working channel of the catheter 1402. In some embodiments, the vacuum inlet 1416 is collapsed and retracted into the working channel of the catheter 1402 while the fastener remains fastened around the invaginated portion of the LAA, inside the LA. In some embodiments, once the vacuum inlet 1416 is within the catheter 1402, the catheter is retracted from the heart of the patient.

Exemplary LAA Closure by a Reshaper Coupled to a Ligator

Reference is now made to FIG. 15 and FIGS. 16A-16H depicting a process for closure of the LAA by a reshaper coupled to a ligator, according to some exemplary embodiments of the invention.

According to some exemplary embodiments, a catheter is introduced into the LA at block 302, for example as described in FIG. 3.

According to some exemplary embodiments, a reshaper, for example an LAA reshaper is inserted into the LAA, through the LAA opening, at block 1530. In some embodiments, the LAA reshaper is inserted into the LAA opening in a collapsed state. In some embodiments, the reshaper is introduced at least partly into the LAA through the LAA opening, for example, up to a distance of 1 cm, 2 cm, 4 cm, 5 cm, or any intermediate, smaller or larger distance from the inner wall of the LA surrounding the LAA opening. In some embodiments, the penetration distance of the LAA reshaper into the LAA determines the percentage of reshaped LAA tissue following invagination. Optionally, the penetration distance is adjusted according to a size and/or shape of the LAA in a subject.

According to some exemplary embodiments, and optionally, the LAA is sealed from the outside, at block 1532. In some embodiments, the LAA is sealed from the outside, for example, by attaching a seal, for example a vacuum inlet to the LA wall around the LAA opening. In some embodiments, a vacuum inlet, for example the vacuum inlet 420 shown in FIG. 4A, the vacuum inlet 620 shown in FIG. 6A, and/or the vacuum inlet 700 shown in FIG. 12A are examples of an external seal of the LAA opening. In some embodiments, the LAA is sealed by applying vacuum after attachment of the seal around the LAA opening. In some embodiments, the applied vacuum through the seal allows, for example, better attachment of the seal to the LA wall. In some embodiments, the seal is applied from the outside continuously, for example until at least a portion of the LAA is invaginated and fastened. Alternatively, vacuum is applied through the seal until invagination is completed.

According to some exemplary embodiments, for generating a seal from the outside, vacuum levels of at least 5 mmHg, for example at least 10 mmHg, at least 15 mmHg, or any intermediate, smaller or larger pressure levels are applied.

According to some exemplary embodiments, and optionally, the LAA is sealed from the inside at block 1534. In some embodiments, the LAA is sealed by placing an inner seal at least partly within the LAA. In some embodiments, the inner seal is attached to the walls of the LAA. Additionally or alternatively, the inner seal is attached to the walls of the LAA opening. In some embodiments, the inner seal is an expandable inner seal, configured to expand to contact the walls of the LAA and/or the walls of the LAA opening. In some embodiments, the inner seal is the LAA reshaper inserted at block 1530.

According to some exemplary embodiments, the LAA is invaginated, at least partly, onto the reshaper at block 1536. In some embodiments, the LAA is invaginated at least partly into the LAA reshaper at block 1536. In some embodiments, the LAA is invaginated by applying vacuum, for example on the LAA lumen and/or the LAA inner walls. In some embodiments, the LAA is invaginated by applying vacuum levels of at least of at least 5 mmHg, for example at least 10 mmHg, at least 15 mmHg, or any intermediate, smaller or larger pressure levels are applied. In some embodiments, the LAA is at least partly invaginated into the LA. Alternatively, the invaginated LAA is positioned outside the LA. In some embodiments, the vacuum is applied through the external seal, for example the vacuum inlet positioned outside the LAA. Alternatively or additionally, the vacuum is applied through the LAA reshaper, positioned at least partly within the LAA.

According to some exemplary embodiments, the invaginated portion of the LAA is fastened at block 1538. In some embodiments, the invaginated portion of the LAA is fastened by a fastener coupled, for example reversibly coupled, to the LAA reshaper. In some embodiments, the invaginated portion of the LAA is fastened, for example by collapsing the fastener on the invaginated portion of the LAA. Alternatively or additionally, the invaginated portion of the LAA is fastened, for example by constricting the fastener.

According to some exemplary embodiments, the fastener is optionally disconnected from the reshaper at block 1540. Alternatively, fastening of the LAA at block 1538 disconnects the fastener from the reshaper. In some embodiments, the fastener is disconnected from the reshaper at block 1540, for example pulling a string which includes a tearing region configured to be torn by application of force, for example a region in the string where the string structure is weakened, optionally, by having a cut which reduces the coupling to the fastener.

According to some exemplary embodiments, the reshaper is retracted from the LA at block 1542. In some embodiments, the reshaper is retracted into the lumen of the catheter. In some embodiments, the reshaper is retracted once invagination and/or fastening is completed. In some embodiments, the reshaper is collapsed to fit into the inner lumen of the catheter.

According to some exemplary embodiments, optionally, the external seal is retracted at block 1544. In some embodiments, the external seal is retracted from the LA, for example through the inner lumen of the catheter. In some embodiments, the external seal is collapsed, for example to fit into the inner lumen of the catheter at block 1544.

Figure 16A:
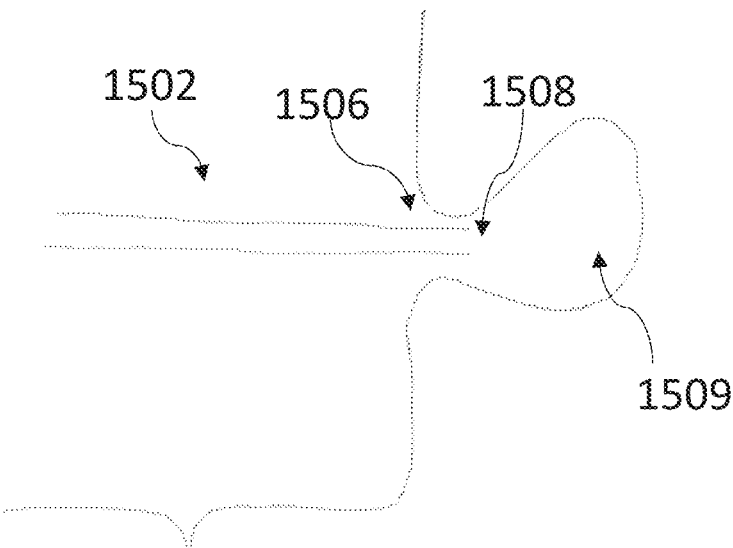
FIGS. 16A-16H are schematic illustrations showing closure of the LAA by a ligator coupled to a LAA reshaper, according to some exemplary embodiments of the invention.

According to some exemplary embodiments, for example as shown in FIG. 16A, a catheter 1502 is navigated into the LA 1504. In some embodiments, a distal opening 1508 of the catheter, for example an opening located at a distal tip of the catheter, facing the tissue, is advanced at least partly through the LAA opening 1506 into the LAA 1509. In some embodiments, the catheter distal opening 1508 is positioned at a location in the LAA 1509 or in the LAA opening 1506 suitable for deployment of an LAA reshaper.

In some embodiments, the catheter is introduced up to 6 cm into the LAA, for example up to 5 cm, up to 3 cm, up to 1 cm into the LAA.

According to some exemplary embodiments, the LAA opening has a diameter or a maximal width of up to 6 cm, for example up to 5 cm, up to 3 cm, up to 2 cm or any intermediate, smaller or larger value.

Figure 16B:
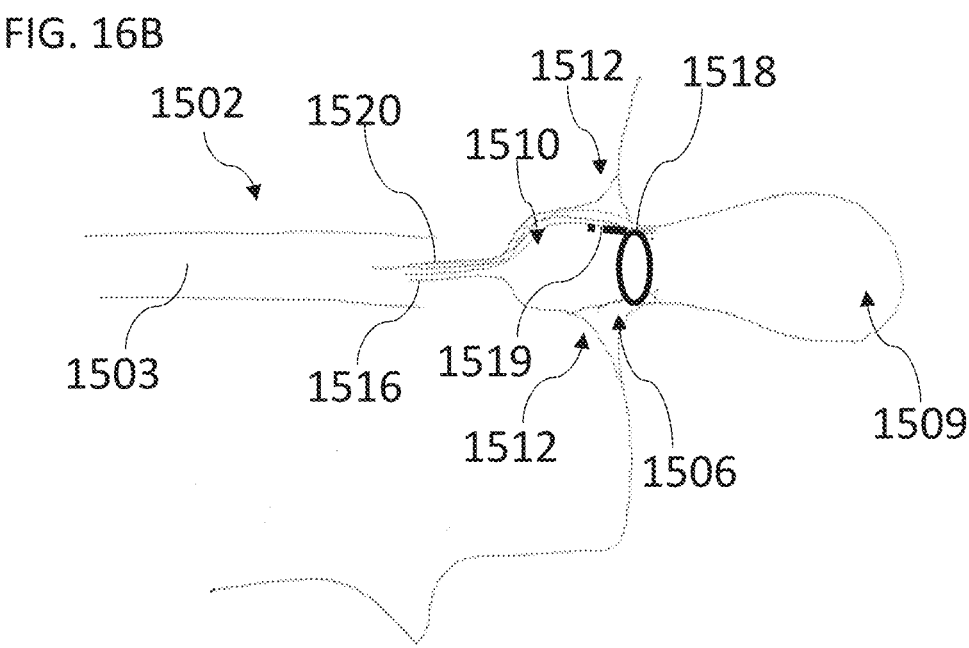

According to some exemplary embodiments, for example as shown in FIG. 16B, an external seal, for example a vacuum inlet 1512 is deployed in the LA 1504. In some embodiments, the external seal is advanced through the inner lumen 1503 of the catheter and is expanded through the catheter distal opening 1508 in the LA. In some embodiments, the external seal 1512 is coupled to a proximal channel 1516 traveling through the catheter inner lumen 1503. In some embodiments, the proximal channel and the external seal form a closed and sealed passage, for example to allow application of vacuum. In some embodiments, the proximal channel 1516 is connected to a vacuum source located outside the body of the patient.

According to some exemplary embodiments, for example as shown in FIG. 16B, an LAA reshaper 1510 is deployed at least partly within the LAA 1508. In some embodiments, the LAA reshaper 1510 is deployed out from a distal opening of the external seal 1512, for example from the proximal channel 1516 of the external seal 1512. In some embodiments, the LAA reshaper 1510 is expanded at least partly within the LAA 1508, for example to contact the walls of the LAA.

Figure 16C:
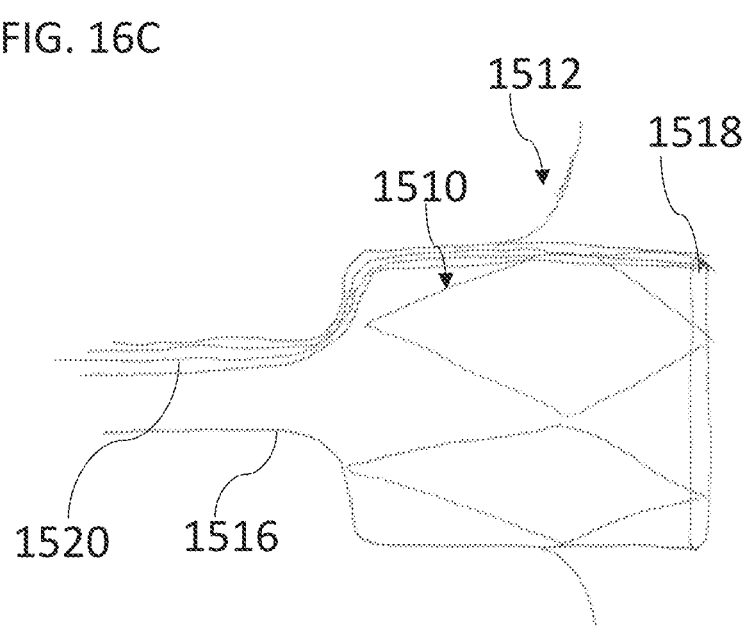
Figure 16D:
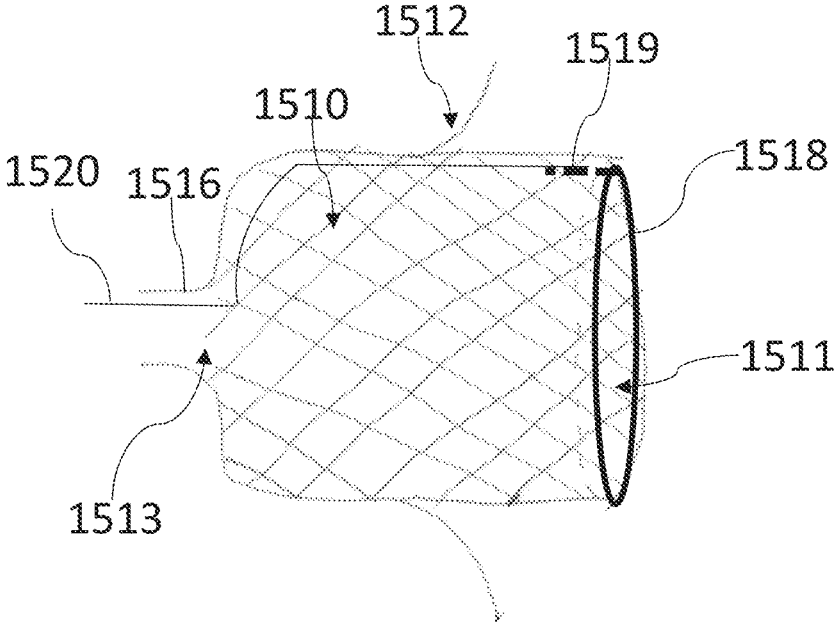

According to some exemplary embodiments, for example as shown in FIGS. 16C and 16D, the LAA reshaper 1510 is an expandable LAA reshaper, formed from a mesh. In some embodiments, the mesh is formed from one or more wires. In some embodiments, the LAA reshaper 1510 has a cylindrical shape having, in an expanded state a wide distal opening 1511 configured to face the LAA and located away from the catheter, and a proximal narrower proximal opening 1513 connected to a reshaper guide1516 which travels within the catheter inner lumen. Optionally, the reshaper guide 1516 is located within the channel of the external seal 1512.

According to some exemplary embodiments, the external surface and/or the internal surface of the LAA reshaper 1510 is at least partly coated, for example with a sheet or a membrane. In some embodiments, the reshaper 1510 is coated to form a path, which is at least partly sealed, between the reshaper channel 1511 and the LAA 1509. In some embodiments, the reshaper coating is made from Polyurethane, expanded polytetrafluoroethylene (ePTFE), Nylon or any type of coating or membrane.

According to some exemplary embodiments, for example as shown in FIG. 16D, a fastener 1518, is coupled, for example reversible coupled, to the LAA reshaper 1510. In some embodiments, the fastener 1518 is coupled to the external surface of the reshaper 1510. Alternatively, the fastener 1518 is coupled to the inner surface of the reshaper 1510. In some embodiments, the fastener 1518 is coupled to the LAA reshaper 1510, for example around the distal opening 1511. Alternatively, the fastener 1518 is coupled to the LAA reshaper 1510, for example along the circumference of the LAA reshaper 1510. In some embodiments, the fastener 1518 is coupled to the reshaper 1510 at a distance of up to 6 cm, for example up to 5 cm, up to 3 cm or any intermediate, smaller or larger distance from the distal opening 1511. In some embodiments, the fastener 1518 comprises a lariat, a lasso, or a clamp.

According to some exemplary embodiments, for example as shown in FIG. 16D, the fastener 1518 is coupled to a fastener manipulator, for example fastener actuator 1520 by a releasable coupling portion 1519. In some embodiments, the fastener actuator 1520 comprises a string, and the releasable coupling portion 1519 comprises a tearing region between the fastener actuator 1520 and the fastener 1518.

Figure 16E:
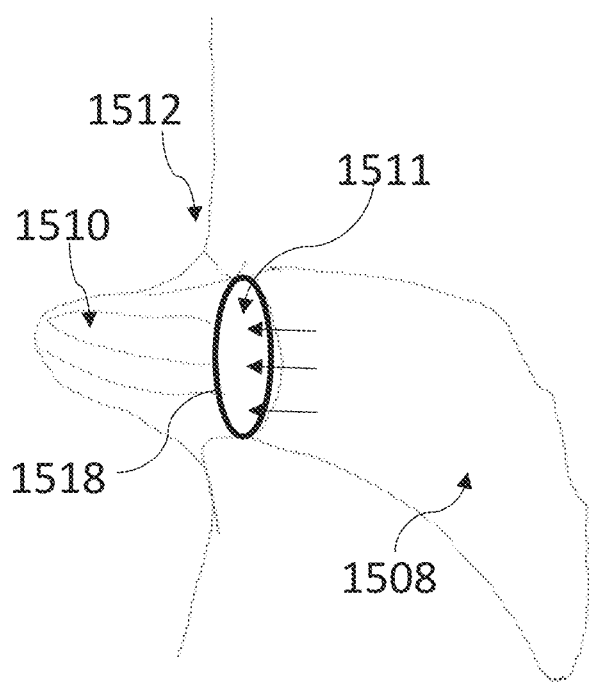
Figure 16F:
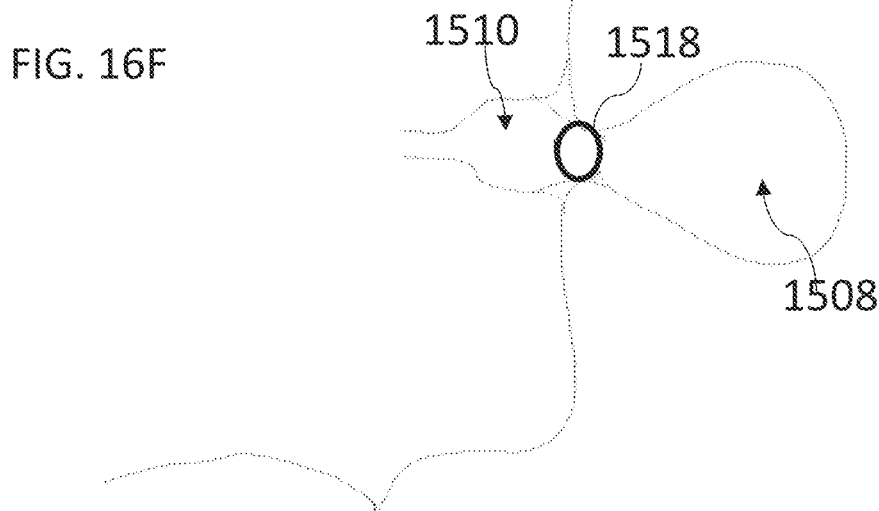

According to some exemplary embodiments, for example as shown in FIG. 16E, once the LAA reshaper 1510 is positioned at least partly within the LAA 1508, vacuum is applied on the LAA 1518, through the distal opening 1511 of the reshaper 1510. In some embodiments, vacuum is applied through the channel of the external seal 1512, for example the vacuum inlet attached to the LA wall. Alternatively or additionally, vacuum is applied through the channel of the reshaper 1510. In some embodiments, for example as shown in FIG. 16F, the applied vacuum causes the LAA 1508 to shrink in volume.

Figure 16G:
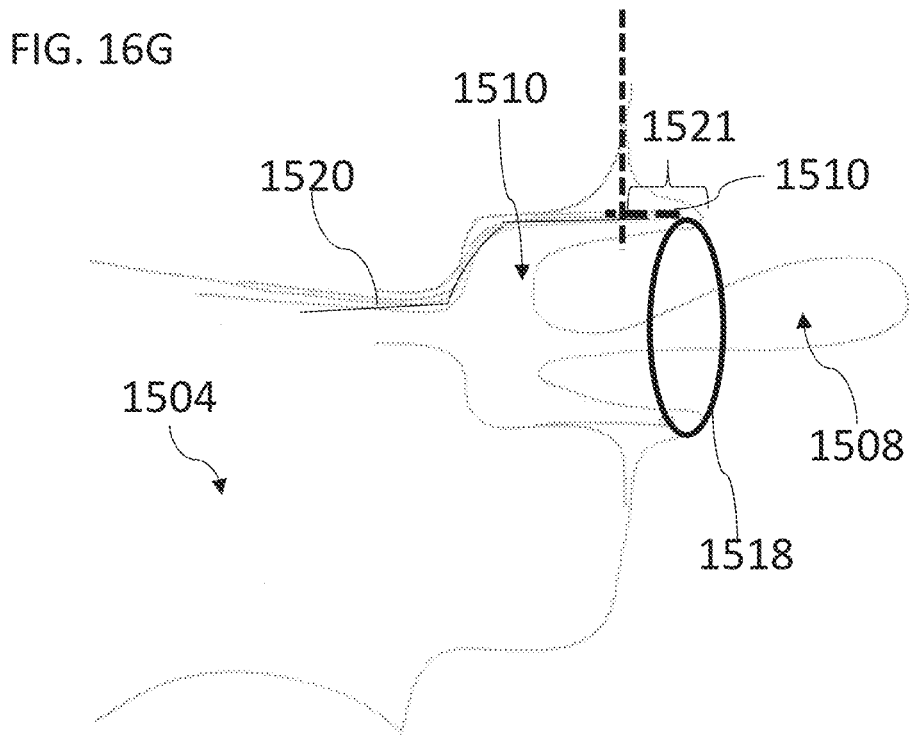

According to some exemplary embodiments, for example as shown in FIG. 16G, at least a portion of the LAA 1508 is invaginated into the reshaper 1510. Alternatively or additionally, the at least a portion of the LAA 1508 is invaginated onto an inner surface of the LAA reshaper 1510. In some embodiments, the at least a portion of the LAA 1508 is invaginated at least partly into the LA. In some embodiments, the at least a portion of the LAA 1508 is invaginated proximal to the fastener 1518 coupled to the reshaper 1510.

According to some exemplary embodiments, for example as shown in FIG. 16G, the penetration distance 1521 of the reshaper 1510 into the LAA 1508 determined the size of the LAA portion invaginated onto the reshaper 1510. In some embodiments, the penetration distance 1521 is a minimal distance of the distal reshaper opening from the LA wall surrounding the LAA opening. In some embodiments, the penetration distance 1521 is adjusted according to at least one of the LAA shape, the LAA volume, the LAA opening width or diameter.

According to some exemplary embodiments, the fastener comprises a roeder knot, for example as described in J. J. Hage, Surg Laparosc Endosc Percutan Tech 2008 February; 18(1):1-7, that allows, for example, tightening of the fastener around the invaginated portion of the LAA.

Figure 16H:
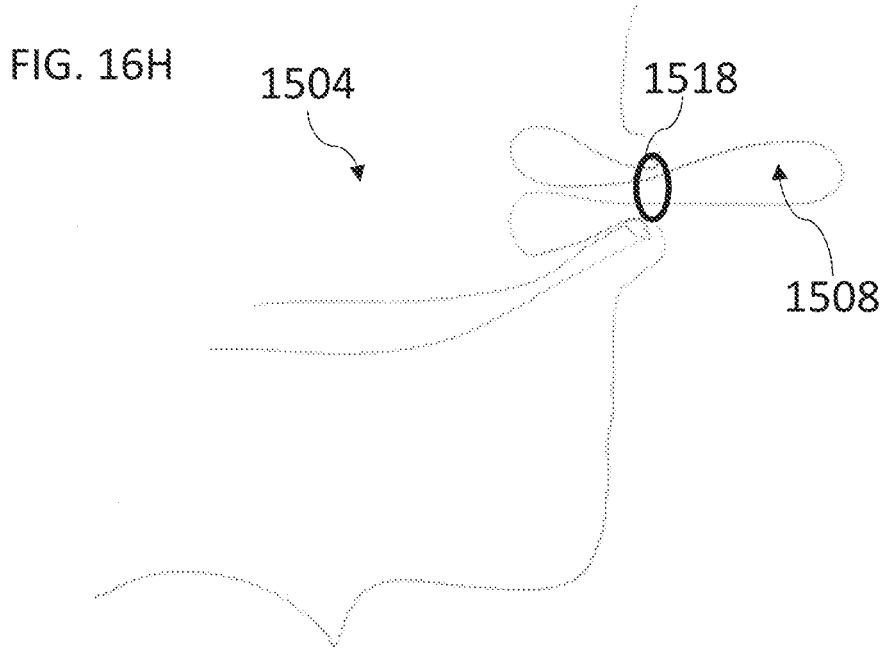

According to some exemplary embodiments, for example as shown in FIG. 16H, fastening of the fastener 1518 around the invaginated LAA, decouples the fastener 1518 from the reshaper 1510. In some embodiments, the fastener 1518 disconnects from the fastener actuator 1520 after the fastener 1518 is fastened around the invaginated LAA portion. In some embodiments, the fastener actuator 1520 is disconnected from the fastener by applying force on the releasable coupling portion 1519, that causes for example tearing of the tearing region of said releasable coupling portion 519. Alternatively, the fastener actuator 1520 and/or the fastener 1518 comprises a cutting mechanism, for example a Sure-CUT™ Suture Cutter.

It is expected that during the life of a patent maturing from this application many relevant vacuum inlets and fasteners will be developed; the scope of the terms vacuum inlet and fastener is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein, and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for closure of a left atrial appendage (LAA), comprising:

placing in an expanded state, an expandable LAA reshaper having openings in an external side surface, at least partly inside said LAA, and in contact with an LAA wall or near said LAA wall;

applying vacuum on said LAA from a vacuum inlet in a left atrium (LA) outside the LAA, via said expandable LAA reshaper and said openings with a force sufficient to attach an LAA wall surrounding said expandable LAA reshaper to said external side surface of said expandable LAA reshaper;

reshaping said LAA by applying force by said expandable LAA reshaper on said LAA wall from within said LAA while applying said vacuum;

closing an opening of said LAA while said LAA is reshaped following said reshaping and said applying vacuum.

2. A method according to claim 1, comprising extending a suction channel terminating with said vacuum inlet into said LA, and placing said vacuum inlet in contact with an LA wall surrounding or near an opening of said LAA, prior to said applying.

3. A method according to claim 1, wherein said applying vacuum comprising applying said vacuum with a force sufficient to at least partly inwardly collapse said LAA onto said expandable LAA reshaper.

4. A method according to claim 1, wherein said placing comprises expanding said expandable LAA reshaper at least partly within the LAA, and wherein said reshaping comprises applying force by said expanded expandable LAA reshaper on said LAA wall from within said LAA.

5. A method according to claim 4, comprising retracting said expandable LAA reshaper into said LA while applying said force.

6. A method according to claim 5, comprising applying said vacuum on said LAA during said retracting.

7. A method according to claim 6, wherein said applied vacuum comprises high pressure vacuum in a range of 400-900 mmHg.

8. A method according to claim 1, wherein said placing comprises inserting said expandable LAA reshaper up to 30 mm into said LAA.

9. A method according to claim 1, comprising reshaping by said expandable LAA reshaper the LAA during invagination of said LAA.

10. A method according to claim 1, comprising:

invaginating during said applying vacuum and while retracting said expandable LAA reshaper into said LA, at least a portion of said LAA into the LA;

removing said expandable LAA reshaper from the LAA;

wherein said closing comprises fastening said invaginated at least a portion of said LAA.

11. A method according to claim 1, wherein said expandable LAA reshaper comprises a distal expandable portion, wherein said openings are openings in an external side surface of said distal expandable portion, and wherein said placing comprises placing said distal expandable portion in said expanded state at least partly inside said LAA.

12. A method according to claim 1, wherein said closing comprises fastening at least a portion of said LAA.

13. A method according to claim 1, comprising anchoring said expandable LAA reshaper to said LAA wall.

14. A method according to claim 1, wherein said reshaping comprises reshaping during said applying vacuum said LAA, by applying force from within said LAA by said expandable LAA reshaper on said LAA wall in contact with said external side surface of said expandable LAA reshaper, wherein said reshaping comprises moving said LAA reshaper within said LAA while applying said force on said LAA wall.

* * * * *